US009630950B2

(12) United States Patent
Dervan et al.

(10) Patent No.: US 9,630,950 B2
(45) Date of Patent: *Apr. 25, 2017

(54) INHIBITORS FOR STEROID RESPONSE ELEMENTS AND RNA POLYMERASE II AND RELATED METHODS

(71) Applicants: Peter B. Dervan, San Marino, CA (US); Nicholas G. Nickols, Van Nuys, CA (US); Claire S. Jacobs, Cambridge, MA (US); Michelle E. Farkas, Amherst, MA (US); Daniel A. Harki, Minneapolis, MN (US)

(72) Inventors: Peter B. Dervan, San Marino, CA (US); Nicholas G. Nickols, Van Nuys, CA (US); Claire S. Jacobs, Cambridge, MA (US); Michelle E. Farkas, Amherst, MA (US); Daniel A. Harki, Minneapolis, MN (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/027,073

(22) Filed: Sep. 13, 2013

(65) Prior Publication Data

US 2014/0194483 A1 Jul. 10, 2014

Related U.S. Application Data

(63) Continuation-in-part of application No. 12/148,943, filed on Apr. 22, 2008, now Pat. No. 8,835,480.

(60) Provisional application No. 60/926,080, filed on Apr. 23, 2007, provisional application No. 61/700,795, filed on Sep. 13, 2013.

(51) Int. Cl.
  *C07D 403/14* (2006.01)
  *A61K 31/785* (2006.01)

(52) U.S. Cl.
  CPC .......... *C07D 403/14* (2013.01); *A61K 31/785* (2013.01)

(58) Field of Classification Search
  None
  See application file for complete search history.

(56) References Cited

U.S. PATENT DOCUMENTS

| | | | |
|---|---|---|---|
| 5,998,140 A | 12/1999 | Dervan | |
| 6,090,947 A | 7/2000 | Dervan | |
| 6,143,901 A | 11/2000 | Dervan | |
| 6,303,312 B1 | 10/2001 | Dervan | |
| 6,472,537 B1 | 10/2002 | Baird | |
| 6,506,906 B1 | 1/2003 | Dervan | |
| 6,545,162 B1 | 4/2003 | Dervan | |
| 6,555,692 B1 | 4/2003 | Dervan | |
| 6,559,125 B1 | 5/2003 | Dervan | |
| 6,635,417 B1 | 10/2003 | Dervan | |
| 6,660,255 B1 | 12/2003 | Gottesfeld | |
| 6,673,940 B1 | 1/2004 | Dervan | |
| 6,958,240 B1 | 10/2005 | Baird | |
| 7,049,061 B1 | 5/2006 | Baird | |
| 7,087,378 B1 | 8/2006 | Baird | |
| 7,452,730 B2 | 11/2008 | Dervan | |
| 7,589,171 B2 | 9/2009 | Bashkin | |
| 7,935,530 B2 * | 5/2011 | Dervan | C12N 15/63 435/440 |
| 8,835,480 B2 * | 9/2014 | Dervan | A61K 31/785 514/400 |
| 2003/0109448 A1 | 6/2003 | Crowley | |
| 2005/0026174 A1 | 2/2005 | Dervan | |
| 2006/0014163 A1 | 1/2006 | Dervan | |
| 2006/0019972 A1 | 1/2006 | Dervan | |
| 2006/0025429 A1 | 2/2006 | Dervan | |
| 2006/0270727 A1 | 11/2006 | Melander | |
| 2009/0042965 A1 * | 2/2009 | Dervan et al. ................ 514/397 |

FOREIGN PATENT DOCUMENTS

| | | |
|---|---|---|
| WO | WO 97/30975 | 8/1997 |
| WO | WO 98/35702 | 8/1998 |
| WO | WO 98/37066 | 8/1998 |
| WO | WO 98/37087 | 8/1998 |
| WO | WO 98/45284 | 10/1998 |
| WO | WO 98/49142 | 11/1998 |
| WO | WO 98/50058 | 11/1998 |
| WO | WO 03/041128 | 5/2003 |

OTHER PUBLICATIONS

Mrksich, Milan and Dervan, Peter B.; J. Am. Chem. Soc. (1995) 117 p. 3325-3332.*
Best, Timothy P. et al; "Nuclear localization of pyrrole-imidazole polyamide-fluorescein conjugates in cell culture." Proc. Natl. Acad. Sci. (2003) 100(21) p. 12063-12068.*
Lanz, Edvard et al; "Use of fitc as a flurescent probe for intracellular pH measurement." J. Fluoresc. (1997) 7(4) p. 317-319.*
Nichols, Nicholas G. et al; "Improved nuclear localization of dna binding polyamides." Nucleic Acid. Res. (2007) 35 (2) p. 363-370.*
Laganière, Josee et al; "Functional genomics identifies a mechanism for estrogen activation of the retinoic acid receptor alpha1 gene in breast cancer cells." Mol. Endocrin. (2005) 19(6) p. 1584-1592.*
Herman, David M. et al, "Cycle polyamide motif for recognition of the minor grove of dna." J. Am. Chem. Soc. (1999) 121 p. 1121-1129.*
Melander, Christian et al, "Discrimination of a/t sequences in the minor grove of dna within a cyclic polyamide motif." Chem. Eur. J. (2000) 6(24) p. 4487-4497.*

(Continued)

*Primary Examiner* — Fred Reynolds
(74) *Attorney, Agent, or Firm* — Stahl Law Firm

(57) ABSTRACT

The present invention relates to polyamides capable of inhibiting ARE-, GRE- and ERE-mediated gene regulation in cells. The present invention also relates to polyamides capable of modulating the activity of RNA polymerase II and p53. The invention also relates to methods to treat diseases related to ARE-, GRE- and ERE-mediated gene regulation and to RNA polymerase II and p53 activity.

11 Claims, 60 Drawing Sheets

(56) References Cited

OTHER PUBLICATIONS

Figure 1:
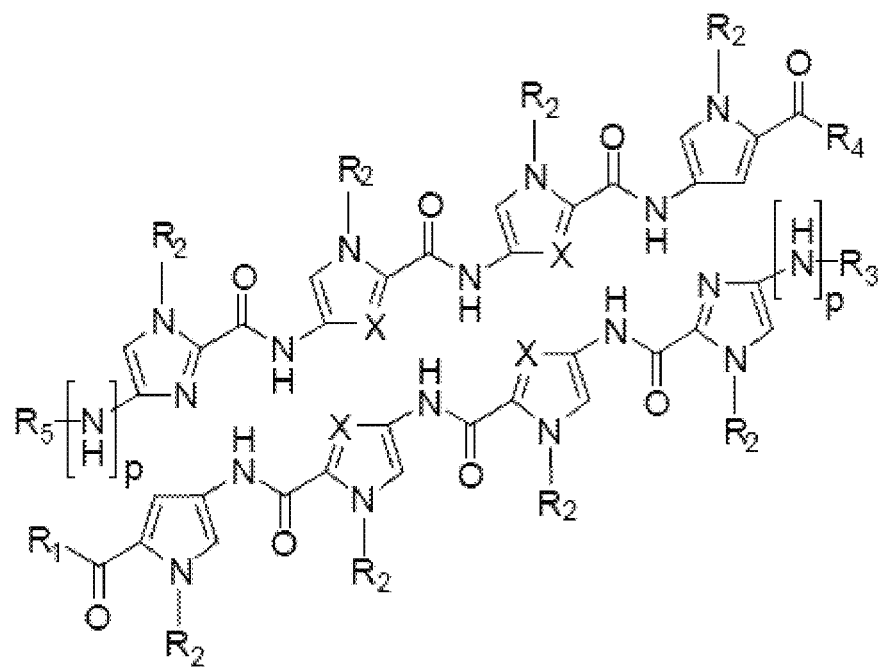

Wurtz, Nicholas R. et al, "Inhibition of dna binding by nf-kb with pyrrole imidazole polyamides." Biochemistry (2002) 41 p. 7604-7609.*
Briehn, Christoph A. et al, "Alternative hetrocycles for dna recognition: the benzimidazole/imidazole pair." Chem. Eur. J. (2003) 9 p. 2110-2122.*
Almarsson et al., 1993, "Molecular mechanics calculations of the structures of polyamide nucleic acid DNA duplexes and triple helical hybrids," Proc. Natl. Acad. Sci. USA 90:7518-7522.
Baird et al., 1996, "Solid Phase Synthesis of Polyamides Containing Imidazole and Pyrrole Amino Acids," J. Am. Chem. Soc. 118:6141-6146.
Best et al., 2003, "Nuclear localization of pyrrole-imidazole polyamide-fluorescein conjugates in cell culture," Proc. Natl. Acad. Sci. USA 100(21):12063-12068.
Burnett et al., 2006, "DNA sequence-specific polyamides alleviate transcription inhibition associated with long GAA•TTC repeats in Friedrich's ataxia," Proc. Natl. Acad. Sci. USA 103(31):11497-11502.
Chen et al., 2004, "Molecular determinants of resistance to antiandrogen therapy," Nature Medicine 10(1):33-39.
Cheng et al., 2006, "Short Hairpin RNA Knockdown of the Androgen Receptor Attenuates Ligand-Independent Activation and Delays Tumor Progressions," Cancer Res. 66(21):10613-10620.
Cherny et al., 1993, "DNA unwinding upon strand-displacement binding of a thymine-substituted polyamide to double-stranded DNA," Proc. Natl. Acad. Sci. USA 90:1667-1670.
Chiang et al., 2000, "Targeting the Ets Binding Site of the HER2/neu Promoter with Pyrrole-Imidazole Polyamides," J. Biol. Chem. 275(32):24246-24254.
Coull et al., 2002, "Targeted Derepression of the Human Immunodeficiency Virus Type 1 Long Terminal Repeat by Pyrrole-Imidazole Polyamides," J. Virology 76(23):12349-12354.
DePrimo et al., 2002, "Transcriptional programs activated by exposure of human prostate cancer cells to androgen," Genome Biology 3(7):re5earch0032.1-0032.12.
Dervan, 2001, "Molecular Recognition of DNA by Small Molecules," Bioorganic & Medicinal Chem. 9:2215-2235.
Dickinson et al., 1998, "Inhibition of RNA polymerase II transcription in human cells by synthetic DNA-binding ligands," Proc. Natl. Acad. Sci. USA 95:12890-12895.
Dickinson et al., 2004, "Arresting Cancer Proliferation by Small-Molecule Gene Regulation," Chemistry & Biology 11: 1583-1594.
Dudouet et al., 2003, "Accessibility of Nuclear Chromatin by DNA Binding Polyamides," Chemistry & Biology 10:859-867.
Edelson et al., 2004, "Influence of structural variation on nuclear localization of DNA-binding polyamde-fluorophore conjugates," Nucleic Acids Res. 32(9):2802-2818.
Ehley et al., 2002, "Promoter Scanning for Transcription Inhibition with DNA-Binding Polyamides," Molecular and Cellular Biology 22(6):1723-1733.
Gottesfeld et al., 2001, "Sequence-specific Recognition of DNA in the Nucleosome by Pyrrole-Imidazole Polyamides," J. Mol. Biol. 309:615-629.
Gupta et al., 2002, "Molecular mechanisms of glucocorticoid action," Current Science 83(9):1103-1111.
Gygi et al., 2002, "Use of fluorescent sequence-specific polyamides to discriminate human chromosomes by microscopy and flow cytometry," Nucleic Acids Res. 30(13):2790-2799.
Holzbeierlein et al., "Gene Expression Analysis of Human Prostate Carcinoma during Hormonal Therapy Identifies Androgen-Responsive Genes and Mechanisms of Therapy Resistance," Am. J. of Pathology 164(1):217-227, 2004.
Hsu et al., 2007, "Completion of a Programmable DNA-Binding Small Molecule Library," Tetrahedron 63(27):6146-6151.
Hurley, 2002, "DNA and its associated processes as targets for cancer therapy," Nature Reviews 2:188-200.
Isaacs et al., 2004, "Androgen receptor outwits prostate cancer drugs," Nature Medicine 10(1):26-27.

Kelly et al., 1996, "Binding site size limit of the 2:1 pyrrole-imidazole polyamide-DNA motif," Proc. Natl. Acad. Sci. USA 93:6981-6985.
Klein et al., 1997, "Progression of metastatic human prostate cancer to androgen independence in immunodeficient SCID mice," Nature Medicine 3(4):402-408.
Lacy et al., 2002, "Recognition of T•G mismatched base pairs in DNA by stacked imidazole-containing polyamides: surface plasmon resonance and circular dichroism studies," Nucleic Acids Res. 30(8):1834-1841.
Lacy et al., 2004, "Energetic basis for selective recognition of T•G mismatched base pairs in DNA by imidazole-rich polyamides," Nucleic Acids Res. 32(6):2000-2007.
Marques et al., 2002, "Toward an Understanding of the Chemical Etiology for DNA Minor-Groove Recognition by Polyamides," Helvetica Chimica Acta 85:4485-4517.
Massie et al., 2007, "New androgen receptor genomic targets show an interaction with the ETS1 transcription factor," EMBO reports 8(9):871-878.
McGinley etal., 2007, "Circumventing Anti-Androgen Resistance by Molecular Design," J. Am. Chem. Soc.
Melander et al., 2004, "Regulation of gene expression with pyrrole-imidazole polyamides," J. Biotechnology 112:195-220.
Neamati et al., 1998, "Highly Potent Synthetic Polyamides, Bisdistamycins, and Lexitropsins as Inhibitors of Human Immunodeficiency Virus Type 1 Integrase," Molecular Pharmacology 54:280-290.
Nelson et al., 2003, "Prostate Cancer," N. Eng. J. Med. 349(4):366-381.
Nickols et al., 2006, "Improved nuclear localization of DNA-binding polyamides," Nucleic Acids Res. 35(2):363-370.
Nickols et al., 2007, "Modulating Hypoxia-Inducible Transcription by Disrupting the HF-1-DNA Interface," ACS Chemical Biology 2(8):561-571.
Nickols et al., 2007, "Suppression of androgen receptor-mediated gene expression by a sequence-specific DNA-binding polyamide," Proc. Natl. Acad. Sci. USA 104(25):10418-10423.
Norgaard et al., 1991, "Glucocorticoid receptors in human malignancies: A review," Annals of Oncology 2:541-557.
O'Hare et al., "DNA sequence recognition in the minor groove by crosslinked polyamides: The effect of N-terminal head group and linker length on binding affinity and specificity," Proc. Natl. Acad. Sci. USA 99(1):72-77, 2002.
Olenyuk et al., 2004, "Inhibition of vascular endothelial growth factor with a sequence-specific hypoxia response element antagonist," Proc. Natl. Acad. Sci. USA 101(48):16768-16773.
Philips et al., 2005, "DNA Damage Effects of a Polyamide-CBI Conjugate in SV40 Virions," Mol. Pharmacol. 67:877-882.
Pilch et al., 1996, "Binding of a hairpin polyamide in the minor groove of DNA: Sequence-specific enthalpic discrimination," Proc. Natl. Acad. Sci. USA 93:8306-8311.
Rosen et al., 2005, "The Search for Safer Glucocorticoid Receptor Ligands," Endocrine Reviews 26(3):452-464.
Sazani et al., 2001, "Nuclear antisense effects of neutral, anionic and cationic oligonucleotide analogs," Nucleic Acids Res. 29(19):3965-3974.
Schaal et al., 2003, "Inhibition of human papilloma virus E2 DNA binding protein by covalently linked polyamides," Nucleic Acids Res. 31(4):1282-1291.
Scher et al., 2005, "Biology of Progressive, Castration-Resistant Prostate Cancer: Directed Therapies Targeting the Androgen-Receptor Signaling Axis," J. Clin. Oncol. 23(32):8253-8261.
Sharifi et al., 2006, "Androgen Receptor as a Therapeutic Target for Androgen Independent Prostate Cancer," Am. J. Therapeutics 13:166-170.
Tomlins et al., 2005, "Recurrent Fusion of *TMPRSS2* and ETS Transcription Factor Genes in Prostate Cancer," Science 310:644-648.
Tomlins et al., 2006, "*TMPRSS2:ETV4* Gene Fusions Define a Third Molecular Subtype of Prostate Cancer," Cancer Res. 66(7):3396-3400.

(56) References Cited

OTHER PUBLICATIONS

Trauger et al., 1996, "Extension of Sequence-Specific Recognition in the Minor Groove of DNA by Pyrrole-Imidazole Polyamides to 9-13 Base Pairs," J. Am. Chem. Soc. 118:6160-6166.
Tsai et al., 2006, "Unanticipated differences between α- and γ-diaminobutyric acid-linked hairpin polyamide-alkylator conjugates," Nucleic Acids Res. 35(1):307-316.
Urbach et al., 2001, "Toward rules for 1:1 polyamide:DNA recognition," Proc. Natl. Acad. Sci. USA 98(8):4343-4348.
Urbach et al., 2002, "Structure of a β-Alanine-linked Polyamide Bound to a Full Helical Turn of Purine Tract DNA in the 1:1 Motif," J. Mol. Biol. 320:55-71.
Wang et al., 2003, "DNA crosslinking and biological activity of a hairpin polyamide-chlorambucil conjugate," Nucleic Acids Res. 31(4):1208-1215.
Warren et al., 2006, "Defining the sequence-recognition profile of DNA-binding molecules," Proc. Natl. Acad. Sci. USA 103(4):867-872.
White et al., 1996, "Effects of the A•T/T•A Degeneracy of Pyrrole-Imidazole Polyamide Recognition in the Minor Groove of DNA," Biochemistry 35:12532-12537.
Wurtz et al., 2002, "Inhibition of DNA Binding by NF-κB with Pyrrole-Imidazole Polyamides," Biochemistry 41:7604-7609.

\* cited by examiner

2: 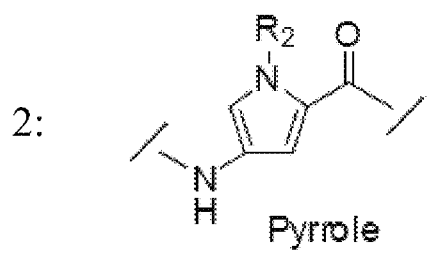 Pyrrole
3: 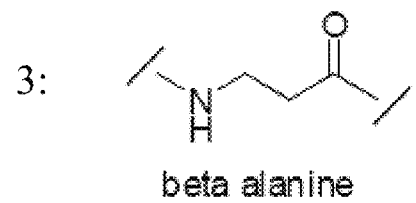 beta alanine
4: 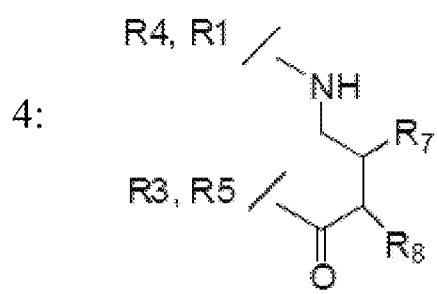
5: 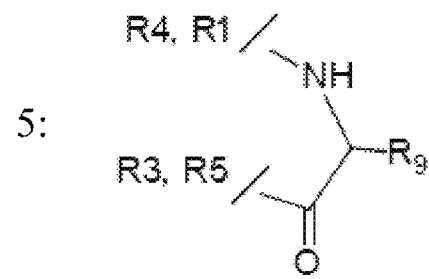
6: 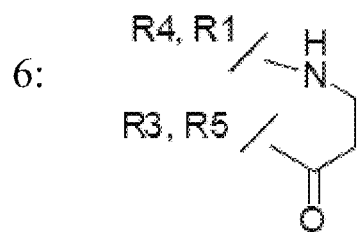
FIGURE 2A 7:  8: 
9:  10: 
11: 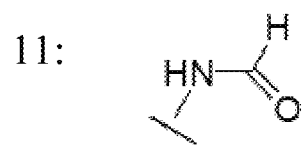 12: 
13: 
14: 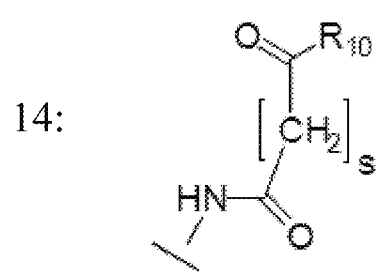 15: 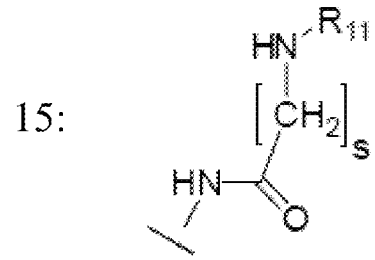
16: 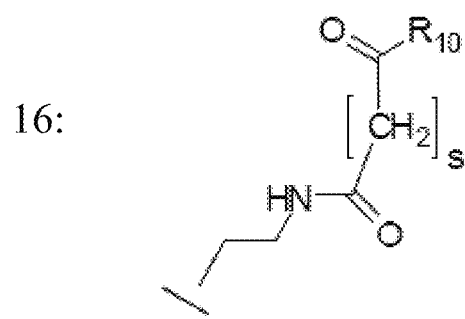 17: 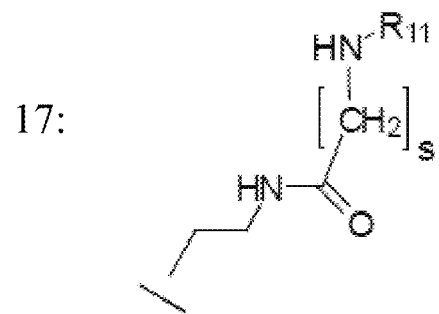
FIGURE 2B

18: 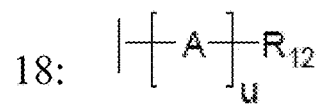    19: 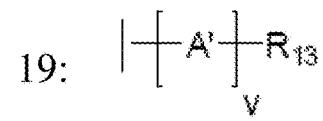
20: 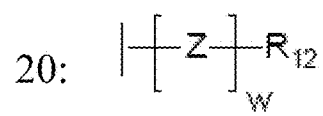
21: 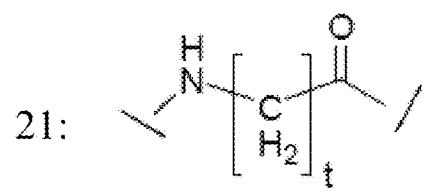    22: 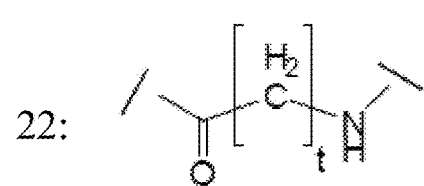
23: 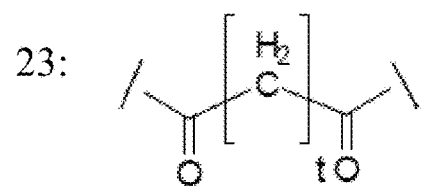
24: 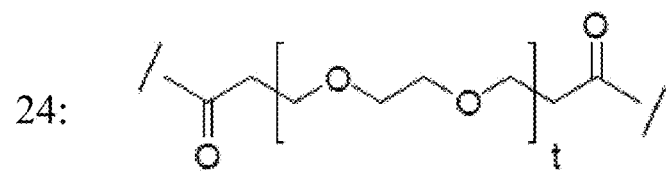
FIGURE 2C 25:   26: 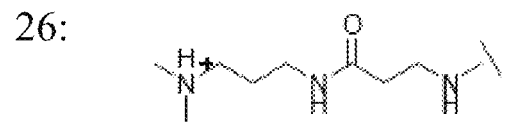
27:   28: 
29:   30: 
31:   32: 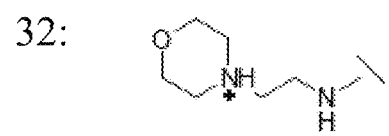
33:   34: 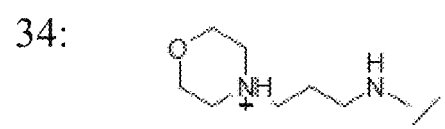
35: 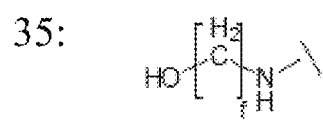  36: 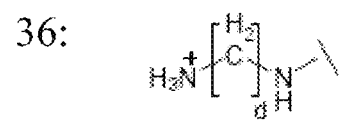
37:   38: 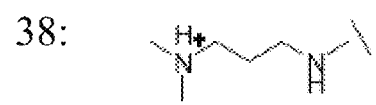
39: 
FIGURE 3A 58: 
59: 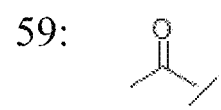
60: 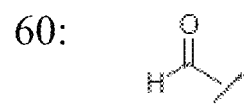
61: 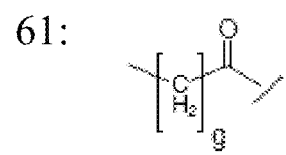
62: 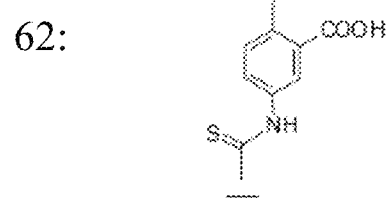
63: 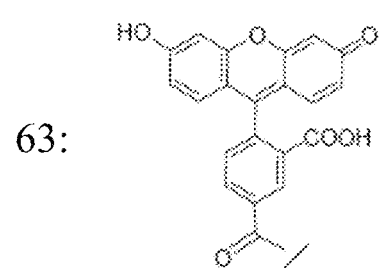
64: 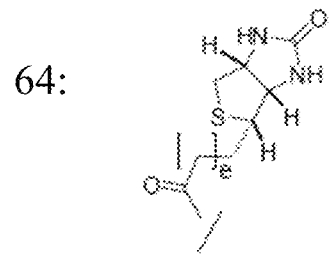
65: 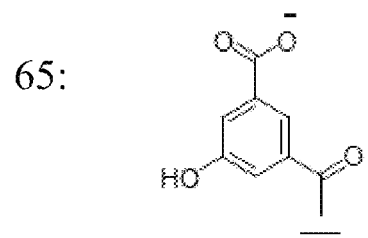
66: 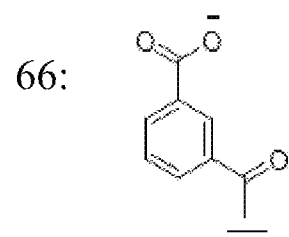
67: 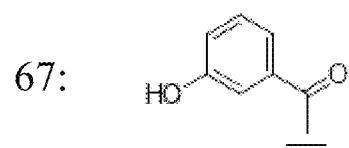
68: 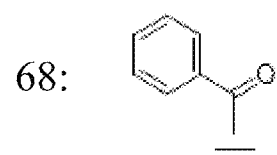
FIGURE 3D

69: 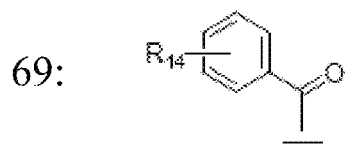   70: 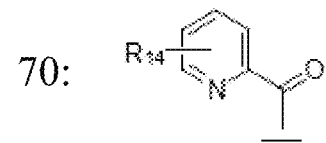
71: 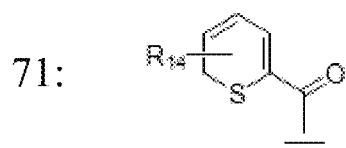   72: 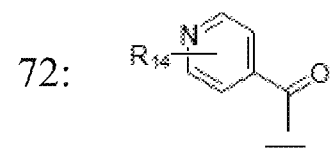
73: 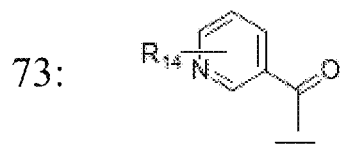   74: 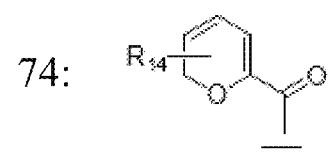
75: 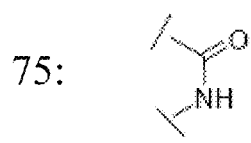   76: 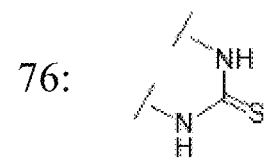
FIGURE 3E A:
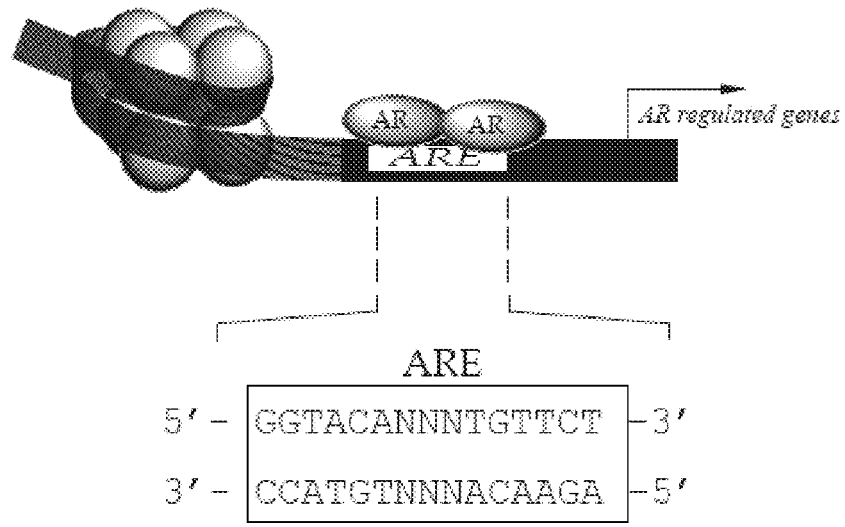
B:
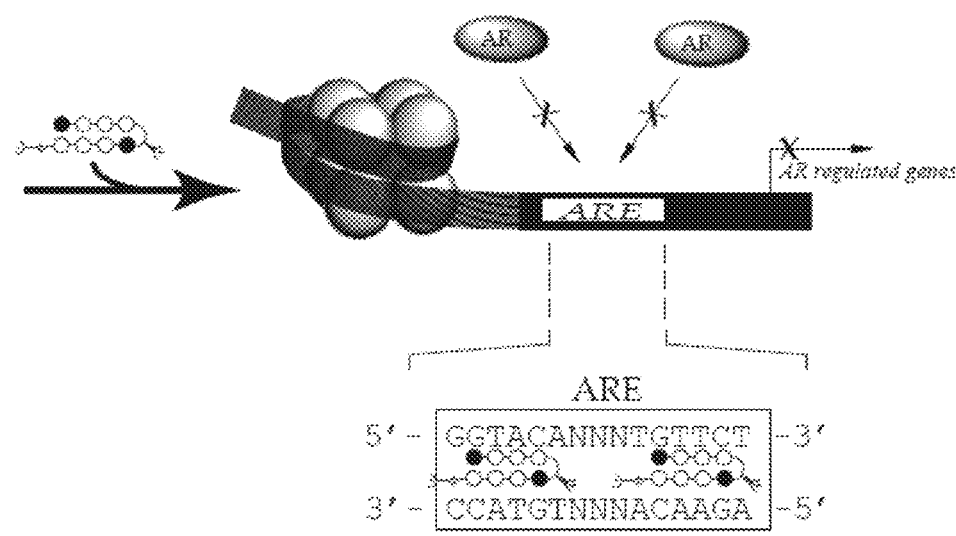
FIGURE 6A-B A
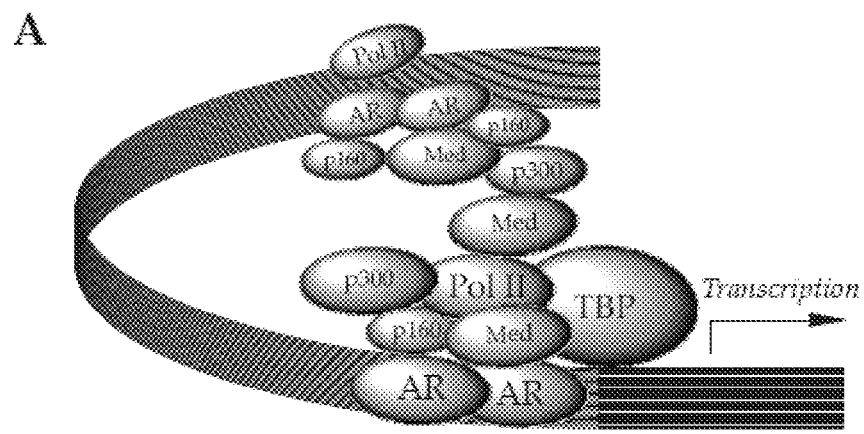
B        Consensus ARE
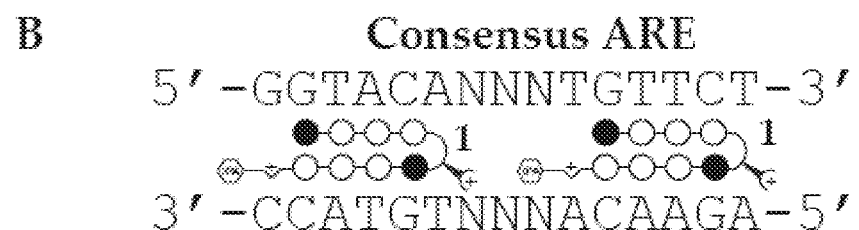
C
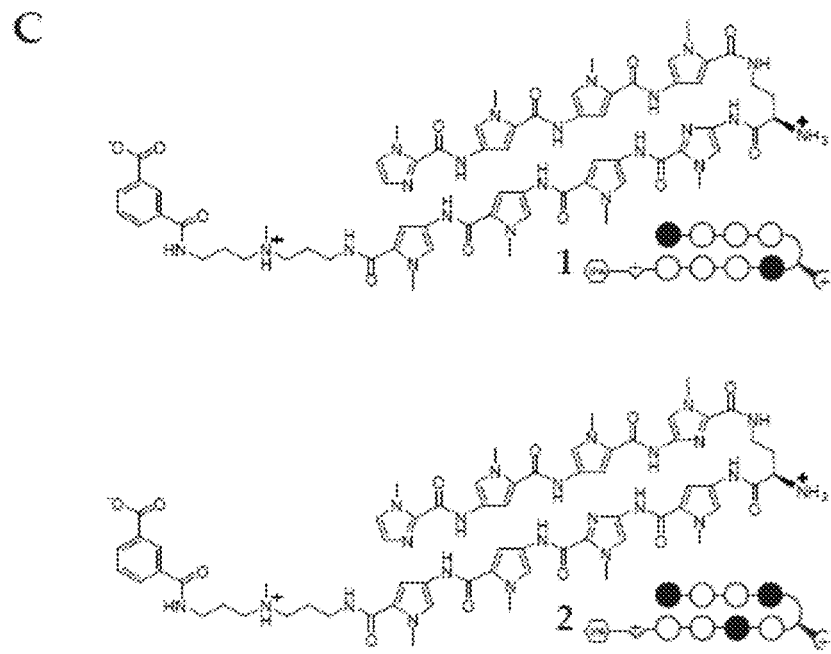
FIGURE 7A-C

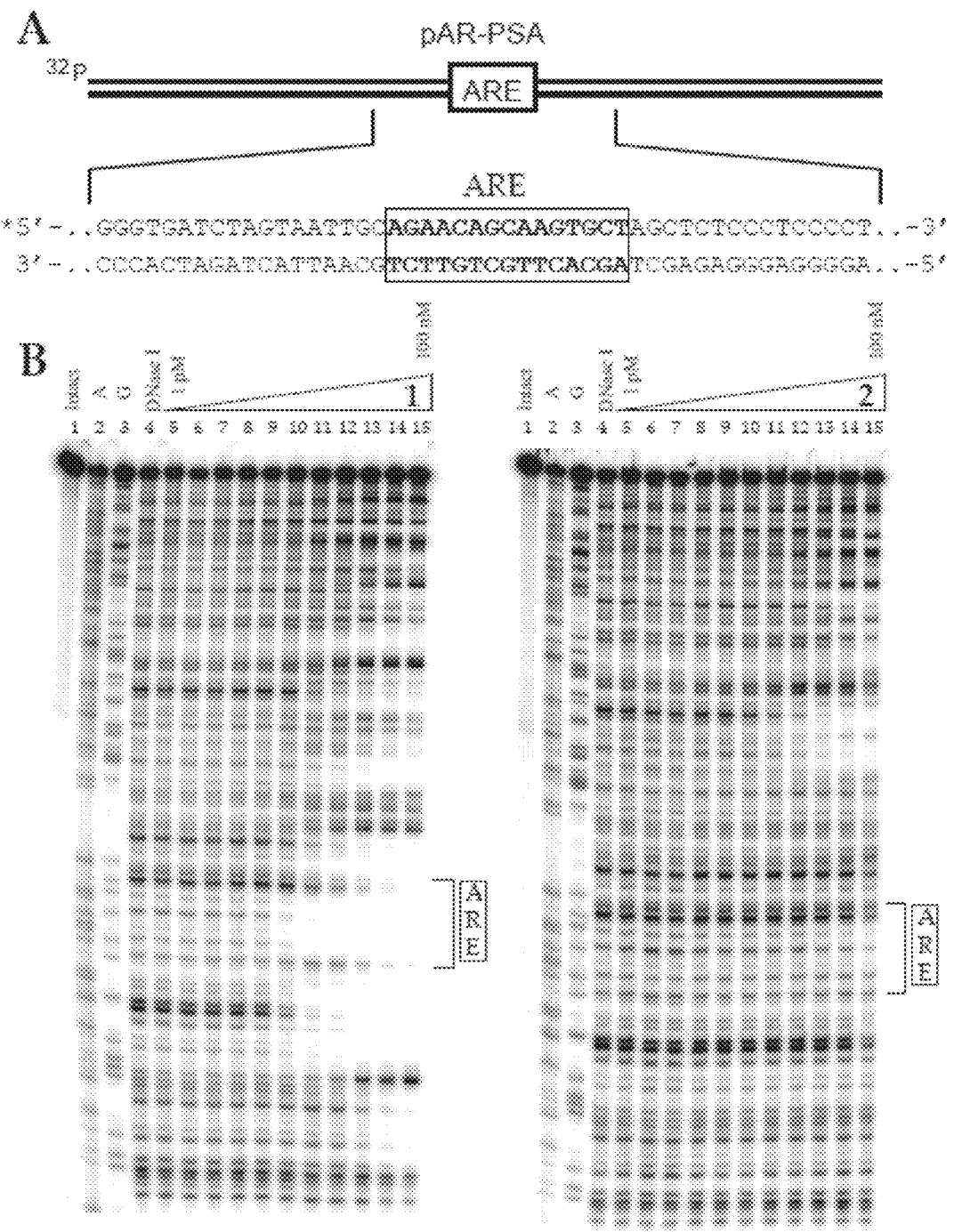
FIGURE 8A-B

C
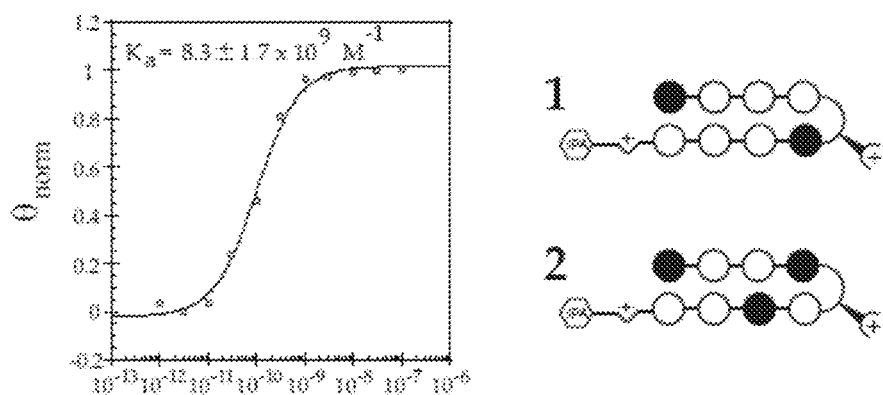
D
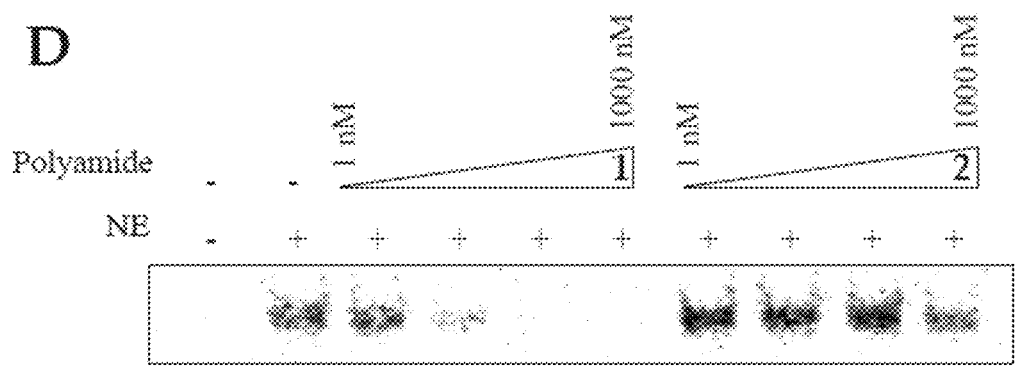
FIGURE 8C-D

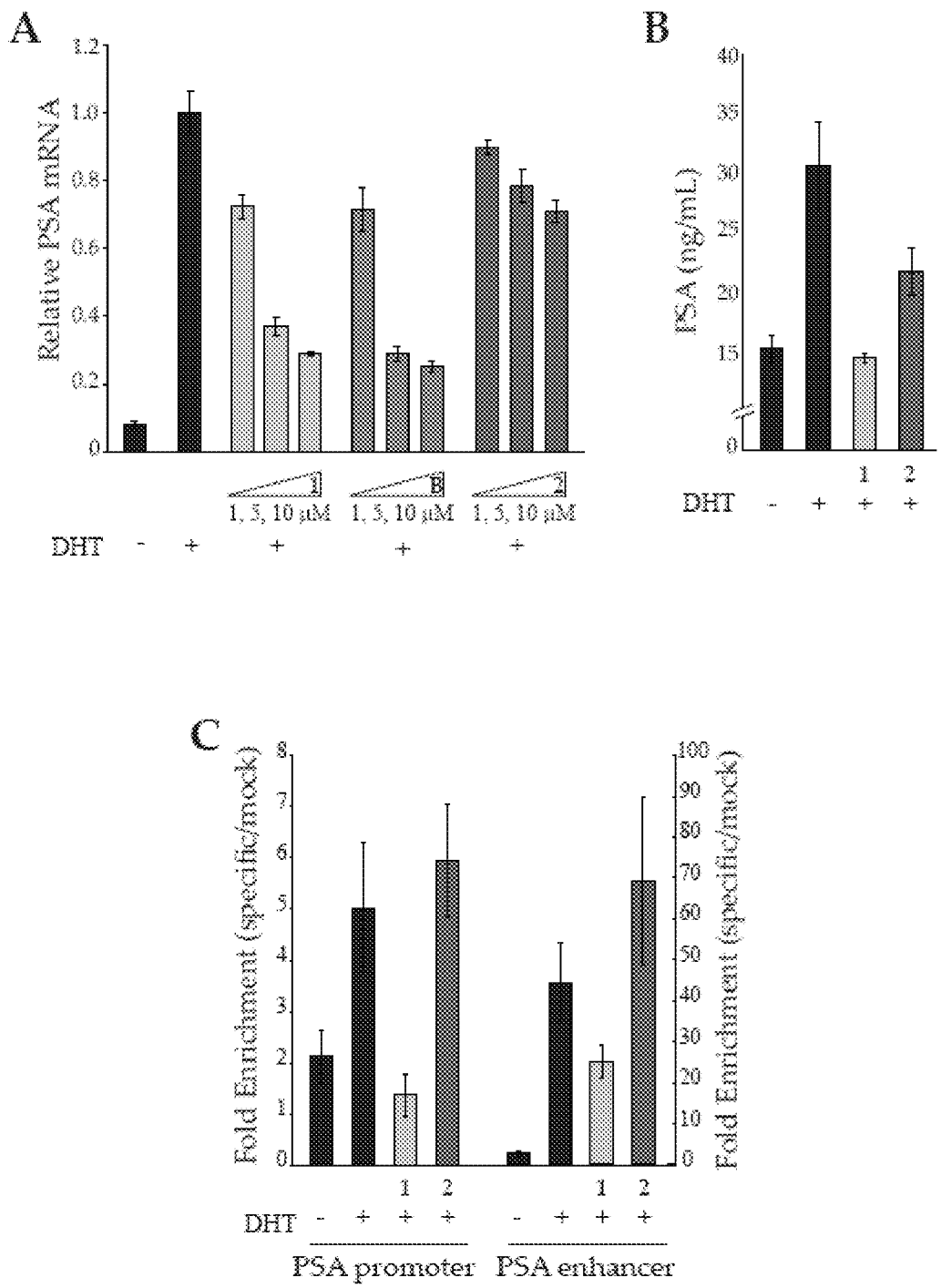
FIGURE 9A-C

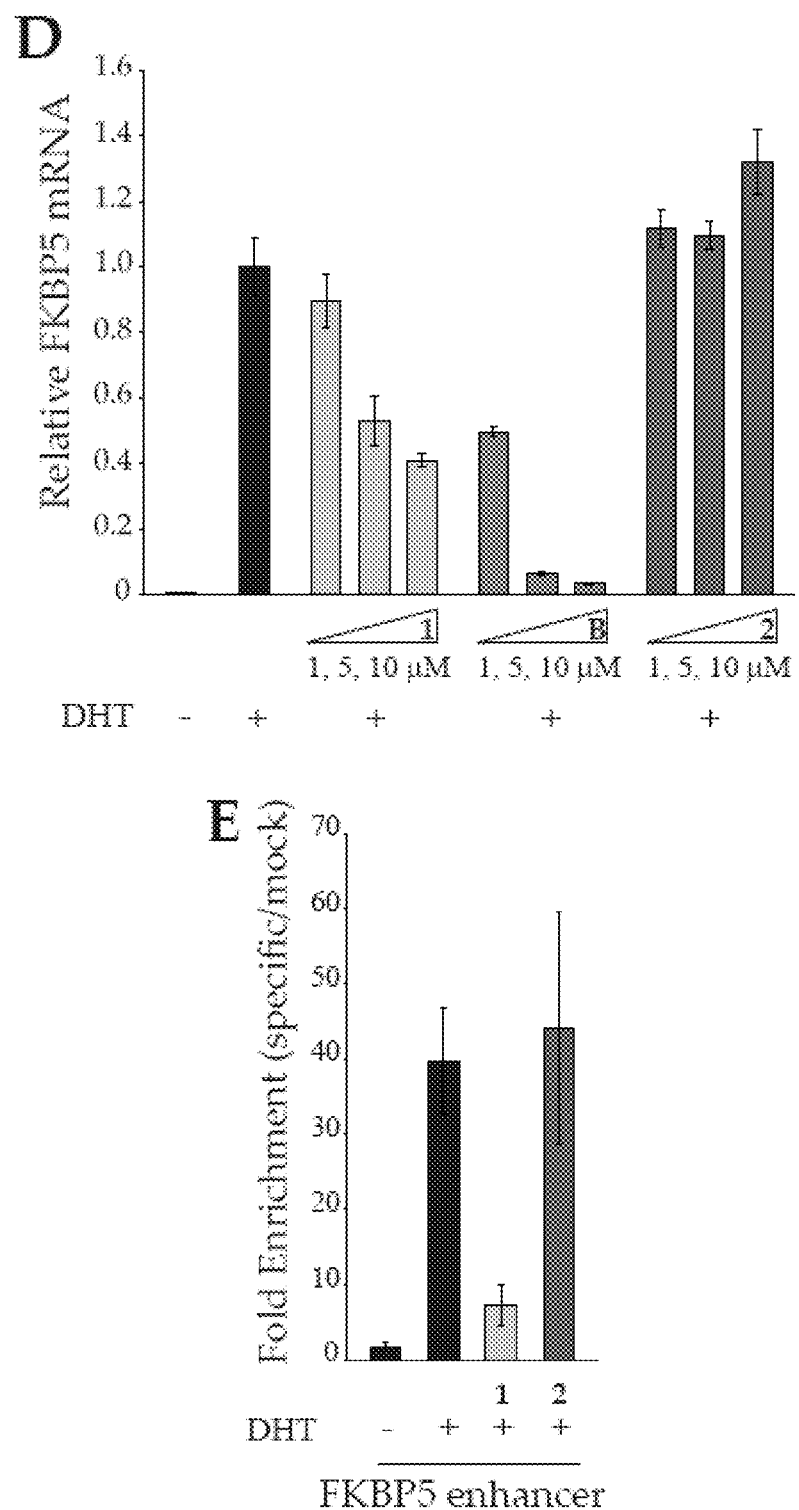
FIGURE 9D-E

B
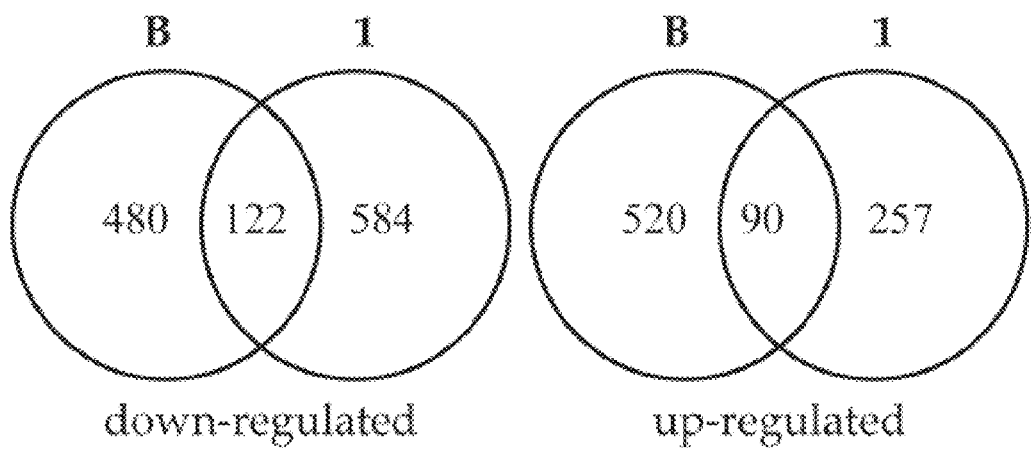
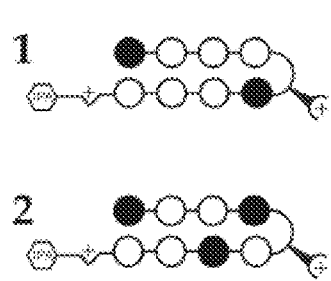
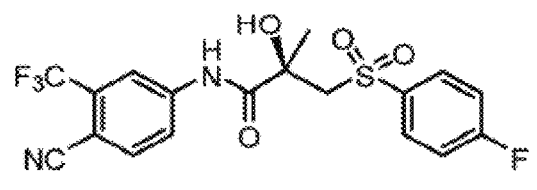
bicalutamide (*Casodex*)
FIGURE 10B

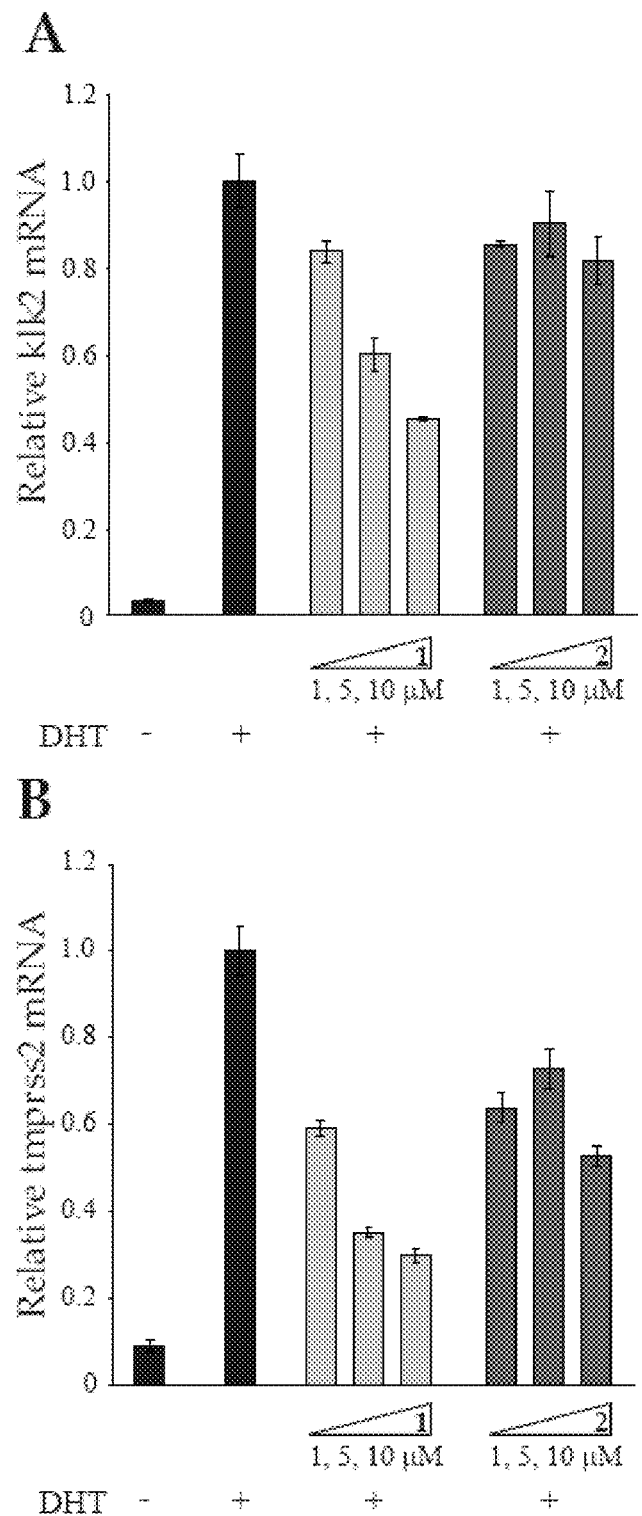
FIGURE 11A-B

Figure 12A:
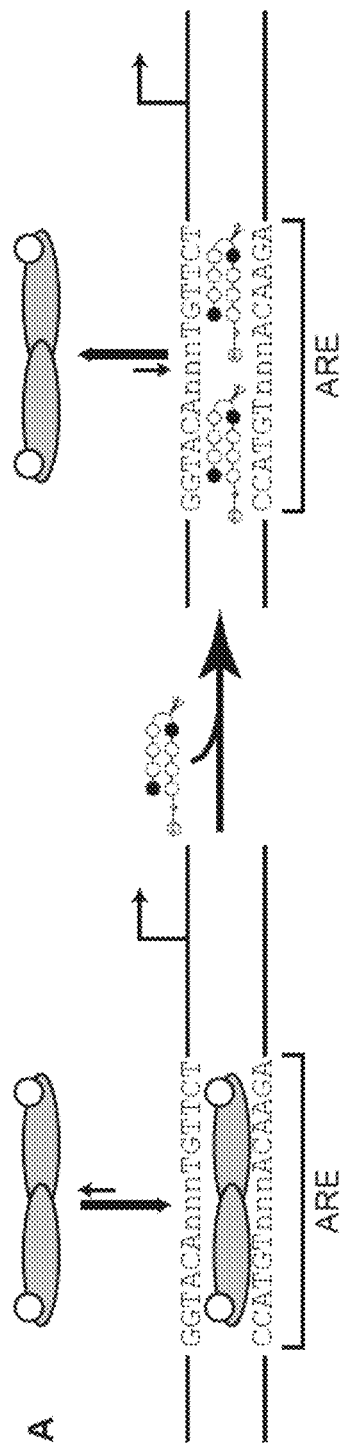

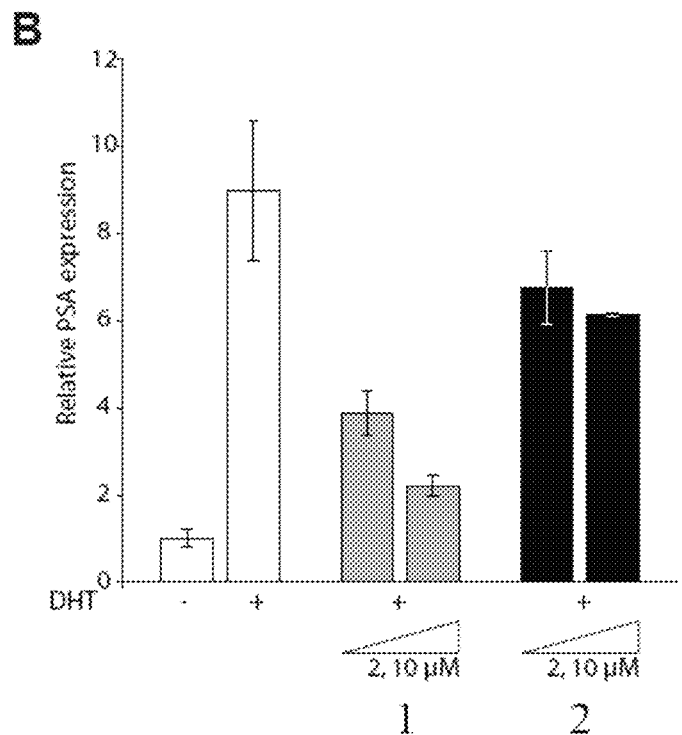
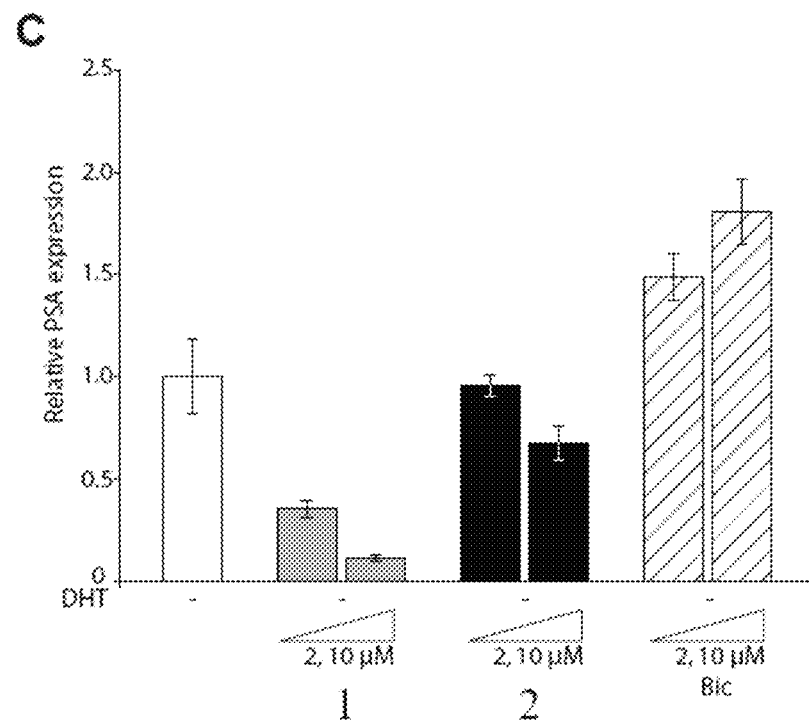
FIGURE 12B-C

Figure 13A:
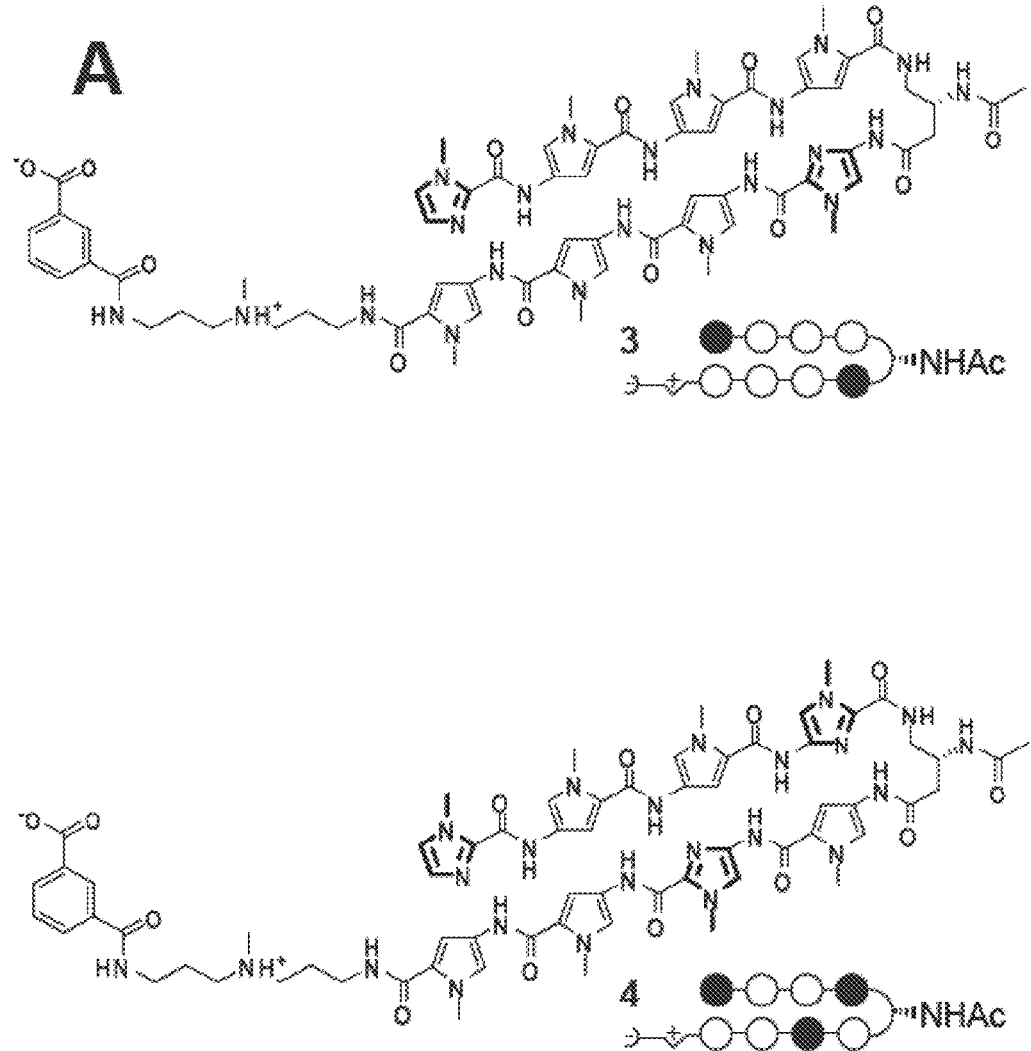

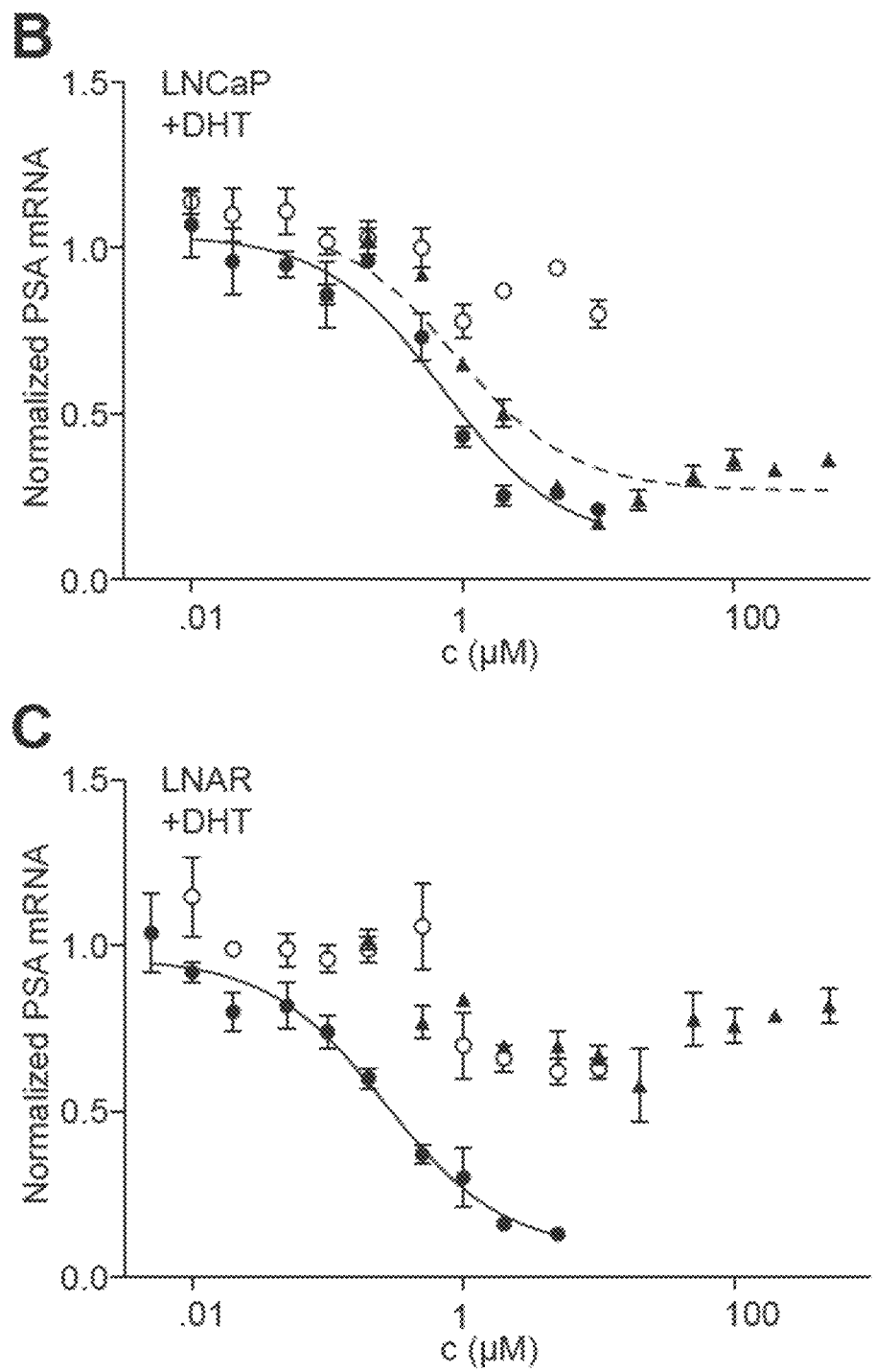
FIGURE 13B-C

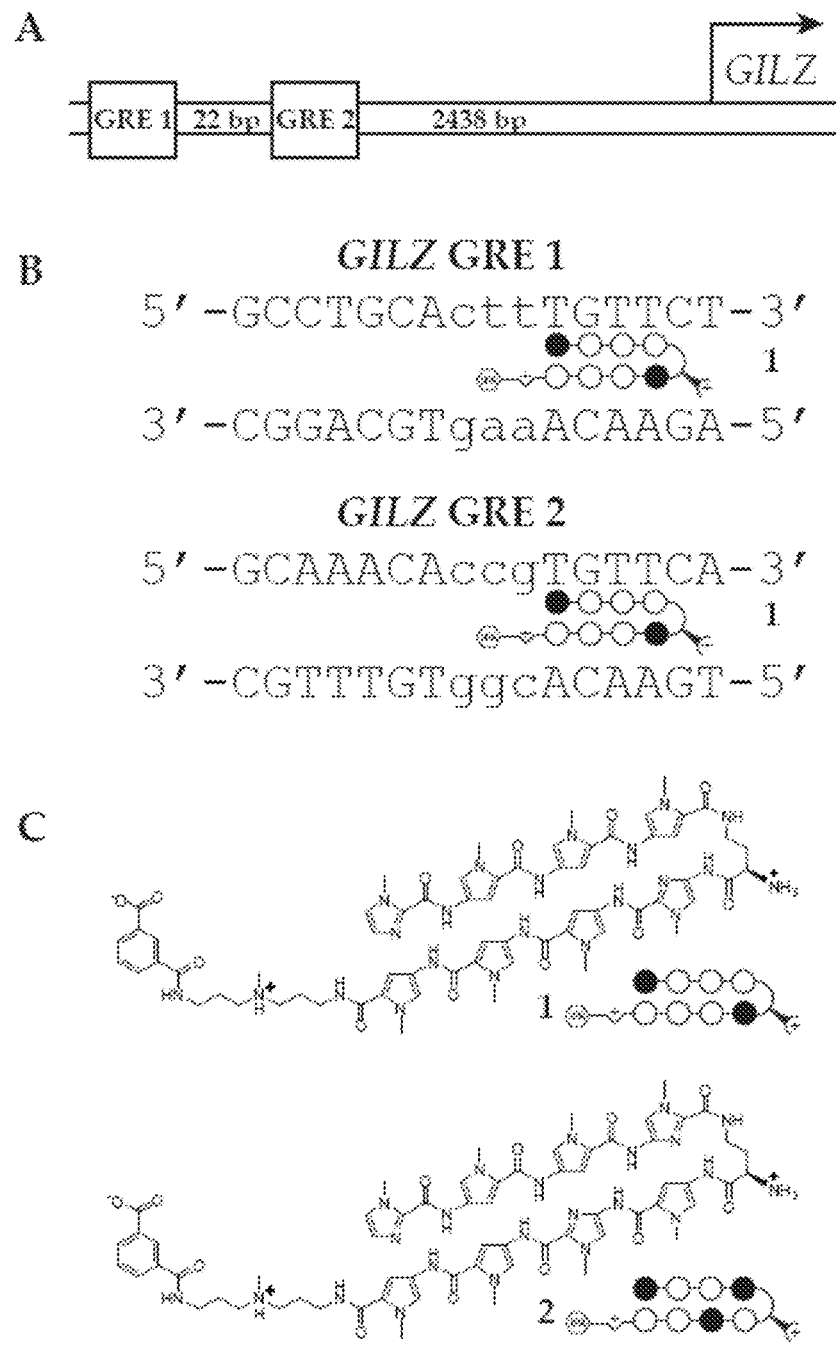
FIGURE 15A-C

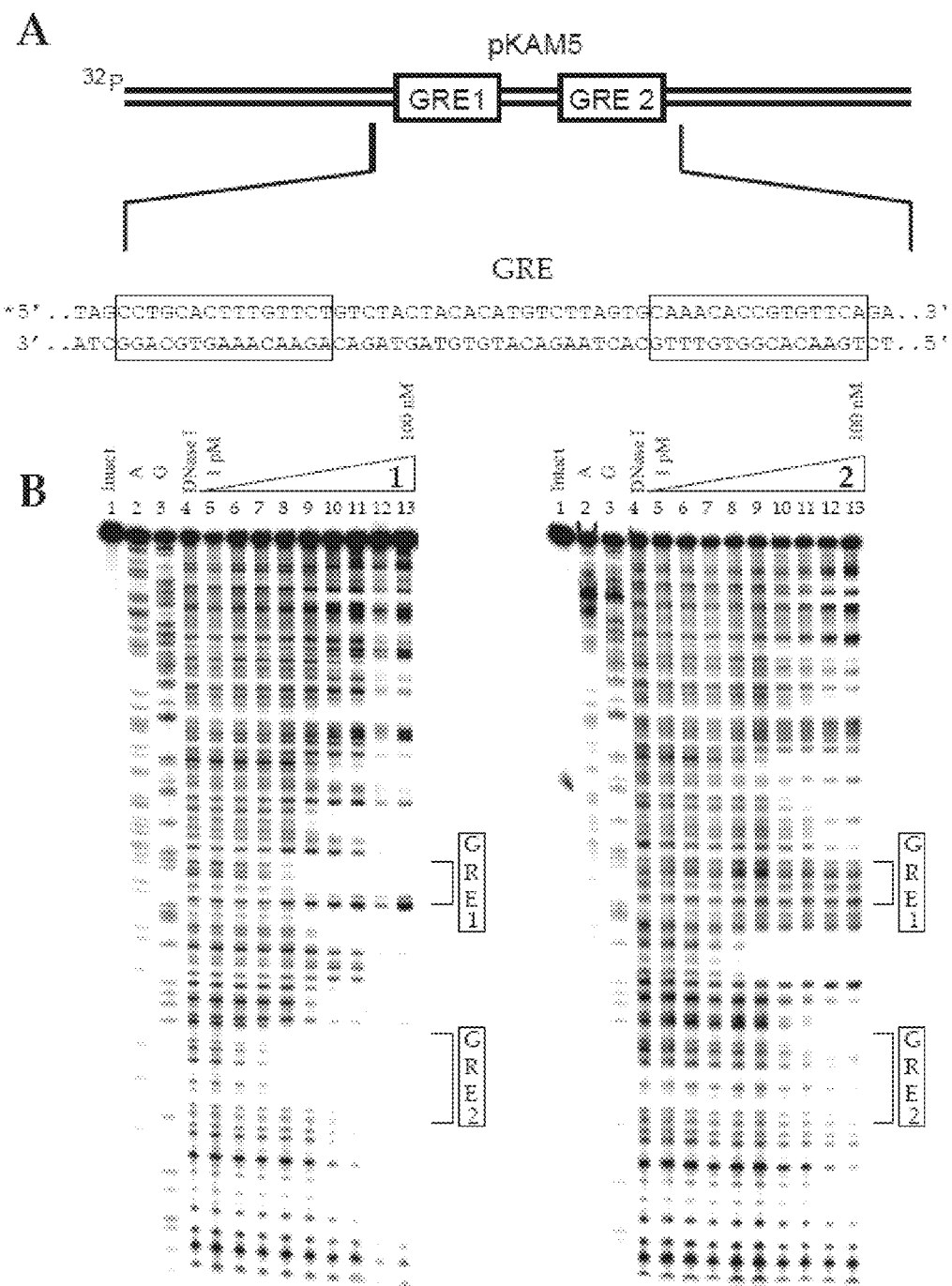
FIGURE 16A-B

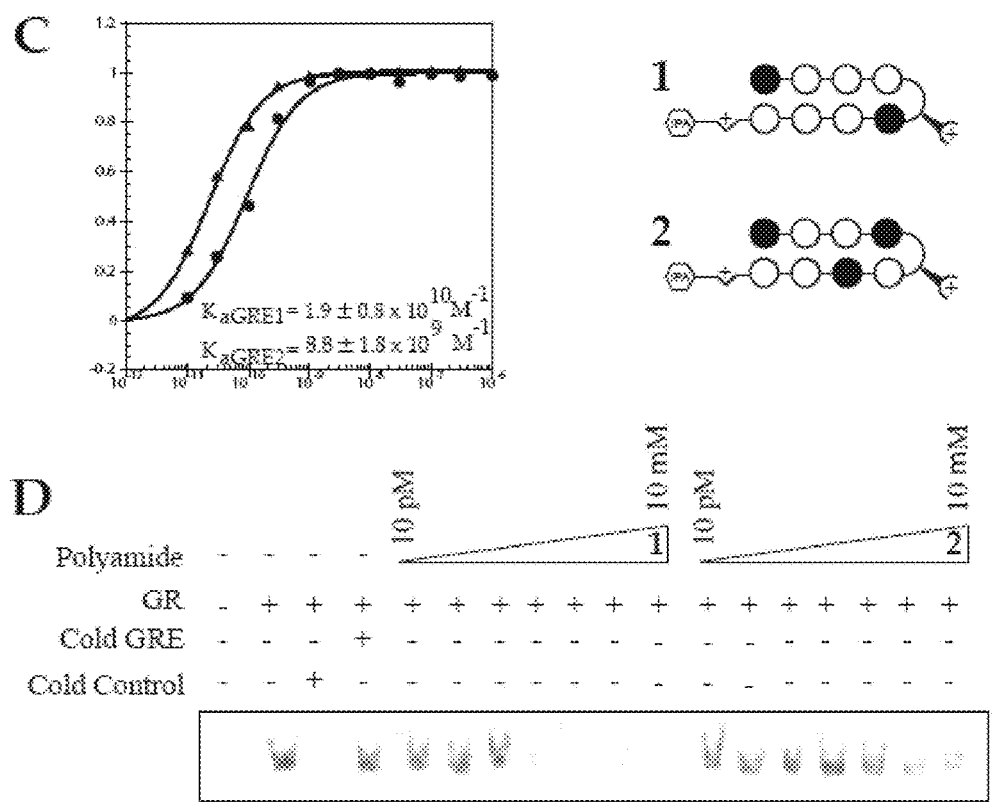
FIGURE 16C-D

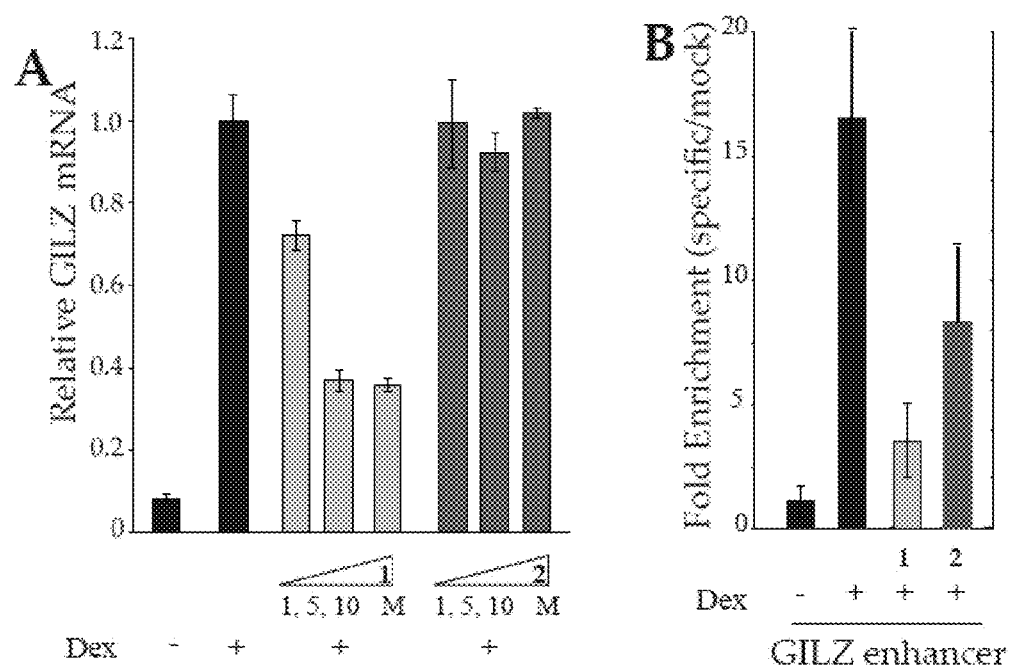
FIGURE 17A-B

A:
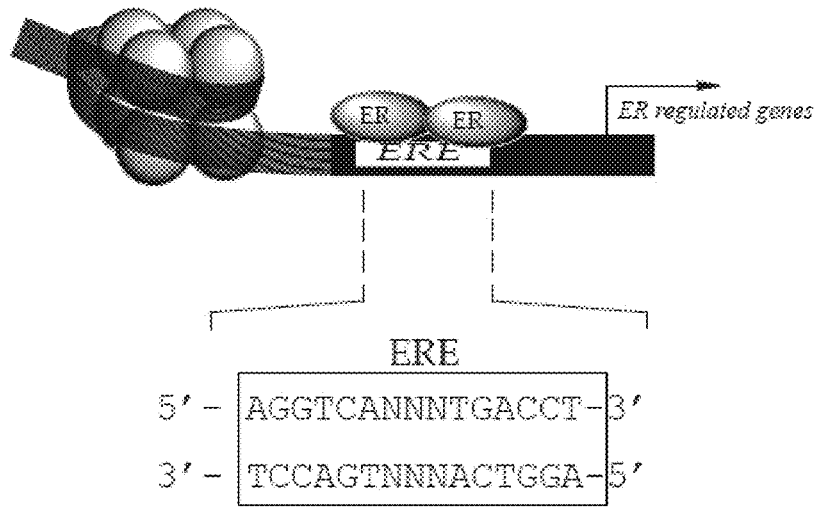
B:
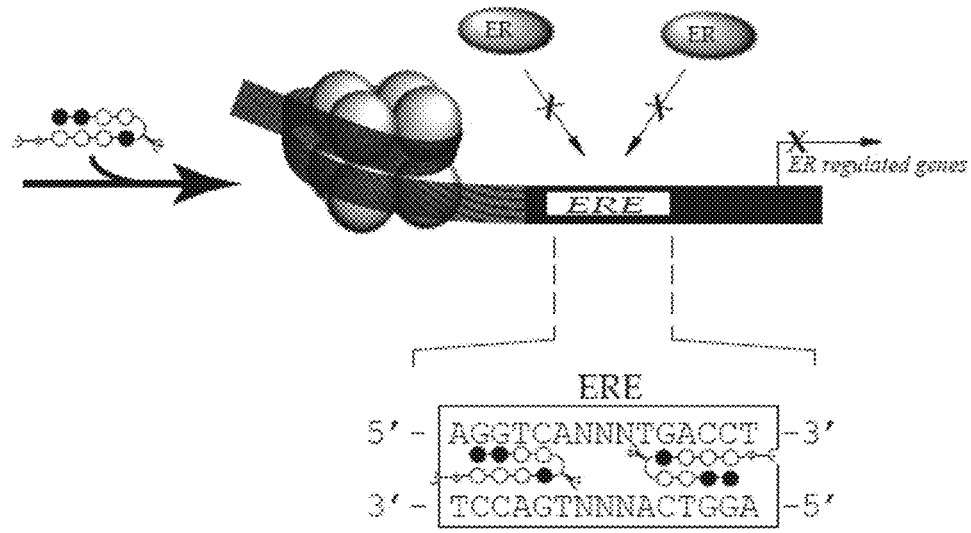
FIGURE 18A-B

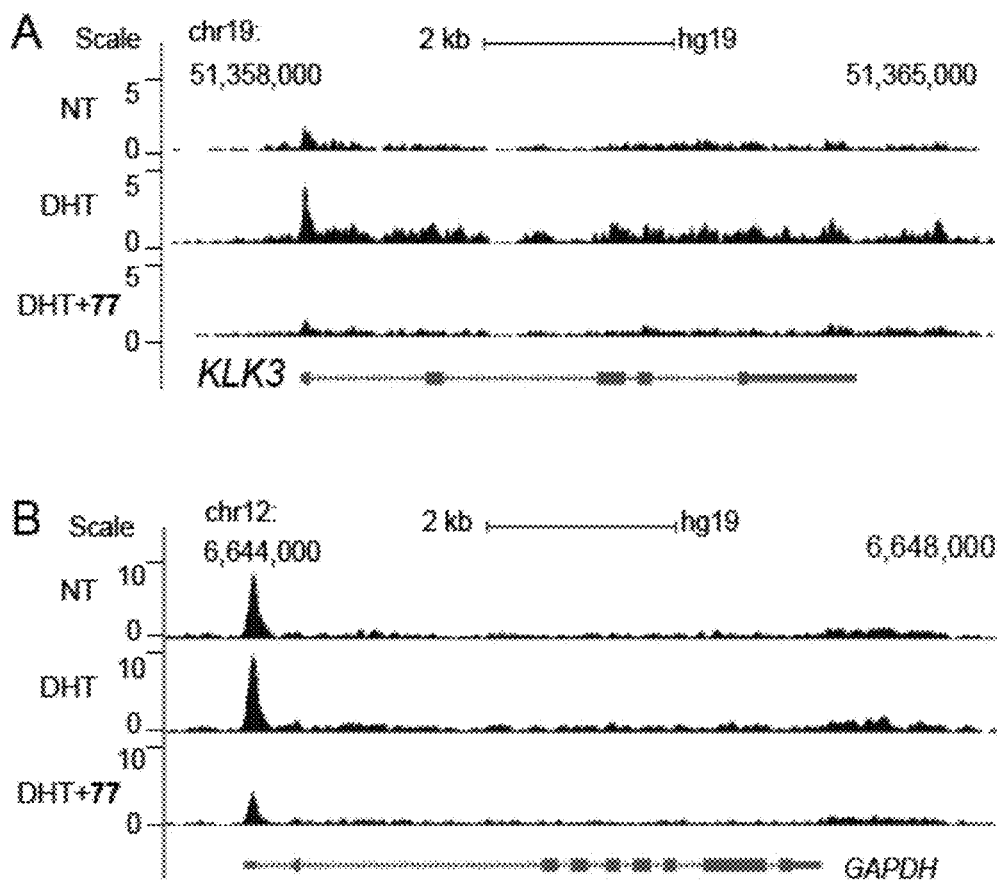
FIGURE 20 A-B

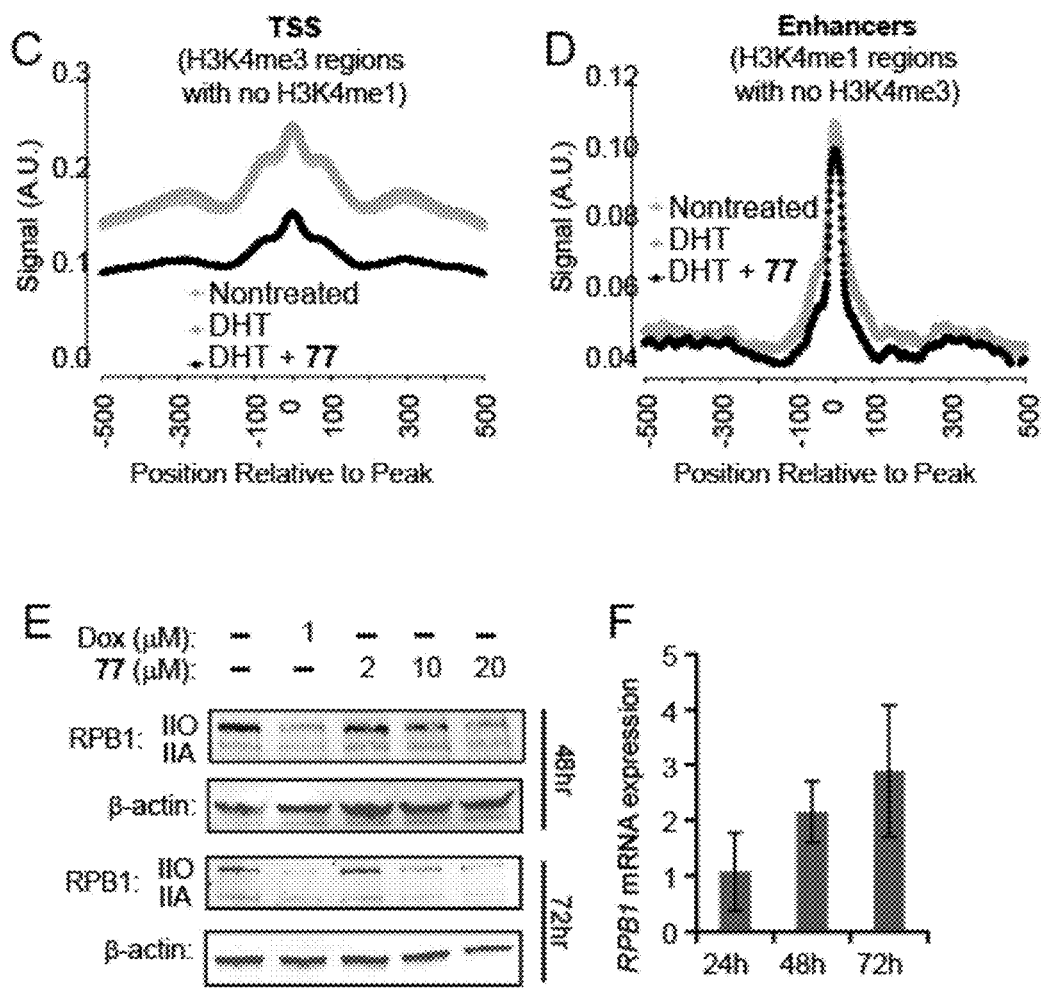
FIGURE 20 C-F

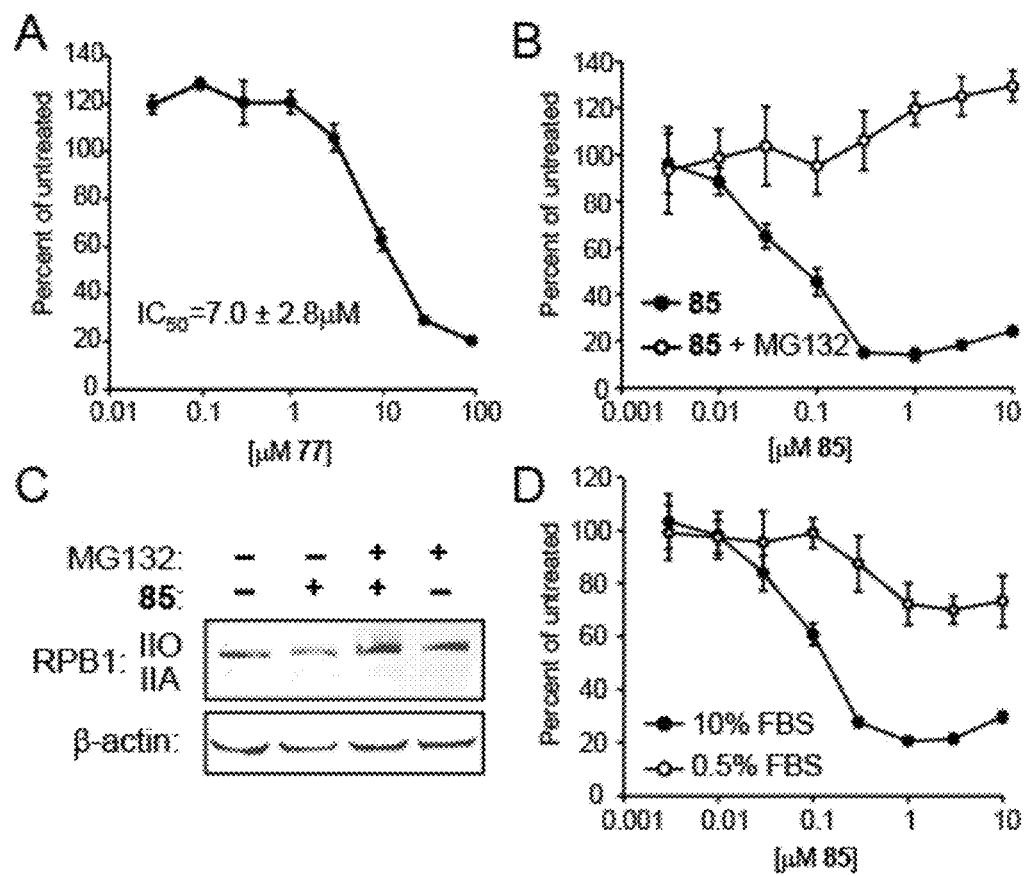
FIGURE 21 A-D

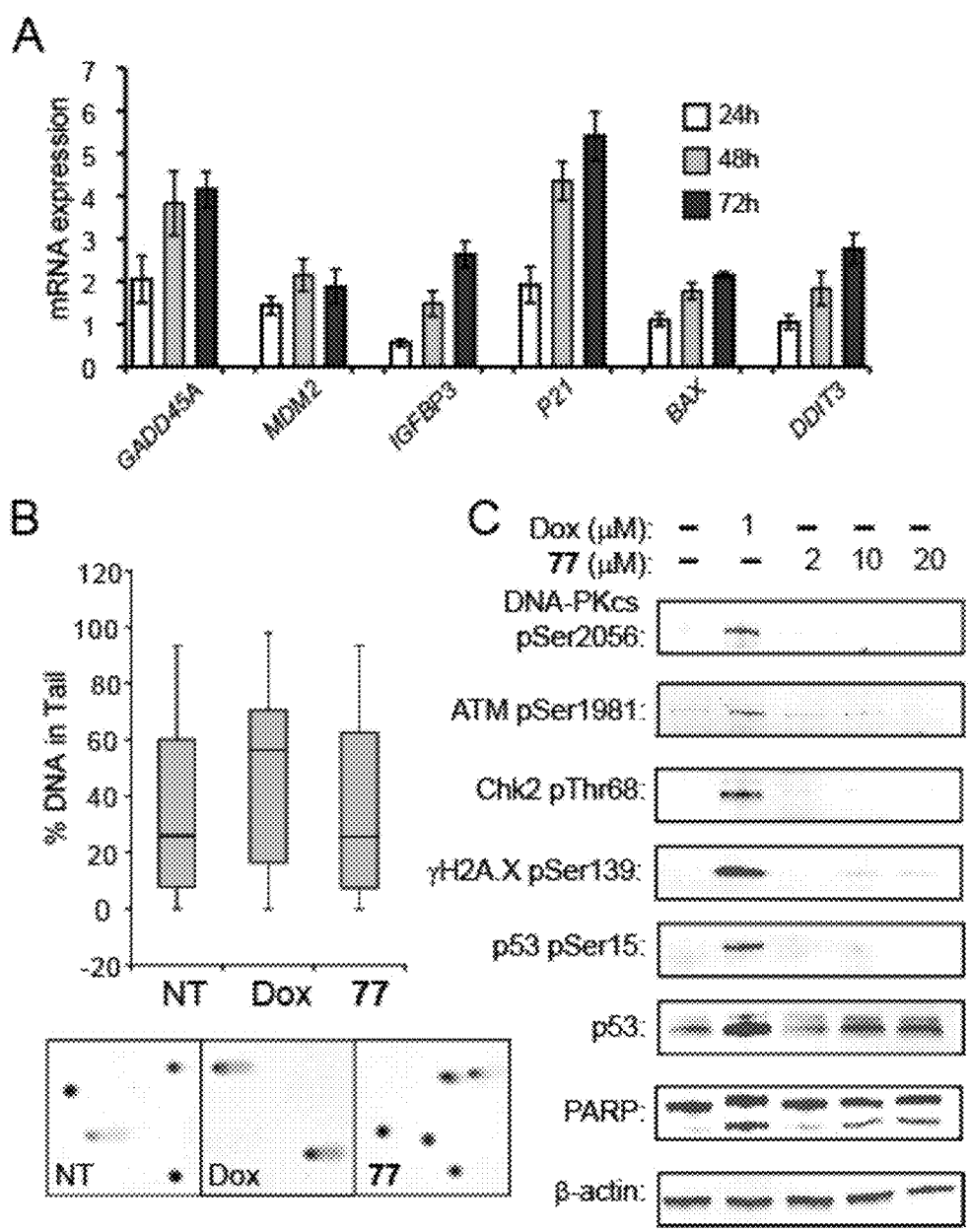
FIGURE 22 A-C

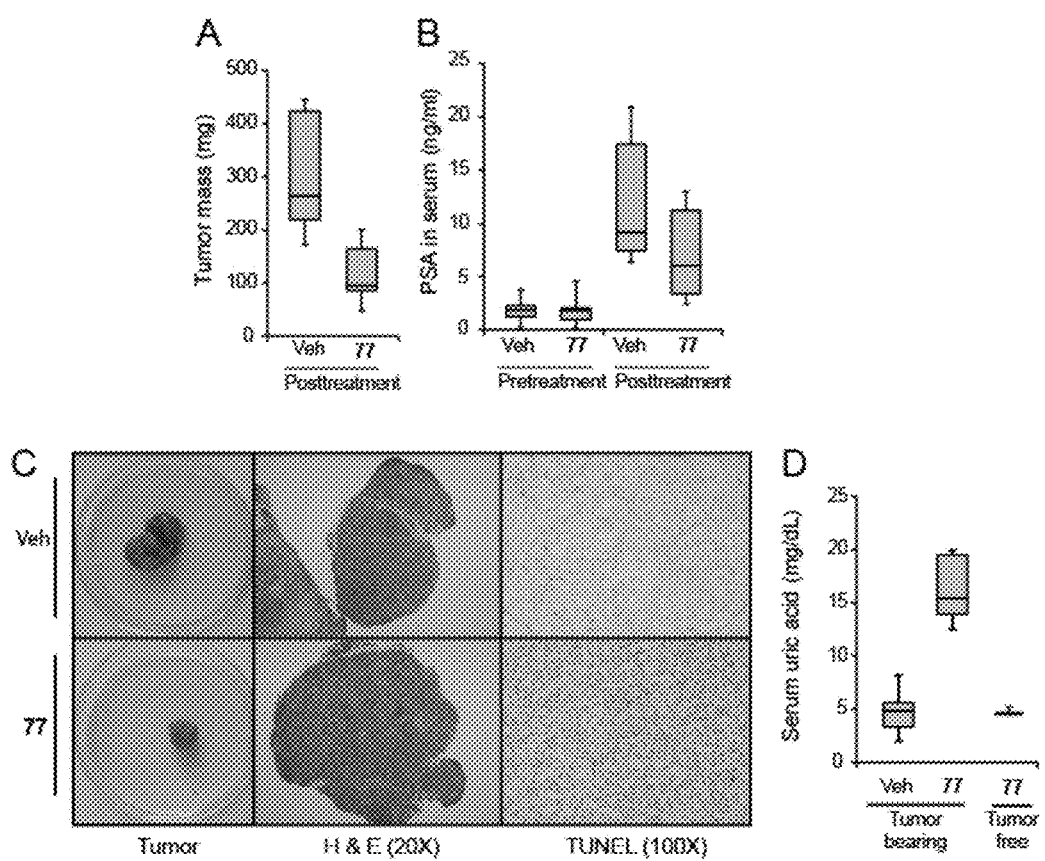
FIGURE 23 A-D

A
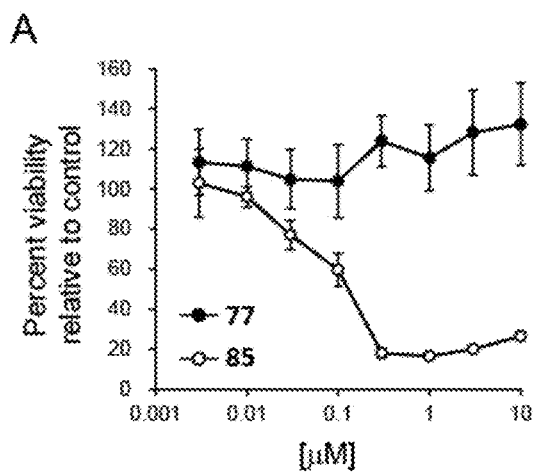
B
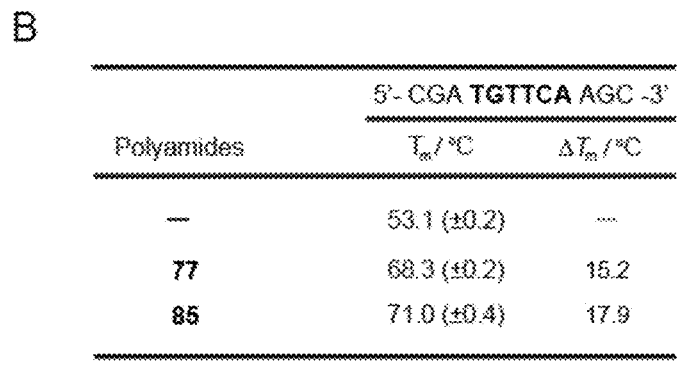
C
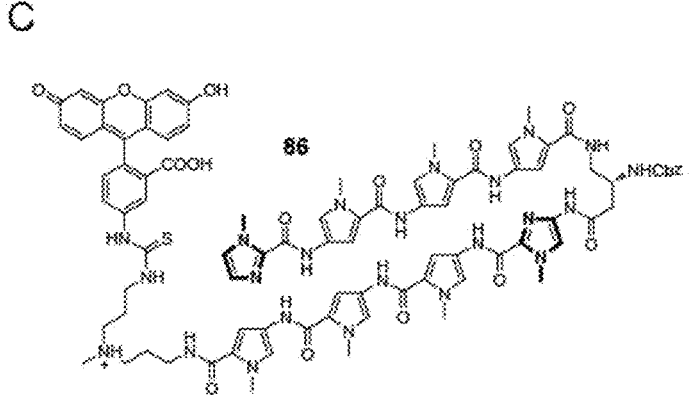
FIGURE 25 A-C

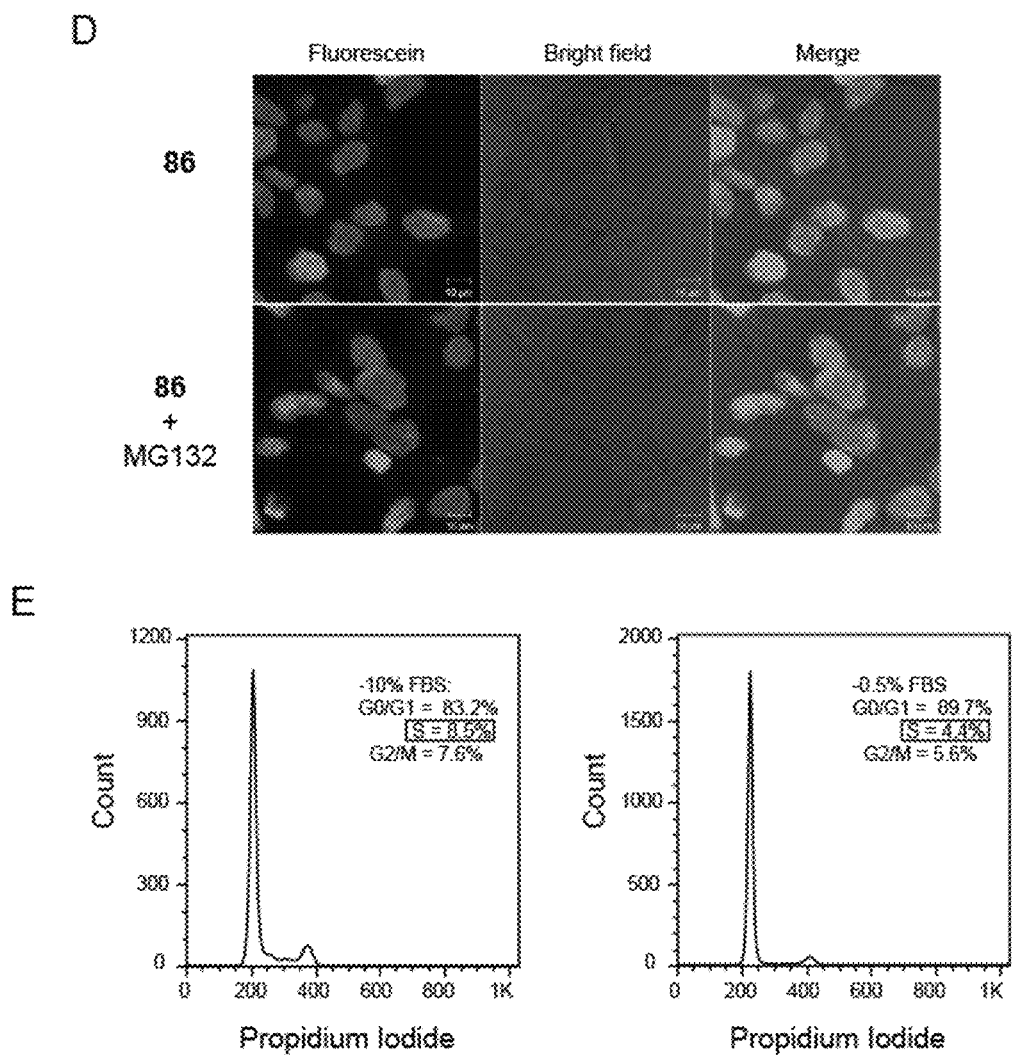
FIGURE 25 D-E

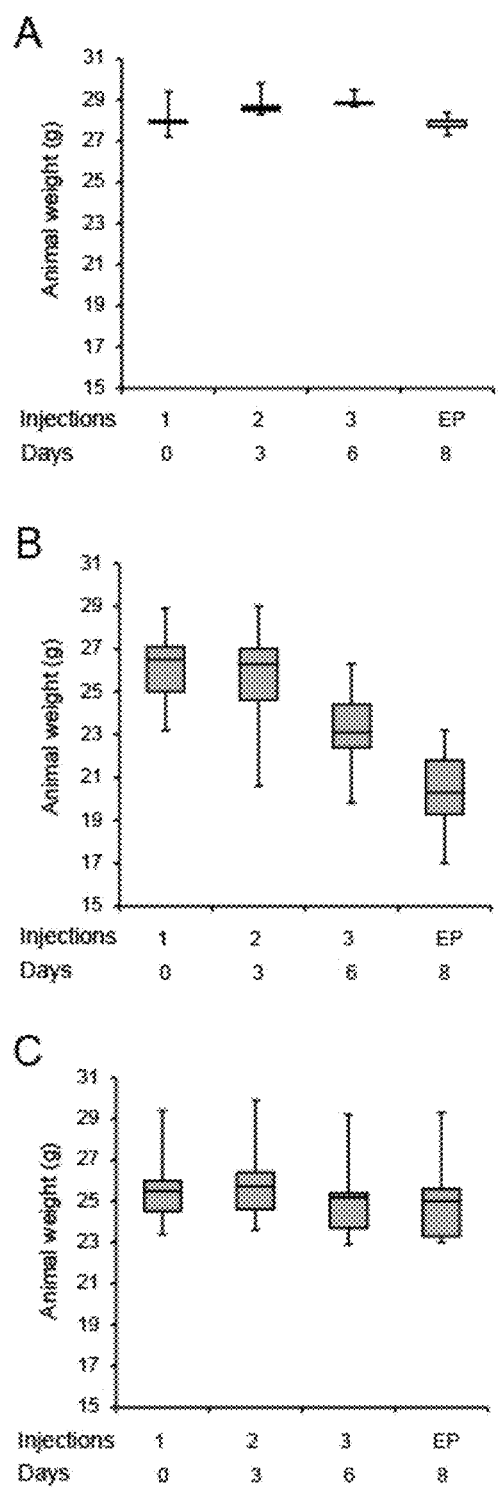
FIGURE 27 A-C

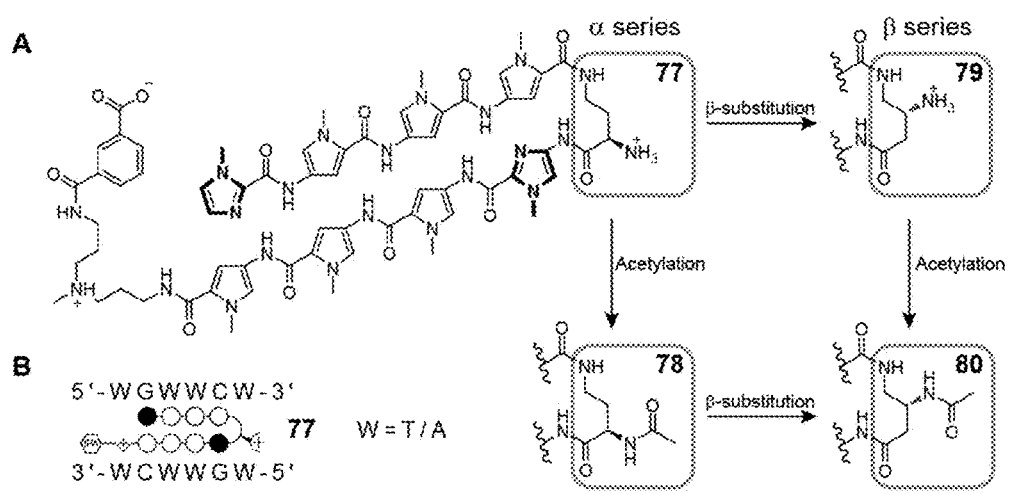
FIGURE 28 A-B

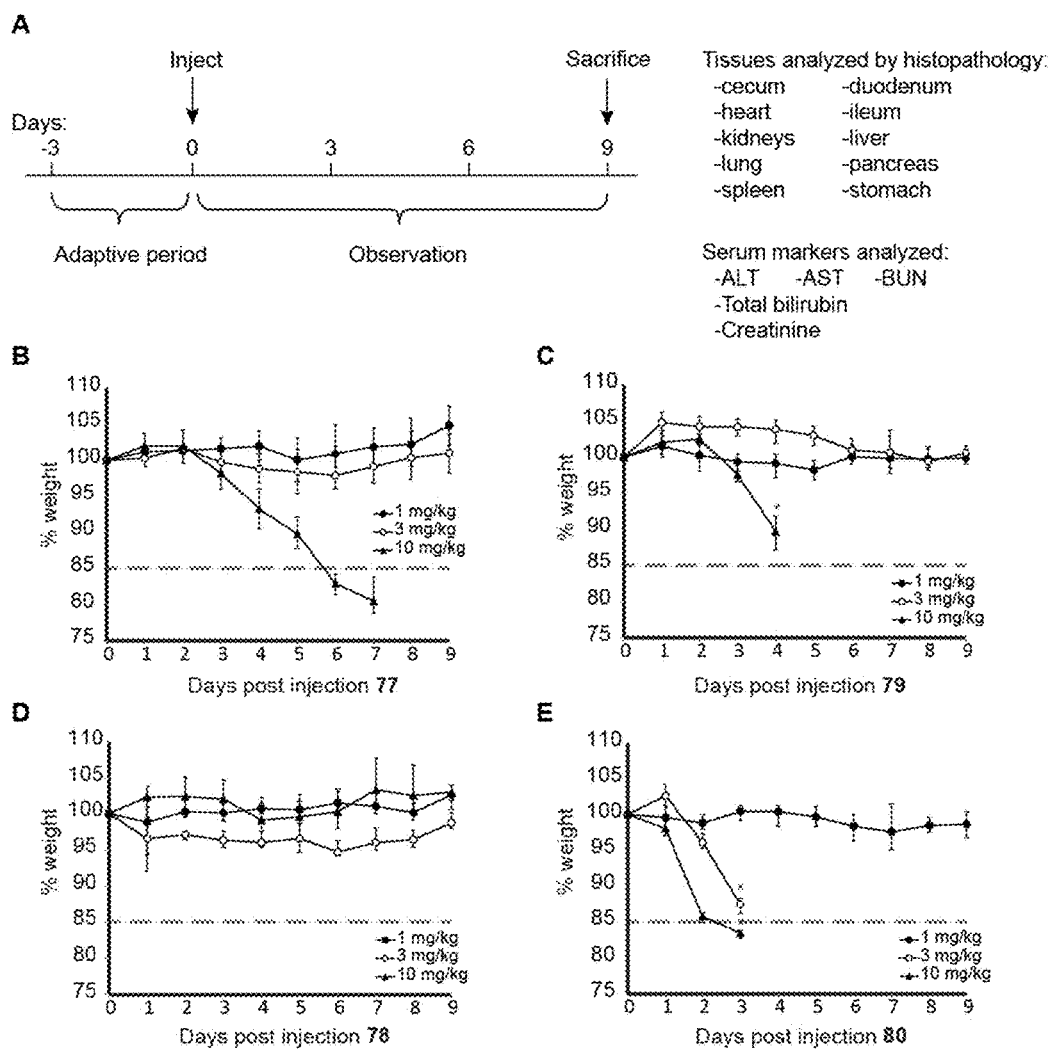
FIGURE 29 A-E

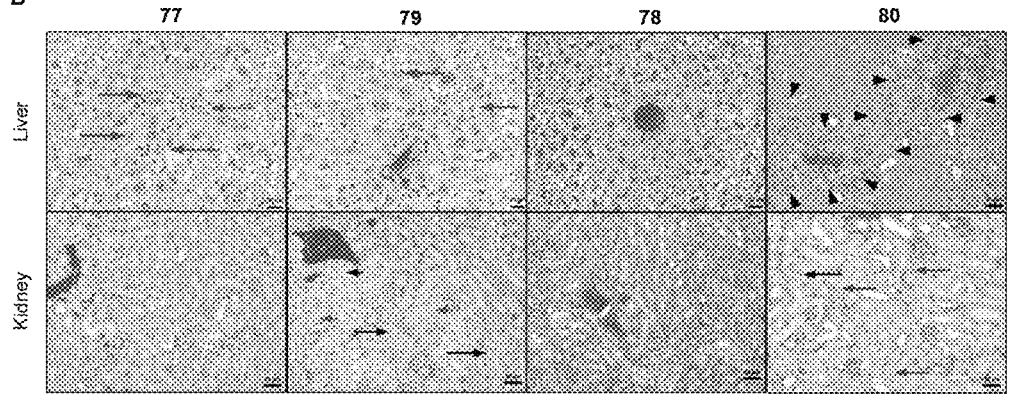
FIGURE 30 A-C

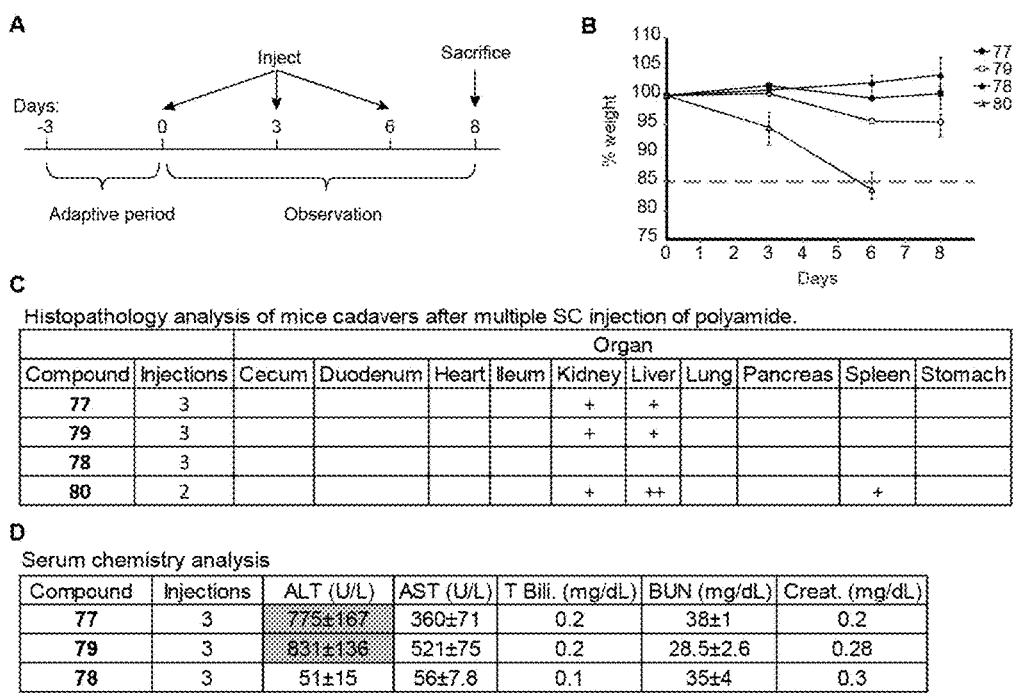
FIGURE 31 A-D

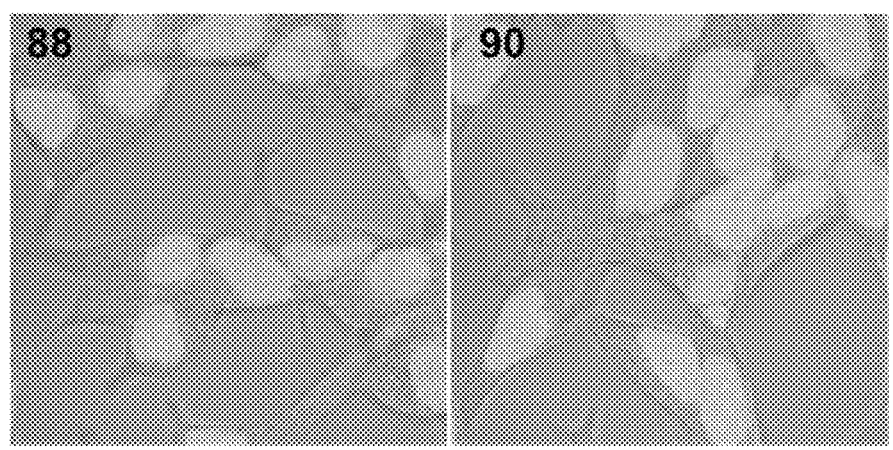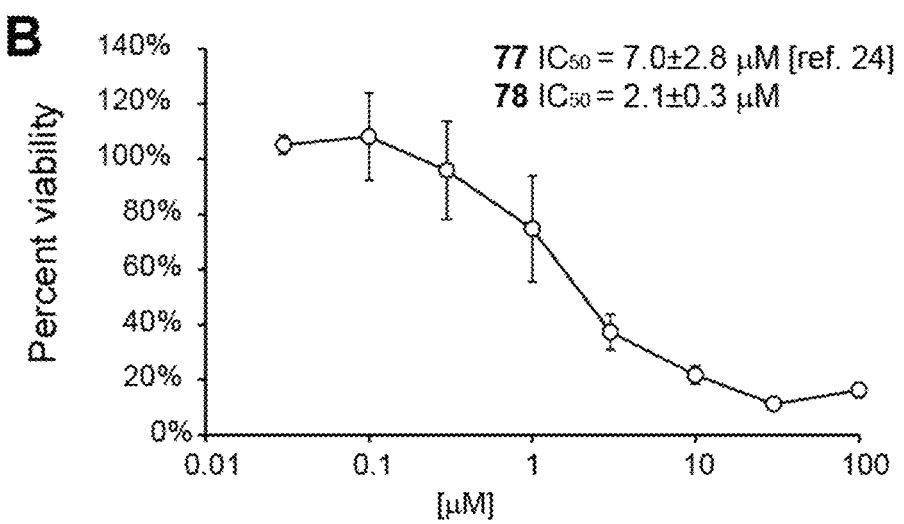
FIGURE 32 A-B

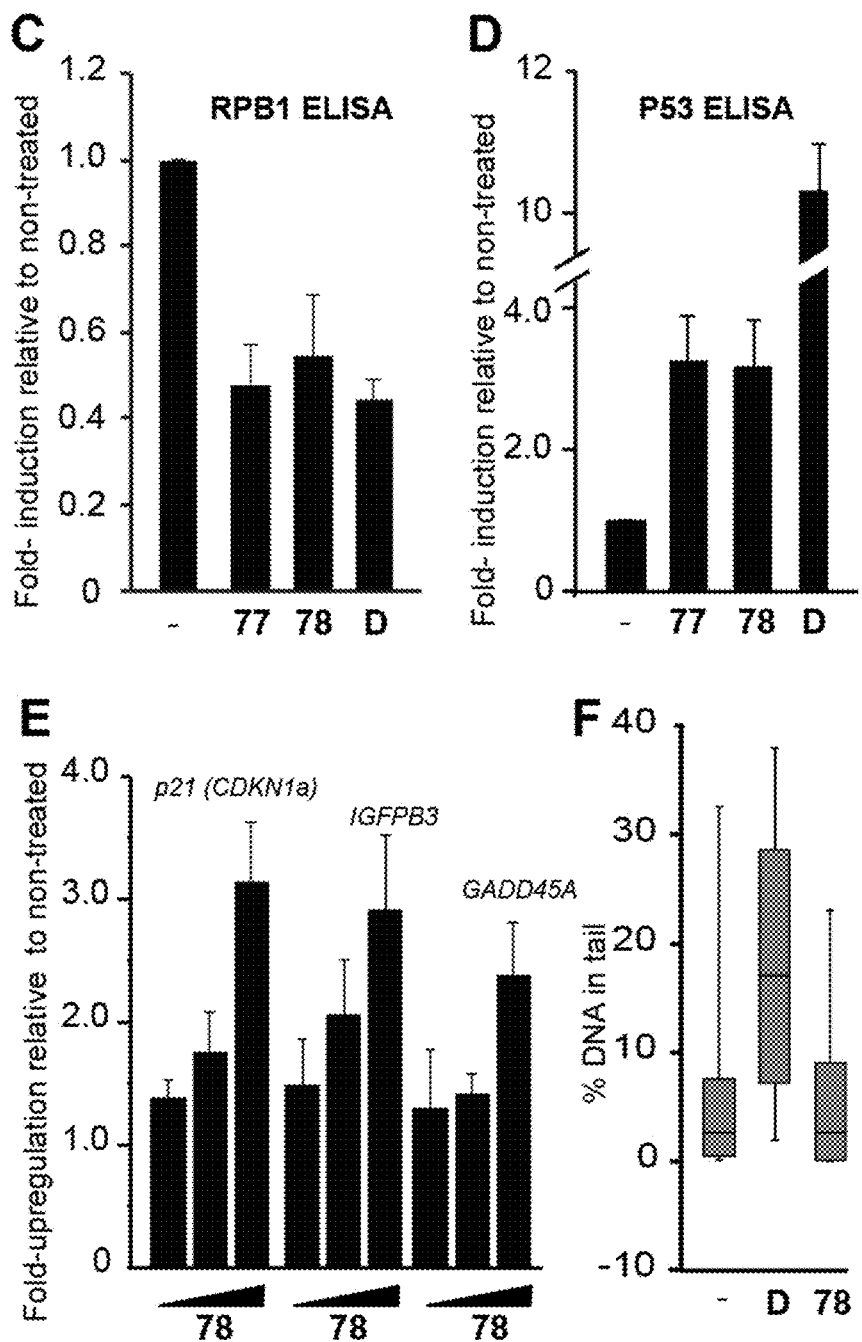
FIGURE 32 C-F

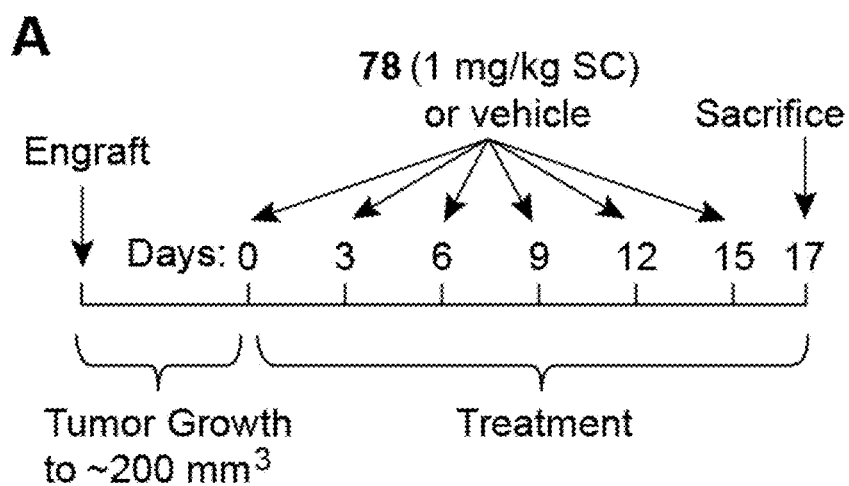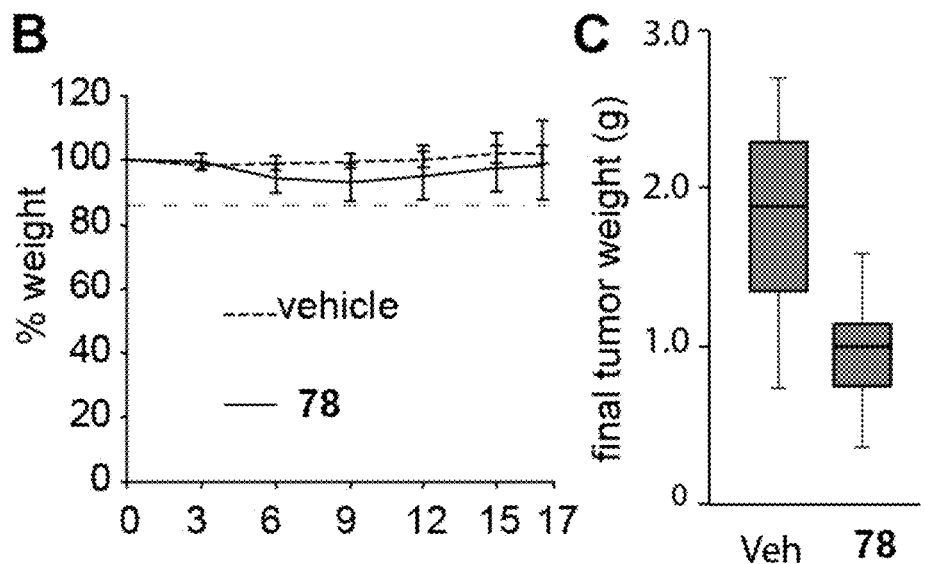
FIGURE 33 A-C

D

| Serum Chemistries | |
| --- | --- |
| AST (units/L) | 80±9 |
| ALT (units/L) | 134±56 |
| Total Bilirubin (mg/dL) | 0.14±0.05 |
| BUN (mg/dL) | 40±5 |
| Creatinine (mg/dL) | 0.1 |

E

| Hematology | Pre- | Post- |
| --- | --- | --- |
| Total WBC (x1,000/µL) | 8±1 | 9±1 |
| Total RBC (x1,000,000/µL) | 10±0.5 | 11±0.5 |
| HGB (g/dL) | 15±1 | 16±1 |
| Neutrophil (% of WBC) | 8±5 | 10±2 |
| Lymphocyte (% of WBC) | 89±5 | 88±1 |

FIGURE 33 D-E

| Polyamide | 5'- TTGC TGTTCT GCAA -3' | |
|---|---|---|
| | $T_m$ / °C | $\Delta T_m$ / °C |
| — | 61.8 (±0.5) | — |
| 77 | 74.1 (±0.3) | 12.3 |
| 79 | 75.1 (±0.4) | 13.3 |
| 78 | 70.1 (±0.2) | 8.3 |
| 80 | 74.9 (±0.2) | 13.2 |

SEQUENCE LISTING

```
<160> NUMBER OF SEQ ID NOS: 37

<210> SEQ ID NO 1
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A, T, C or G

<400> SEQUENCE: 1
ggtacannnt gttct                                                    15

<210> SEQ ID NO 2
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A, T, C or G

<400> SEQUENCE: 2
agaacannnt gtacc                                                    15

<210> SEQ ID NO 3
<211> LENGTH: 48
<212> TYPE: DNA
<213> ORGANISM: human

<400> SEQUENCE: 3
gggtgatcta gtaattgcag aacagcaagt gctagctctc cctccct                 48

<210> SEQ ID NO 4
<211> LENGTH: 48
<212> TYPE: DNA
<213> ORGANISM: human

<400> SEQUENCE: 4
aggggaggga gagctagcac ttgctgttct gcaattacta gatcaccc                48

<210> SEQ ID NO 5
```

-continued

```
<211> LENGTH: 16
<212> TYPE: DNA
<213> ORGANISM: human

<400> SEQUENCE: 5
gcctgcactt tgttct                                                       16

<210> SEQ ID NO 6
<211> LENGTH: 16
<212> TYPE: DNA
<213> ORGANISM: human

<400> SEQUENCE: 6
agaacaaagt gcaggc                                                       16

<210> SEQ ID NO 7
<211> LENGTH: 16
<212> TYPE: DNA
<213> ORGANISM: human

<400> SEQUENCE: 7
gcaaacaccg tgttca                                                       16

<210> SEQ ID NO 8
<211> LENGTH: 16
<212> TYPE: DNA
<213> ORGANISM: human

<400> SEQUENCE: 8
tgaacacggt gtttgc                                                       16

<210> SEQ ID NO 9
<211> LENGTH: 57
<212> TYPE: DNA
<213> ORGANISM: human

<400> SEQUENCE: 9
tagcctgcac tttgttctgt ctactacaca tgtcttagtg caaacaccgt gttcaga         57

<210> SEQ ID NO 10
<211> LENGTH: 57
<212> TYPE: DNA
<213> ORGANISM: human

<400> SEQUENCE: 10
tctgaacacg gtgtttgcac taagacatgt gtagtagaca gaacaaagtg caggcta         57

<210> SEQ ID NO 11
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A, T, C or G

<400> SEQUENCE: 11
aggtcannnt gacct                                                        15

<210> SEQ ID NO 12
<211> LENGTH: 15
<212> TYPE: DNA
<213> ORGANISM: human
<220> FEATURE:
<221> NAME/KEY: misc_feature
```

```
<222> LOCATION: 7, 8, 9
<223> OTHER INFORMATION: n = A, T, C or G

<400> SEQUENCE: 12
ggwacannnt gttct                                                     15

<210> SEQ ID NO 13
<211> LENGTH: 15
<212> TYPE: DNA
<213> ORGANISM: human
<220> FEATURE:
<221> NAME/KEY: misc_feature
<222> LOCATION: 1, 7, 8, 9, 15
<223> OTHER INFORMATION: n = A, T, C or G

<400> SEQUENCE: 13
ngwacwnnnt gtycn                                                     15

<210> SEQ ID NO 14
<211> LENGTH: 31
<212> TYPE: DNA
<213> ORGANISM: human

<400> SEQUENCE: 14
gcattgcaga acagcaagtg ctagctctcc c                                   31

<210> SEQ ID NO 15
<211> LENGTH: 15
<212> TYPE: DNA
<213> ORGANISM: human

<400> SEQUENCE: 15
agaacagcaa gtgct                                                     15

<210> SEQ ID NO 16
<211> LENGTH: 15
<212> TYPE: DNA
<213> ORGANISM: human

<400> SEQUENCE: 16
agcacatcga gttca                                                     15

<210> SEQ ID NO 17
<211> LENGTH: 15
<212> TYPE: DNA
<213> ORGANISM: human

<400> SEQUENCE: 17
agaacagggt gttct                                                     15

<210> SEQ ID NO 18
<211> LENGTH: 20
<212> TYPE: DNA
<213> ORGANISM: human

<400> SEQUENCE: 18
ggtttctctc cgcccgtctt                                                20

<210> SEQ ID NO 19
<211> LENGTH: 20
<212> TYPE: DNA
<213> ORGANISM: human

<400> SEQUENCE: 19
```

| | |
|---|---|
| tgttcgacag tcagccgcat | 20 |

<210> SEQ ID NO 20
<211> LENGTH: 20
<212> TYPE: DNA
<213> ORGANISM: human

<400> SEQUENCE: 20

| | |
|---|---|
| tagaaggggg atagggggaac | 20 |

<210> SEQ ID NO 21
<211> LENGTH: 21
<212> TYPE: DNA
<213> ORGANISM: human

<400> SEQUENCE: 21

| | |
|---|---|
| ccagaaaact ggctccttct t | 21 |

<210> SEQ ID NO 22
<211> LENGTH: 19
<212> TYPE: DNA
<213> ORGANISM: human

<400> SEQUENCE: 22

| | |
|---|---|
| gccattagcg catcacagt | 19 |

<210> SEQ ID NO 23
<211> LENGTH: 19
<212> TYPE: DNA
<213> ORGANISM: human

<400> SEQUENCE: 23

| | |
|---|---|
| accgaggcac tcagaggag | 19 |

<210> SEQ ID NO 24
<211> LENGTH: 20
<212> TYPE: DNA
<213> ORGANISM: human

<400> SEQUENCE: 24

| | |
|---|---|
| gcaggatcct tccattgaga | 20 |

<210> SEQ ID NO 25
<211> LENGTH: 19
<212> TYPE: DNA
<213> ORGANISM: human

<400> SEQUENCE: 25

| | |
|---|---|
| ctcttggaga ccgacgctg | 19 |

<210> SEQ ID NO 26
<211> LENGTH: 20
<212> TYPE: DNA
<213> ORGANISM: human

<400> SEQUENCE: 26

| | |
|---|---|
| ctgatccaac caatcacctg | 20 |

<210> SEQ ID NO 27
<211> LENGTH: 20
<212> TYPE: DNA
<213> ORGANISM: human

<400> SEQUENCE: 27
aagcctggct ctgtgtgtaa         20

<210> SEQ ID NO 28
<211> LENGTH: 19
<212> TYPE: DNA
<213> ORGANISM: human

<400> SEQUENCE: 28
cggtcttcct ccgactcac          19

<210> SEQ ID NO 29
<211> LENGTH: 20
<212> TYPE: DNA
<213> ORGANISM: human

<400> SEQUENCE: 29
ctctgcgtca acgctagtgc         20

<210> SEQ ID NO 30
<211> LENGTH: 20
<212> TYPE: DNA
<213> ORGANISM: human

<400> SEQUENCE: 30
cagcccatga tggttctgat         20

<210> SEQ ID NO 31
<211> LENGTH: 20
<212> TYPE: DNA
<213> ORGANISM: human

<400> SEQUENCE: 31
gacatgtttt ctgacggcaa         20

<210> SEQ ID NO 32
<211> LENGTH: 17
<212> TYPE: DNA
<213> ORGANISM: human

<400> SEQUENCE: 32
ctcaatcacc ccctgcc            17

<210> SEQ ID NO 33
<211> LENGTH: 20
<212> TYPE: DNA
<213> ORGANISM: human

<400> SEQUENCE: 33
gagtcctgag tccggatgaa         20

<210> SEQ ID NO 34
<211> LENGTH: 22
<212> TYPE: DNA
<213> ORGANISM: human

<400> SEQUENCE: 34
ctcatttgga attttgccga tt      22

<210> SEQ ID NO 35
<211> LENGTH: 21
<212> TYPE: DNA
<213> ORGANISM: human

```
<400> SEQUENCE: 35
ccgagtgaag atcccctttt t                                    21

<210> SEQ ID NO 36
<211> LENGTH: 12
<212> TYPE: DNA
<213> ORGANISM: human

<400> SEQUENCE: 36
cgatgttcaa gc                                              12

<210> SEQ ID NO 37
<211> LENGTH: 14
<212> TYPE: DNA
<213> ORGANISM: human

<400> SEQUENCE: 37
ttgctgttct gcaa                                            14
```

INHIBITORS FOR STEROID RESPONSE ELEMENTS AND RNA POLYMERASE II AND RELATED METHODS

This application is a continuation-in-part of U.S. application Ser. No. 12/148,943, filed Apr. 22, 2008, currently pending, which claims the benefit of U.S. Provisional Application No. 60/926,080, filed Apr. 23, 2007, which are incorporated herein by reference in their entirety. This application claims the benefit of U.S. Provisional Application No. 61/700,795, filed Sep. 13, 2012, which is incorporated herein by reference in its entirety.

This invention was made with government support under GM051747 and GM027681 awarded by the National Institutes of Health. The U.S. Government has certain rights in the invention.

1.0 FIELD OF THE INVENTION

The present invention relates to compositions for inhibiting response elements for androgen receptors, glucocorticoid receptors and estrogen receptors, for example, to down regulate gene regulation or expression modulated by these receptors, and to methods to treat related diseases. The present invention also relates to polyamides capable of modulating the activity of RNA polymerase II and p53, and to methods to treat related diseases.

2.0 BACKGROUND

Genes in higher organism are regulated through binding of regulatory molecules to regulatory sequences which may be in the gene or operatively linked to the gene. A variety of regulatory sequences are known. Among the gene regulatory molecules are steroids which typically bind receptor molecules to form a complex that can bind DNA to modulate gene expression. Androgens, glucocorticoids and estrogens are examples of steroids capable gene regulation through DNA sequences called androgen response element (ARE), glucocorticoid response element (GRE), and estrogen response element (ERE), respectively. Androgens form complexes with an androgen receptor (AR) to bind an ARE. Glucocorticoids form complexes with a glucocorticoid receptor (GR) to bind a GRE. Estrogens form complexes with an estrogen receptor (ER) to bind ERE. The AR, GR, and ER share a highly conserved DNA-binding domain. This domain, related to the classical Cys-2-His-2 zinc finger motifs, contains two modules of zinc coordinated by four cysteines.

AR signaling regulates for example normal prostate development and contributes to the progression of prostate cancer. Drug therapies that act to limit circulating androgen levels or directly antagonize ligand binding to AR initially slow prostate cancer growth but nearly all patients treated with such anti-androgen therapies will eventually develop hormone-refractory disease. Dysregulation of AR activity is thought to contribute to this transition. Up-regulation of AR mRNA, mutations in the AR itself, and ligand-less activation of AR through other signaling pathways contribute to this dysregulation. Direct antagonism of AR-DNA binding could inhibit androgen receptor activity in hormone-refractory conditions where androgen antagonists that target the ligand-binding pocket are ineffective.

ARE, GRE and ERE mediated gene regulation are involved in diseases including cancer. Inhibition of ARE-, GRE- and ERE-mediated gene regulation would be highly desirable in the treatment of diseases Inhibiting ARE-, GRE- and ERE-mediated gene regulation requires, for example, selectively down-regulating the binding of natural regulators in a cell to the ARE, GRE and ERE Inhibition of ARE and GRE mediated gene expression has been attempted through binding of small molecules to the ligand binding domains of the AR or GR to prevent binding of the AR or GR to AREs or GREs, or to prevent a transcriptionally active complex of AR or GR at AREs or GREs. Examples of such attempts are anti-androgen drugs (for example, flutamide and bicalutamide).

A different approach involves inhibiting the binding of AR, GR or ER to the ARE, GRE or ERE by occupying ARE, GRE or ERE with a molecule capable of specifically recognizing an ARE, GRE or ERE Inhibition through specific binding of ARE, GRE or ERE would be an effective way to modulate gene expression, for example, to treat diseases like cancer Inhibitors of ARE-, GRE-, and ERE-mediated gene regulation should be able to enter cells and to enter the nucleus of the cells. Such inhibitors should also be capable of accessing ARE, GRE and ERE sequences in the genome and they should not bind other sequences or molecules to a degree that would render them ineffective. Also, inhibitors should not accumulate in other organelles, for example lysosomes, to a degree that renders them ineffective.

Compounds capable of inhibiting ARE-, GRE- and ERE-mediated gene regulation would therefore be highly desirable. The present invention provides such compounds.

3.0 SUMMARY OF THE INVENTION

The present invention relates to polyamides capable of modulating ARE-, GRE-, and ERE-mediated gene regulation in a cell. Polyamides of the current invention, in certain embodiments, are capable of entering a cell and of binding ARE, GRE and ERE in the genome of the cell to inhibit binding of other molecules to the ARE, GRE and ERE.

Polyamides of the invention in certain embodiments comprise a structure 1, wherein each X is independently selected from CH, N, or COH (each p independently selected from 0 and 1), wherein each $R_2$ is independently selected from H, a $C_{1-10}$ alkyl, a $C_{1-10}$ alkenyl, a $C_{1-10}$ alkynyl, —(CH2)$_q$-NH—$R_6$ (each q independently selected from 1-10). In structure 1, each pyrrole unit of structure 2 may be independently replaced by a beta-alanine of structure 3. Each $R_3$ and $R_4$, and/or each $R_1$ and $R_5$ in structure 1 may be covalently linked by a turn of any one of structures 4-6 to form a hairpin- or a cyclic-shaped molecule. Any $R_2$ may be covalently linked to another $R_2$ to form an H- or U-shaped molecule. Each $R_7$, $R_8$ and $R_9$ in structures 4 and 5 may be independently selected from an R or S isomer, and is independently selected from structures 7-17 (each s independently selected from 1-10). Each $R_1$ and $R_4$ (e.g., in structure 1), and each $R_{10}$ (e.g., in structures 14 and 16), is independently selected from structures 18 (each u independently selected from 0 and 1), with each A independently selected from structure 21. Each $R_3$ and $R_5$ (e.g., in structure 1), each $R_6$ (e.g., in $R_2$), and each $R_{11}$ (e.g., in structures 15 and 17), is independently selected from structures 19 and 20 (each v and w independently selected from 0 and 1), with each A' independently selected from structure 22, and with each Z independently selected from structures 23 and 24. Each $R_{12}$ is independently selected from structures 25-54 (each d, e, f, h and j independently selected from 1-10), with each y independently selected from structures 55-57. Each t is independently selected from 1-10. Each $R_{13}$ is independently selected from structures 58-74 (each g and e independently selected from 1-10). In $R_{12}$ and $R_{13}$, each $R_{14}$ represents one, two, three, four, or five sidechains of the ring (up to the maximum number) with each $R_{14}$ being independently selected from H, OH, SH, $CH_3$, $NH_2$, halogen, F, Cl, Br, or I, and each amide linkage of structure 75 that occurs in structures 42-59 may be independently replaced by a thiourea linkage of structure 76. Polyamides of the current invention, in certain preferred embodiments, comprise any one or more of structures 77-84.

Polyamides of the invention in certain embodiments comprise any one or more of structures 92 and 93, wherein $R_{15}$ is selected from structures 94-97, wherein each m, n, o is independently selected from 1-10. Each $R_{16}$-$R_{23}$ is independently selected from structures 98-107, wherein each q is independently selected from 1-10, and wherein each X' and Y' are independently selected from H, OH, SH, $CH_3$, $CH_2CH_3$, $NH_2$, $NO_2$, COOH, COOMe, COOEt, F, Cl, Br, and I.

The present invention also comprises methods to inhibit ARE-, GRE-, and ERE-mediated gene regulation, for example, by inhibiting the binding of ARE, GRE and/or ERE by another molecule, for example, a complex comprising an androgen and an AR, a complex comprising a glucocorticoid and a GR, a complex comprising an estrogen and an ER, or an AR, a GR or an ER not complexed to an androgen, a glucocorticoid, or an estrogen. The present invention also comprises methods to interfere with RNA polymerase II activity and methods to activate p53 signaling. In certain embodiments, a method of the invention is useful for the treatment of cancer.

The invention further provides methods of using a polyamide of the invention as a research tool and for therapeutic methods in humans, animals, and/or plants. Methods of the current invention preferably comprise administering a polyamide of the invention to a cell, a human, an animal and/or a plant to modulate the expression of a gene that is regulated through an ARE, a GRE, and/or an ERE and/or to modulate physiological processes linked to the expression of such a gene.

4.0 BRIEF DESCRIPTION OF THE DRAWINGS

FIG. 1: Polyamides of certain embodiments of the invention are shown as structure 1.

FIG. 2A-2C: Structural elements of a polyamide shown in FIG. 1 are exemplified. FIG. 2A: Any pyrrole unit of structure 2 in structure 1 may be independently replaced by beta alanine structure 3. Any turn in structure 1 may be independently selected from structures 4-6. FIG. 2B: Each $R_7$, $R_8$ and $R_9$ in structures 4 and 5 may be an R or S isomer, and is independently selected from structures 7-17 (each s independently selected from 1-10). FIG. 2C: Each $R_1$ and $R_4$ in structure 1, and each $R_{10}$ in structures 14 and 16, is structure 18 (each u independently selected from 0 and 1), with each A having structure 21. Each $R_3$ and $R_5$ in structure 1, each $R_2$ in $R_6$, and each $R_{11}$ in structures 15 and 17, is independently selected from structures 19 and 20 (each v and w independently selected from 0 and 1), with each A' having structure 22, and with each Z independently selected from structures 23 and 24 (each t independently selected from 1-10).

Figure 3B:
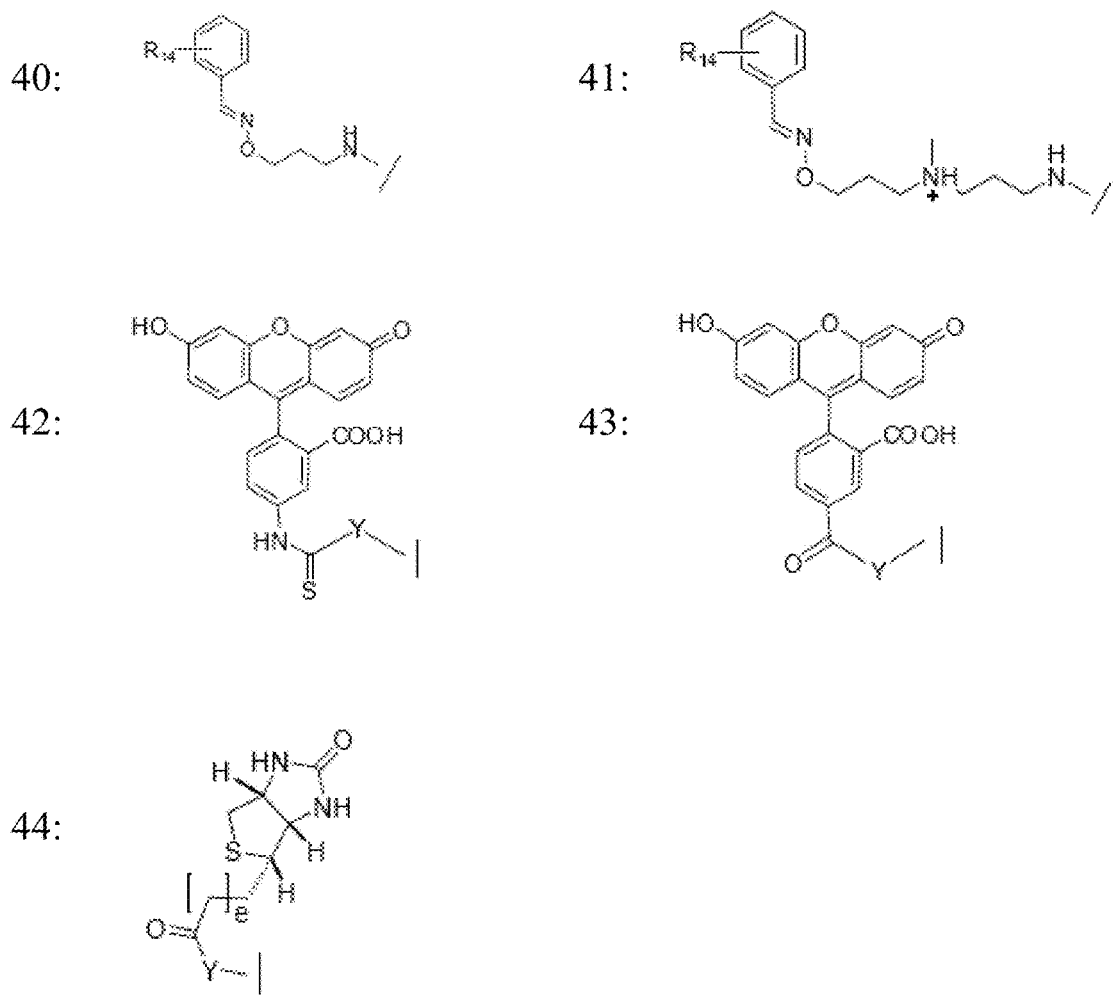
Figure 3C:
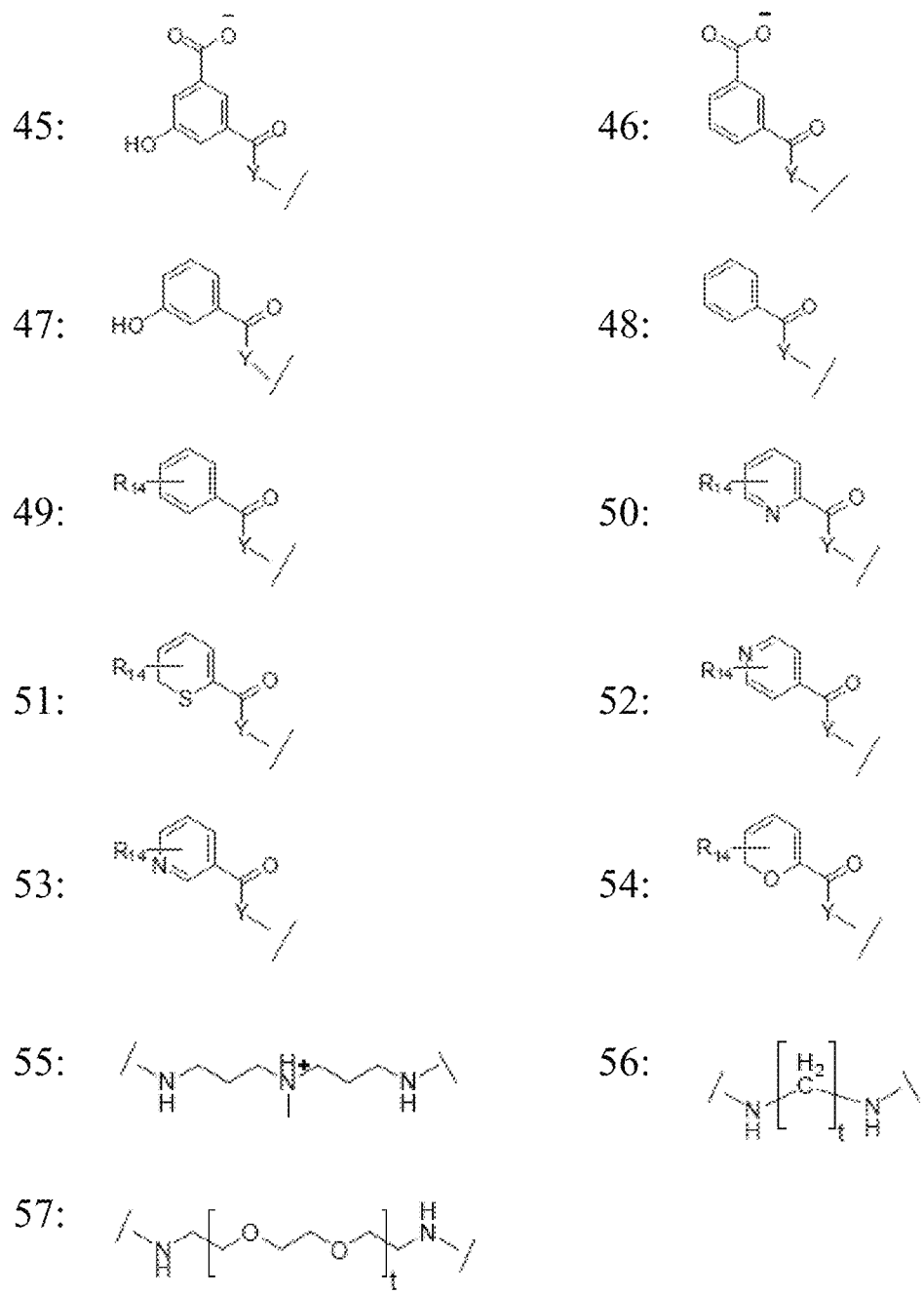
Figure 4A:
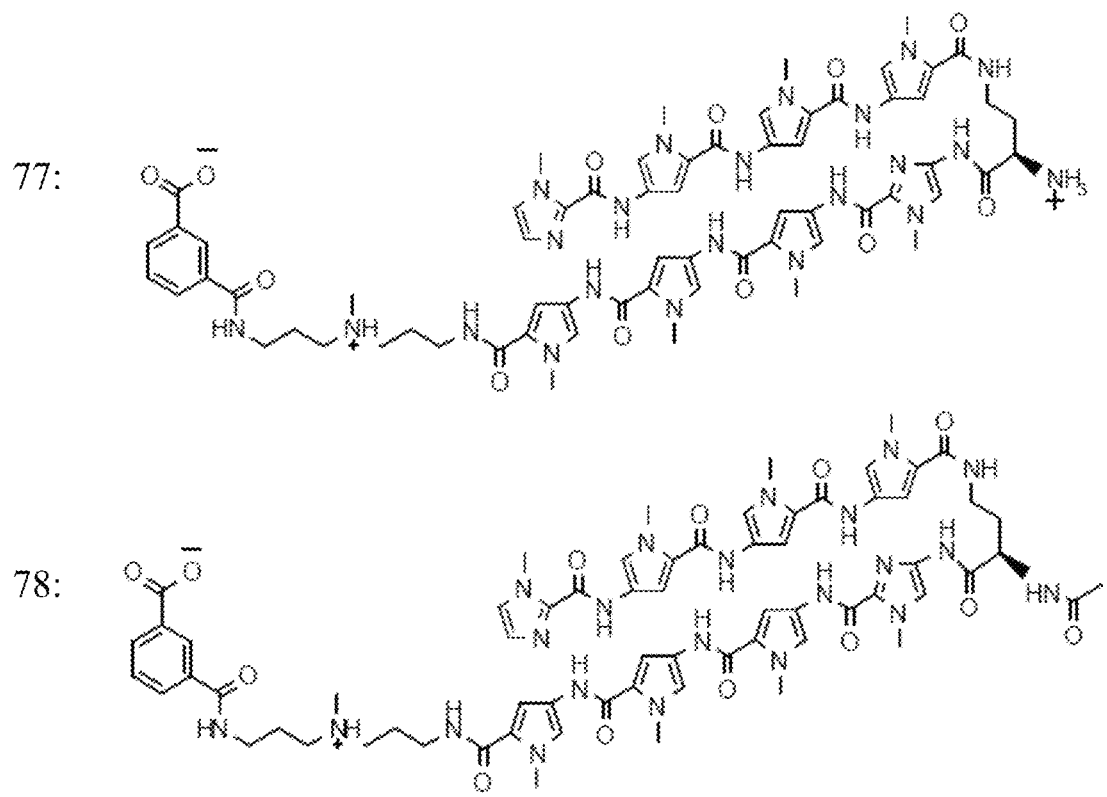
Figure 4B:
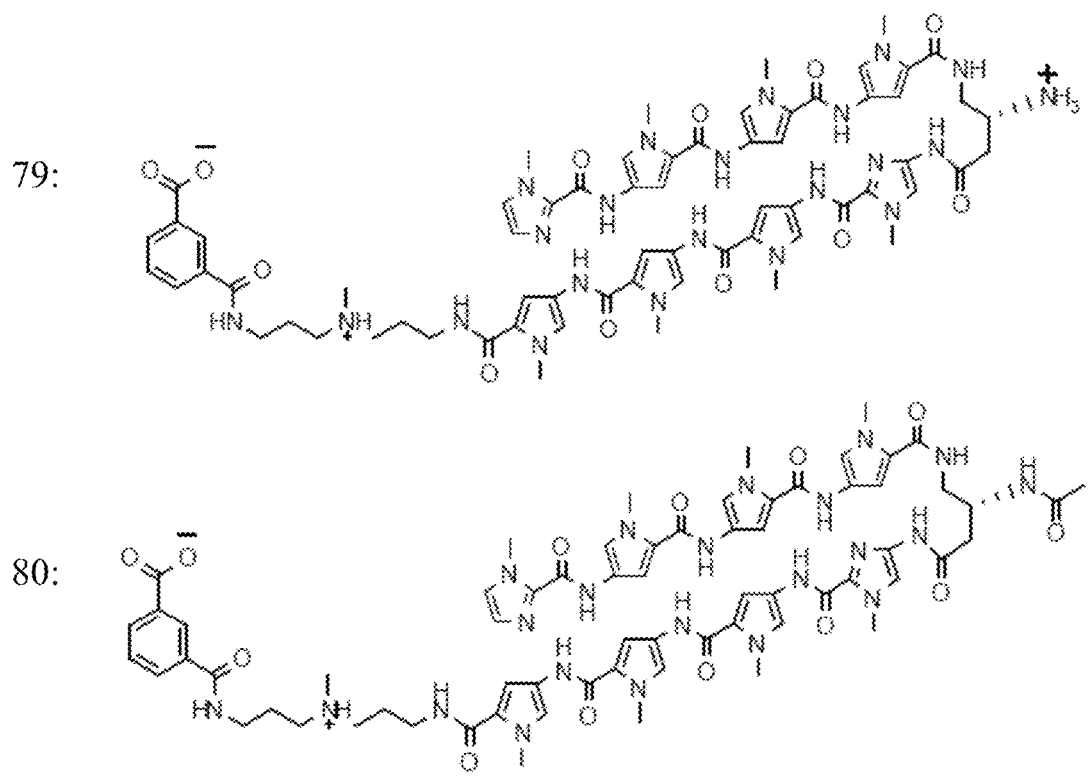
Figure 4C:
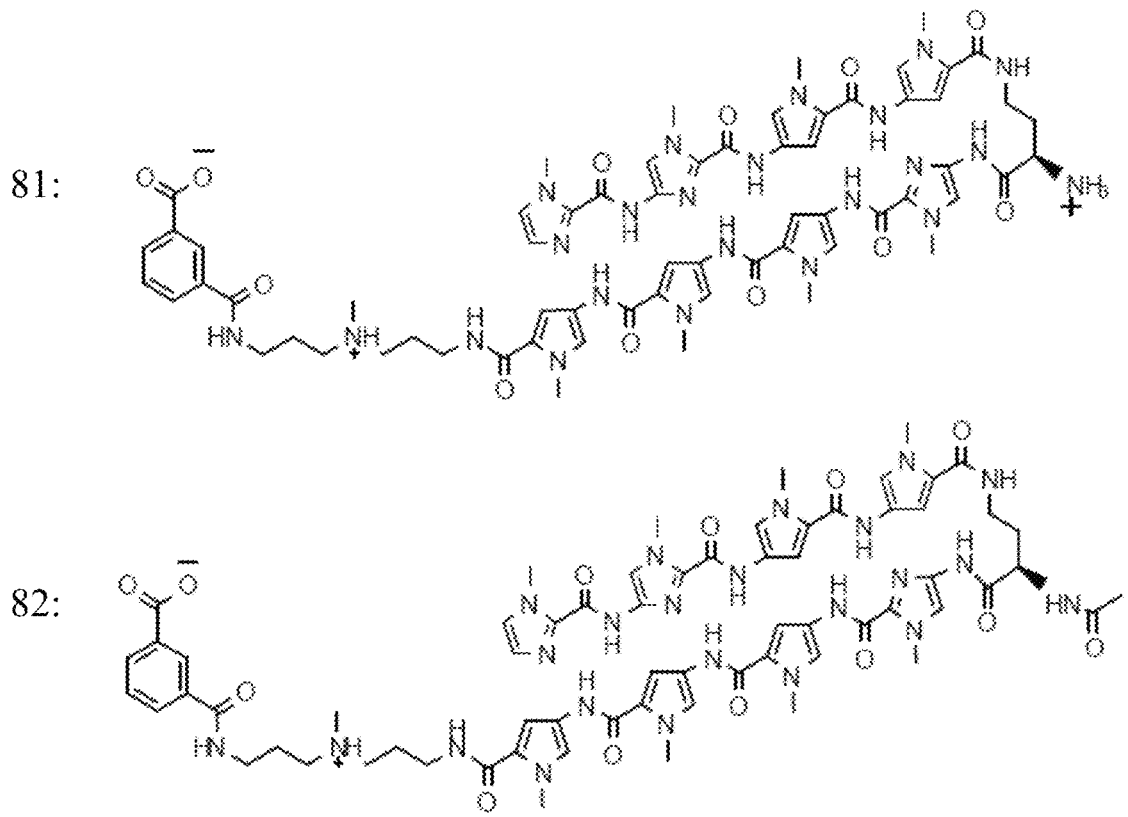
Figure 4D:
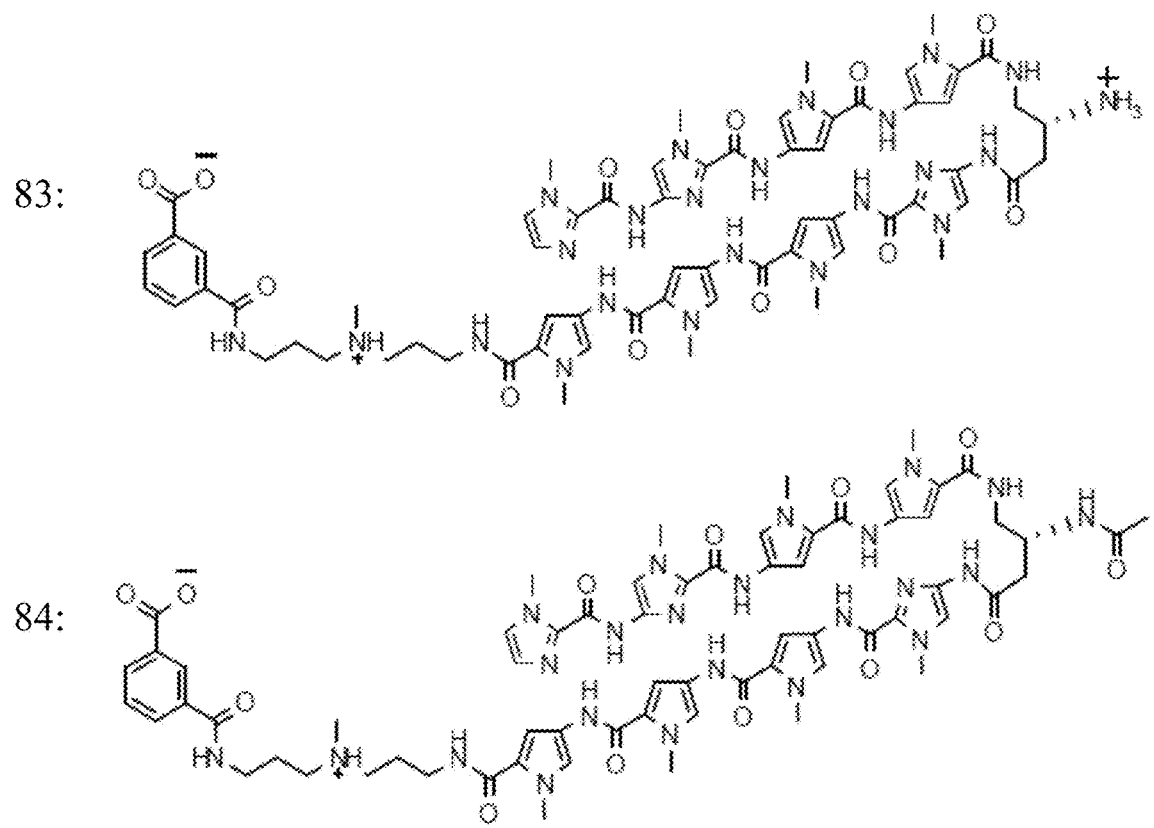

FIG. 3A-3E: Structural elements of a polyamide shown in FIGS. 1 and 2 are exemplified. FIGS. 3A-3C: Each $R_{12}$ is independently selected from structures 25-54 (each d, e, f, h and j independently selected from 1-10), with each y independently selected from structures 55-57. FIGS. 3D-3E: Each $R_{13}$ is independently selected from structures 58-74 (each g and e independently selected from 1-10). In $R_{12}$ and $R_{13}$, each $R_{14}$ represents one, two, three, four, or five sidechains of the ring (up to the maximum number) with each $R_{14}$ being independently selected from H, OH, SH, $CH_3$, $NH_2$, halogen, F, Cl, Br, or I, and each amide linkage of structure 75 in structures 42-59 may be independently replaced by a thiourea linkage of structure 76. Each t is independently selected from 1-10.

FIG. 4: Polyamides of certain embodiments of the invention are shown in FIGS. 4A-D as structures 77-84.

Figure 5:
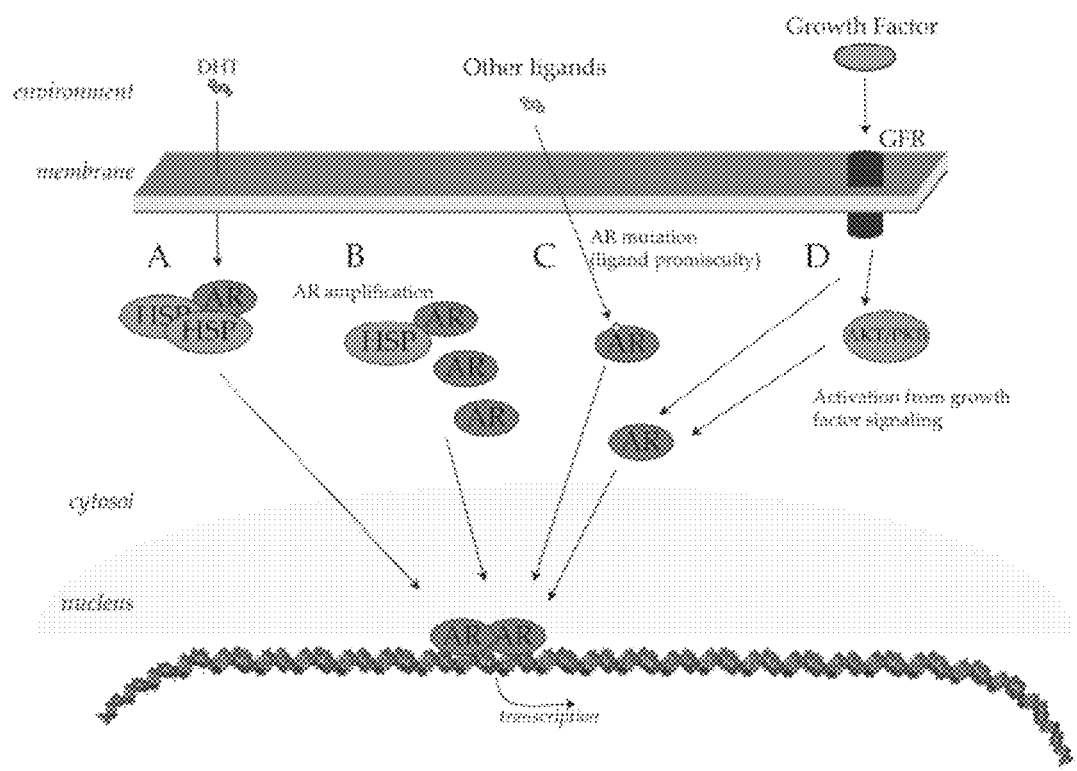

FIG. 5: Androgen receptor activation in androgen independent prostate cancer (A) Normal activation of AR by DHT. (B) AR amplification leads to activation. (C) Mutations in AR leads to promiscuity for other ligands. (D) Ligand-independent activation by upstream signaling.

FIG. 6: (A) Illustration of the binding of androgen receptor (AR) to androgen response elements (ARE) (SEQ ID NOS:1, 2) in the promoters and enhancers of target genes resulting in a modulation of the level of gene expression. (B) The ARE is targeted and bound by one or more pyrrole-imidazole containing polyamides that prevent or displace androgen receptor, modifying the expression of androgen receptor regulated genes.

FIG. 7: (A) Model of the androgen receptor (AR) transcription complex. (B) Consensus androgen response element (SEQ ID NOS:1, 2). (C) Structures and ball-and-stick models of polyamide 1 (structure 77, FIG. 4), designed to bind the consensus ARE, and 2, a mismatch. Imidazole and pyrrole units are represented by closed and open circles, respectively. The isophthalic acid tail moiety is represented by a hexagon.

FIG. 8: Binding of 1 and 2 to the ARE in the PSA promoter. (A) Illustration of pAR and partial sequence of the PSA promoter (SEQ ID NOS:3, 4). (B) Quantitative DNase I footprint titration experiments for polyamides 1 and 2 on the 5'-end-labeled PCR product of plasmid pAR-PSA: lane 1, intact DNA; lane 2, A reaction; lane 3, G reaction; lane 4, DNAse I standard; lanes 5-15, 1 pM, 3 pM, 10 pM, 30 pM, 100 pM, 300 pM, 1 nM, 3 nM, 10 nM, 30 nM, 100 nM polyamide, respectively. (C) Isotherm for 1 binding to the ARE half site 5'-AGAACA-3'. Polyamide 1 has a $K_a=8.3\pm1.7\times10^9$ for this site. Polyamide 2 shows no measurable binding in the footprinted region. (D) EMSA of DHT-stimulated LNCaP cell nuclear extract (NE) binding to a 31 base pair oligonucleotide duplex containing the PSA promoter ARE in the presence of 1 and 2.

FIG. 9: Inhibition of DHT-induced PSA and FKBP5 expression by 1 and 2. (A) Induction of PSA mRNA in the presence of 1, 2, and bicalutamide, B, measured by quantitative real-time PCR. 1 and bicalutamide inhibit expression of PSA in a dose-dependent manner up to approximately 70% at 10 µM. 2 has a more modest effect. (B) Secreted PSA protein measured by ELISA. (C) Chromatin immunoprecipitation assays with anti-AR or mock antibody treatment expressed as fold-enrichment (specific/mock) of DNA sequences at the PSA promoter and enhancer. AR occupancy at the PSA promoter and enhancer is decreased in the presence of 1 (10 µM) but not 2. (D) Induction of FKBP5 mRNA in the presence of 1, 2, and bicalutamide, B. (E) Chromatin immunoprecipitation assays with anti-AR at the FKBP5 fifth intron enhancer. Polyamide concentrations are 10 µM.

FIG. 10: Global effects on transcripts interrogated using Affymetrix high-density Human Genome U133 Plus 2.0 Arrays. (A) Divisive clustering of all measured transcripts under the four specified conditions: no treatment control; B, bicalutamide (10 µM); 1 (10 µM); 2 (10 µM). Clustering was based on an error weighted Pearson correlation of intensity ratios for each treatment as compared to DHT-induced controls. (B) Ven diagrams representing transcripts down- and up-regulated (|fold-change| μ2.0, p μ0.01) by bicalutamide and 1. Numbers inside the intersections represent transcripts affected by both treatments. Of the 122 transcripts down-regulated by both bicalutamide and 1, 117 are also observed to be induced by DHT at the same thresholds. (C) Agglomerative clustering of expression changes of the 199 transcripts induced or repressed 4-fold (p≤0.01) or more by 1 nM DHT under the designated treatment conditions. Of the DHT-induced set, 70 were inhibited by polyamide 1, 20 were inhibited by 2, and 186 by bicalutamide (|fold-change|≥2.0, p≤0.01). Clustering parameters were the same as in (A). Treatments reported are an error-weighted average from three experiments, except the non-induced control which was an average from two experiments.

FIG. 11: DHT-induction of KLK2 mRNA (A) and TMPRSS2 mRNA (B) in the presence of 1, 2 measured by quantitative real-time PCR.

FIG. 12. Disrupting the AR/ARE interface in hormone refractory prostate cancer cells, LNAR-CS. LNAR-CS cells over-express AR, and form hormone refractory tumors when xenografted in mice. AR regulated genes in LNAR-CS cells are not inhibited by anti-androgens such as bicalutamide. (A) Upregulation of androgen receptor defeats many synthetic anti-androgens targeted to the ligand-binding pocket. Addition of a DNA-binding polyamide targeting the ARE consensus sequence (SEQ ID NOS:1, 2) disrupts the AR/ARE interface and offers an alternative anti-androgen strategy that maintains efficacy in hormone refractory cells such as LNAR-CS. (B) Inhibition of DHT-induced PSA in LNAR-CS cells by 1 and 2 and basal PSA expression (no DHT) by 1 and 2 (C). Bicalutamide induces expression of PSA in LNAR-CS cells.

Figure 13D:
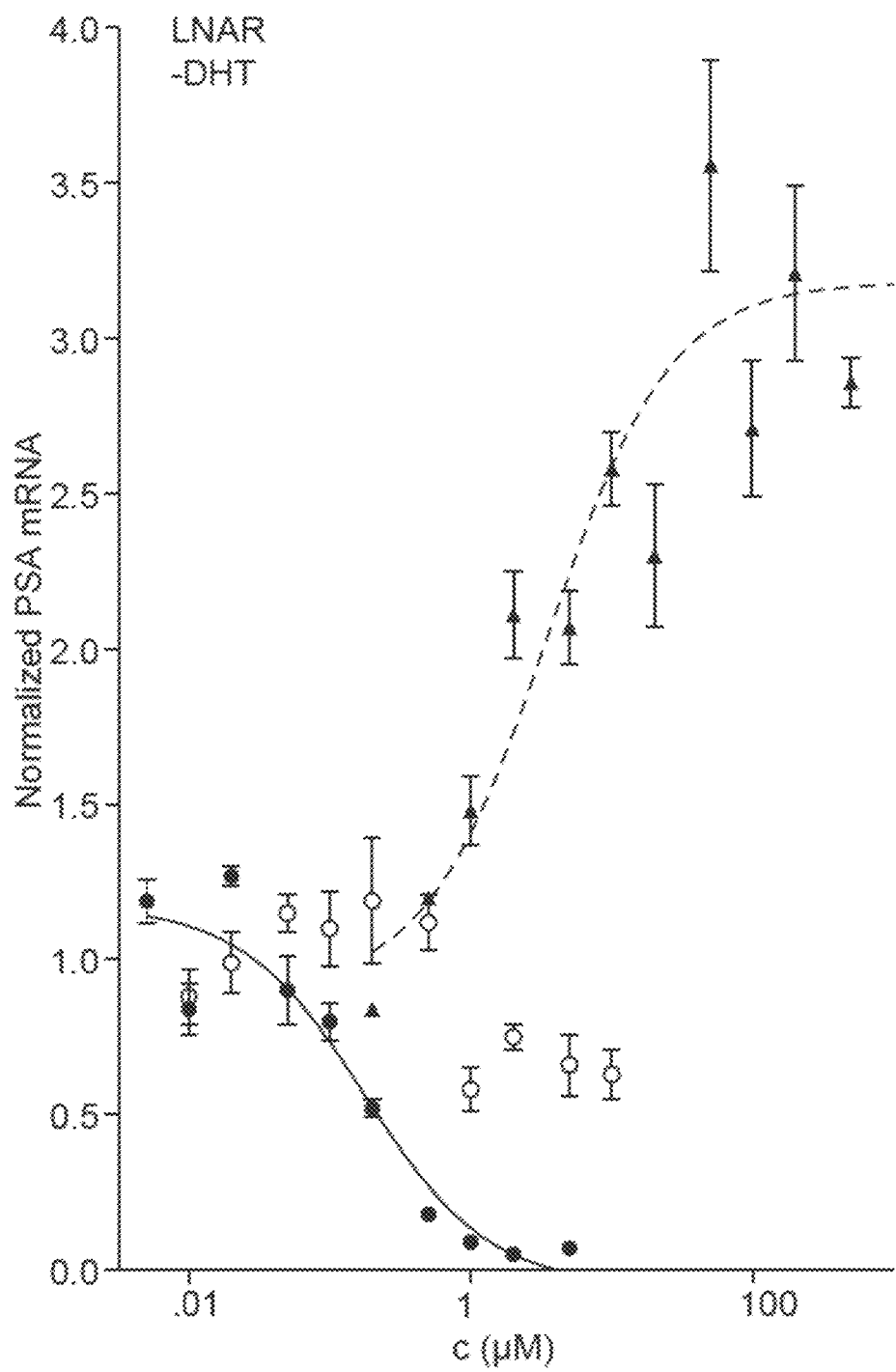

FIG. 13. Representative isotherms depicting the effects of polyamide 3 that targets the ARE (square), and control polyamide 4 (circle), and bicalutamide (triangle) on PSA mRNA expression. (A) Structures of 3 and 4. (B) Inhibition of DHT-induced PSA mRNA expression in LNCaP cells by 3 and Bic. (C) Inhibition of DHT-induced PSA mRNA expression in LNAR cells by 3. (D) Inhibition of basal PSA mRNA expression (no DHT) by 3 and induction by bicalutamide.

Figure 14:
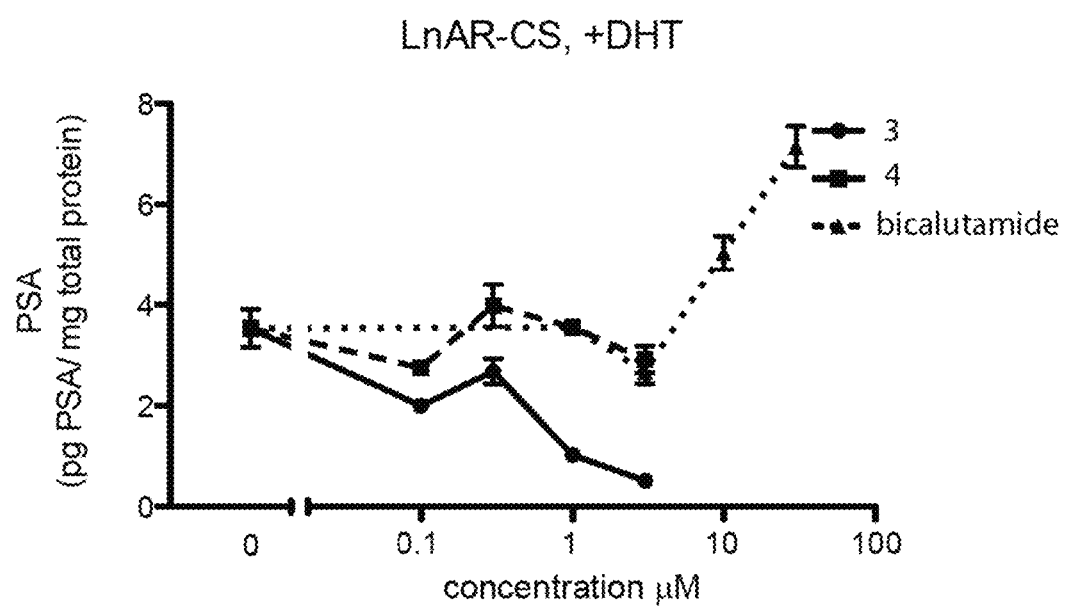

FIG. 14. Effects of polyamides on PSA secretion in hormone refractory LNAR-CS cells. Polyamide 3 inhibits secretion of PSA in hormone refractory prostate cancer cells. Polyamide 4 (control) has minimal effect. Bicalutamide fails to inhibit PSA secretion, further induces PSA expression upon DHT-stimulation.

FIG. 15. (A) Model of the glucocorticoid receptor response elements in the GILZ enhancer. (B) ball-and-stick models of polyamide 1, expected to bind the consensus GRE (SEQ ID NOS:5, 6), and 2, a mismatch (SEQ ID NOS:7, 8). (C) Structures of polyamide 1 and 2. Imidazole and pyrrole units are represented by closed and open circles, respectively. The isophthalic acid tail moiety is represented by a hexagon.

FIG. 16. Binding of 1 and 2 to the GRE in the GILZ enhancer. (A) Illustration of pKAM5 and partial sequence of the GILZ enhancer (SEQ ID NOS:9, 10). (B) Quantitative DNase I footprint titration experiments for polyamides 1 and 2 on the 5'-end-labeled PCR product of plasmid pKAM5: lane 1, intact DNA; lane 2, A reaction; lane 3, G reaction; lane 4, DNAse I standard; lanes 5-15, 1 pM, 3 pM, 10 pM, 30 pM, 100 pM, 300 pM, 1 nM, 3 nM, 10 nM, 30 nM, 100 nM polyamide, respectively. (C) Isotherm for 1 binding to the GRE1 and GRE2 sites. Polyamide 1 has a $K_a=1.9\pm0.8\times10^{10}$ for GRE1 and $K_a=8.8\pm1.8\times10^9$ for GRE2. (D) EMSA of glucocorticoid receptor binding to an oligonucleotide duplex containing the GILZ enhancer GRE1 and GRE2 in the presence of 1 and 2.

FIG. 17. Inhibition of dexamethasone-induced GILZ expression by 1 and 2. (A) Induction of GILZ mRNA in the presence of 1, 2, measured by quantitative real-time PCR. 1 inhibits expression of GILZ in a dose-dependent manner up to approximately 60% at 10 μM. 2 has a more modest effect. (B) Chromatin immunoprecipitation assays with anti-GR or mock antibody treatment expressed as fold-enrichment (specific/mock) of DNA sequences at the GILZ enhancer. GR occupancy at the GILZ enhancer is decreased in the presence of 1 (10 μM).

FIG. 18: (A) Illustration of the binding of an estrogen receptor (ER) to estrogen response elements (ARE) (SEQ ID NO:11) in the promoters and enhancers of target genes resulting in a modulation of the level of gene expression. (B) The ERE is targeted and bound by one or more pyrrole-imidazole containing polyamides that prevent or displace the receptor, modifying the expression of estrogen receptor regulated genes.

Figure 19:
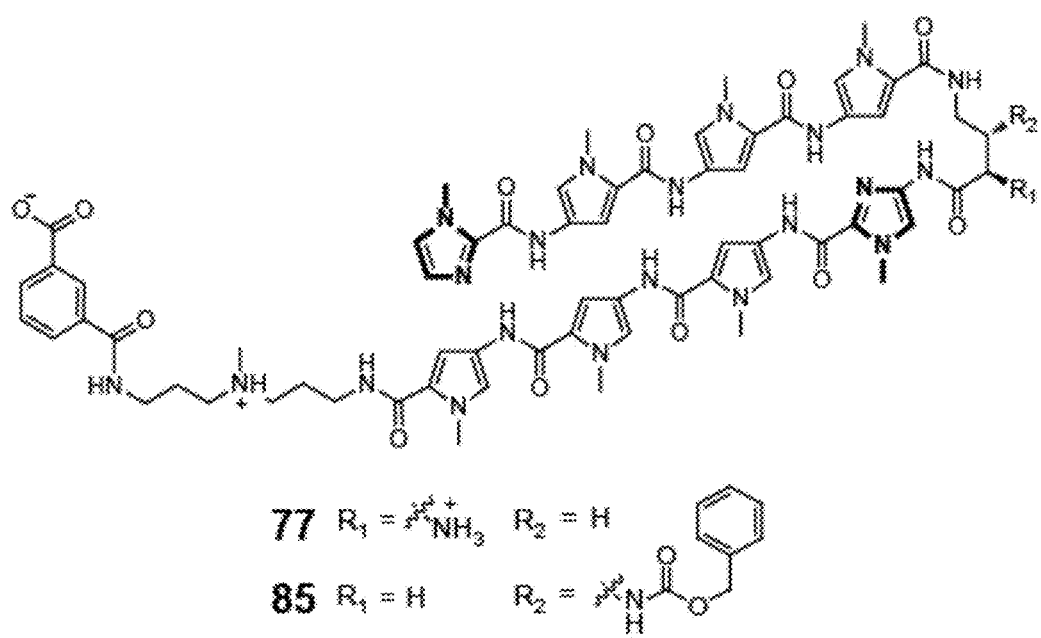

FIG. 19. Polyamides of certain embodiments of the invention are shown as structures 77 and 85.

FIG. 20. Global effects on RNAP2. Genome browser tracks of RPB1 occupancy from untreated, DHT treated, DHT+77 treated samples over (A) an AR driven gene, KLK3 (PSA), and (B) a housekeeping gene, GAPDH. (C) Genomic RNAP2 occupancy at transcription start sites show comparable levels of enrichment for nontreated and DHT treated samples. Samples treated with DHT+77 exhibited much lower occupancy. (D) Genomic RNAP2 occupancy at enhancer regions is largely unchanged between the three treatment conditions. (E) Immunoblot of RPB1 protein in LNCaP cells treated with 104 doxorubicin (dox) for 16 h, or 77 at 2 μM 10 μM, and 20 μM for 48 and 72 h. (F) Quantitative RT-PCR measurement of RPB1 transcript levels after LNCaP cells are treated with 10 μM 77 for the indicated times. Relative expression is normalized against nontreated cells. Data represent mean±s.d. of biological quadruplicates.

FIG. 21. (A) Cytotoxicity of 77 in LNCaP cells after incubation with 77 for 72 h. Data represent mean±s.d. IC50 is calculated from 3 independent experiments and the error is a 95% confidence intervals. (B) Cell viability at 24 h of LNCaP cells treated with varying concentrations 85 with and without proteasome inhibitor MG132 (3 μM, 24 h); proteasome inhibition reduces cytotoxicity of 85. (C) Immunoblot of RPB1 protein in LNCaP cells treated with 10 μM 85 for 12 h followed by 10 μM MG132 for 4 h. (D) Cytotoxicity of 85 in LNCaP cells incubated with 10% FBS or with 0.5% FBS for 24 h. Serum starvation decreases percent of cells in the S phase from 8.5% to 4.4% (SI FIG. 2). Data represent mean of biological triplicates and error bars represent s.d.

FIG. 22. (A) Induction of p53 target genes (GADD45A, MDM2, IGFBP3, P21, BAX) and DNA damage inducible transcript 3 (DDIT3), by 77 (10 μM) at 24 h, 48 h, and 72 h. Data represent the mean of 4 biological replicates and error bars represent s.d. (B) Alkaline comet assay of LNCaP cells treated with vehicle, dox (5 μM, 4 h), 77 (10 μM, 48 h). Error bars represents max and min, boxes represents the upper and lower quartiles and median. Representative comets for each treatment are shown. Effects of 77 are indistinguishable from the non-treated control, while dox treatment significantly increases comet-tail percent of DNA. p=0.00043. (C) DNA damage markers after treatment of LNCaP cells with 77. There is no evidence of phosphorylated DNA-PKcs, ATM, Chk2, p53 or γH2A.X. Accumulation p53 and PARP cleavage are observed. Data is representative of biological triplicates.

FIG. 23. Polyamide 77 demonstrates anti-tumor activity in prostate cancer xenografts. (A) Male immune-compromised mice were engrafted with LNCaP cells and observed until tumors reached ~100 mm3. Tumor bearing mice were then treated with 20 nmol 77 (n=12) or vehicle (n=13) by SC injections into the flank distal to the tumor once every three days for a total of three injections. Mice were euthanized and tumors resected and weighed two days after the final injection. Tumors from mice treated with 77 were smaller (mean: 112 mg, median: 94 mg, range: 47-201 mg) than those of vehicle treated mice (mean:310 mg, median: 292 mg, range: 173-440 mg). Error bars represents max and min, boxes represents the upper and lower quartiles and median. p=1.6E-5. (B) Serum PSA measured by ELISA pre- and post-treatment. Serum PSA is lower in the post-treatment serum of mice treated with 77 as compared to vehicle. p=0.024. (C) Selected tumors and histological stains of tumor cross-sections from mice treated with vehicle or 77. (D) Treatment of LNCaP tumor bearing mice with 77 increases serum uric acid as compared to vehicle controls and polyamide treated, non-tumor bearing mice. p=3.2E-9.

Figure 24:
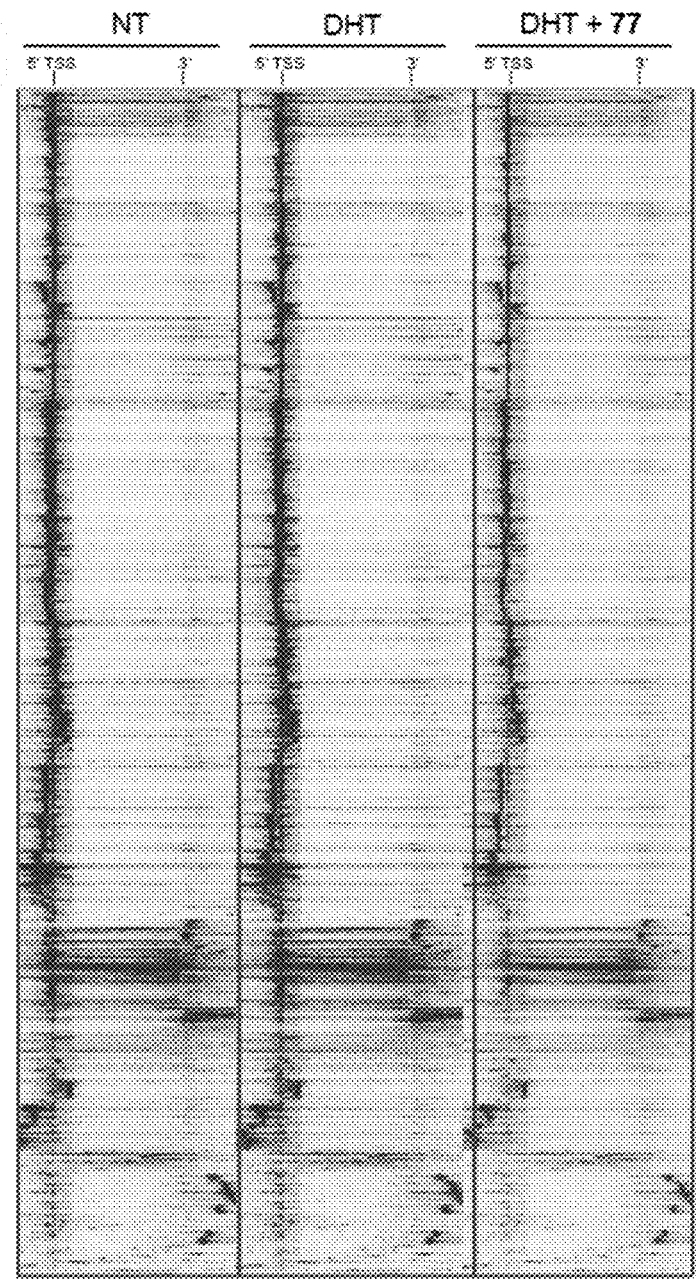

FIG. 24. Heat map of global distribution of RNAP2 over gene bodies.

FIG. 25. (A) Cytotoxicity of 77 and 85 in LNCaP cells after 24 h treatment. Although 77 demonstrates cytotoxicity at 72 h, minimal cytotoxicity is seen at 24 h. (B) DNA thermal stability analysis of 77 and 85 show comparable DNA binding of the two compounds. (C) Chemical structure of fluorescein conjugated form (86) of polyamide 85. (D) Addition of MG132 did not affect the cellular uptake of 86. (E) Serum starvation decreases the percent of LNCaP Cells in S phase.

Figure 26:
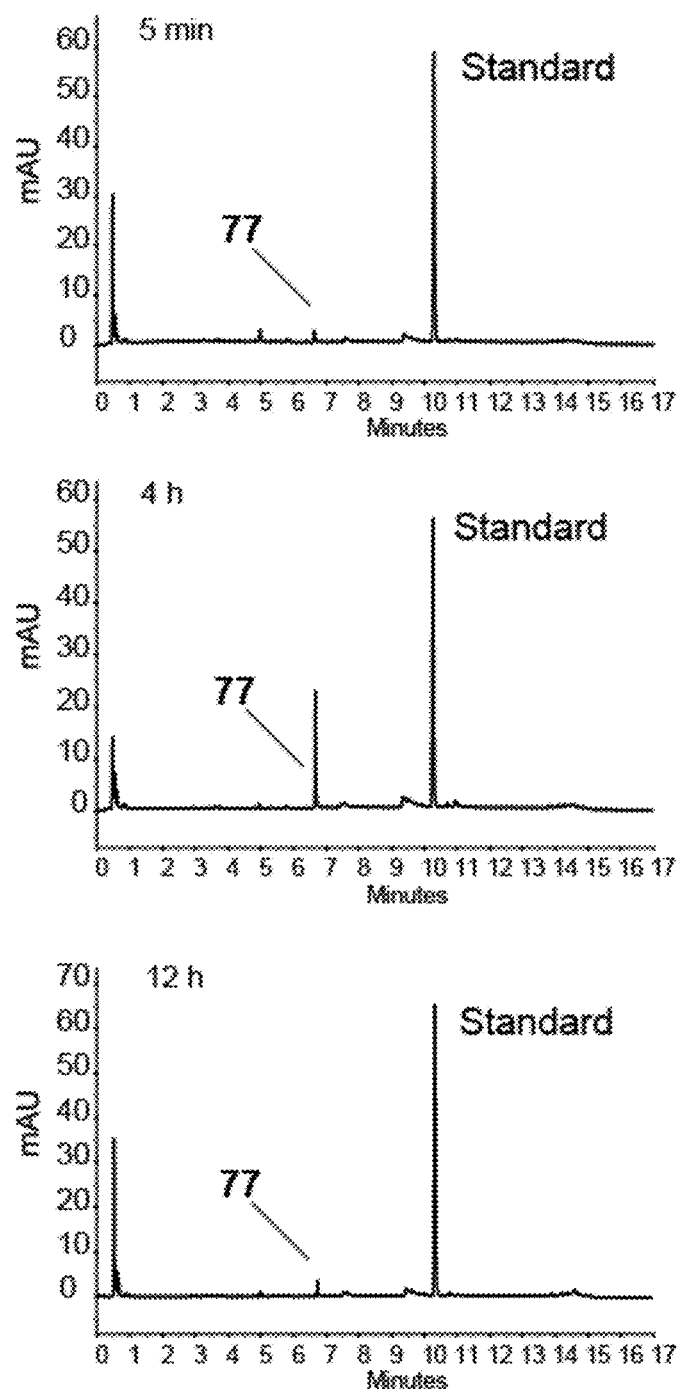

FIG. 26. Circulation study of 77 in C57BL/6J mice (n=4) at 5 min, 4 h, and 12 h post subcutaneous injection in 5% DMSO in PBS.

FIG. 27. Animal weights were measured at each injection of 77 and at the experiment endpoint (EP). (A) Weight measurements of tumor free male immunocompromised mice treated with 20 nmol of 77 once every 3 days for 3 injections (n=5). (B) Weight measurements of LNCaP tumor bearing male immunocompromized mice treated with 20 nmol of 77 once every 3 days for 3 injections (n=12). (C) Weight measurements of LNCaP tumor bearing male immunocompromized mice treated with vehicle (5% DMSO in PBS) once every 3 days for 3 injections (n=13). Experiments were end pointed 2 days after the last injection. Error bars represents max and min, boxes represents the upper and lower quartiles and median.

FIG. 28. Chemical structures. (A) Structures of polyamides 77-80. The compounds only vary by the amino substitution on the g-turn unit. (B) The preferred DNA binding sequence of the polyamide core. Polyamide 77 is shown bound to the sequence 5'-WGWWCW-3'. Closed circles represent imidazole units and open circles represent pyrrole units.

FIG. 29. Experiment set up of single dose weight curve experiments. (A) Male C57BL/6J mice were allowed to adapt to new cage settings for 3 days after arrival and then treated with compound. Animal weights were then monitored for 9 days. Humane endpoint was defined by visible signs of duress in the animals or weight loss in excess of 15% of original body weight. Weight curves of compounds (B) 77, (C) 79, (D) 78, and (E) 80.

FIG. 30. (A) Histopathology analysis of sacrificed animals showed primary organ damage in the kidney and liver for compounds 77, 79, and 80. Animals treated with 78 did not exhibit signs of organ damage. * represents n=1. +=mild damage, ++=moderate damage, +++=severe damage. (B) Liver and kidney histopathology of two representative animals treated with compounds 77-80 at 3 mg/kg. Liver: long gray arrow=hepatocellular apoptosis/necrosis, arrowheads=outline area of bridging hepatocellular necrosis/apoptosis. Kidney: short gray arrow=tubular epithelial karyomegaly, long gray arrow=tubular epithelial apoptosis/necrosis, short black arrow=tubular epithelial mitoses, long black arrow=tubular epithelial attenuation. (C) Serum levels of liver damage and kidney damage markers. Significantly elevated markers are shaded in gray. *n=2.

FIG. 31. Experiment set up of multi dose weight curve experiments. (A) Male C57BL/6J mice were treated with compound once every three days. Animal weights were then monitored for 9 days. Humane endpoint was defined by visible signs of duress in the animals or weight loss in excess of 15% of original body weight. (B) Weight curves of compounds 77-80. (C) Histopathology analysis of sacrificed animals after multiple injections of compounds 77-80 at 1 mg/kg. +=mild damage, ++=moderate damage, +++=severe damage. (D) Serum levels of liver damage and kidney damage markers after 3 SC injections of compounds 77-79. Significantly elevated markers are shaded in gray.

FIG. 32. Activity of 78 in LNCaP cells. (A) Nuclear uptake of 88 and 90. (B) Cellular cytotoxicity of 78 towards LNCaP cells after 72 hr incubation. (C) RPB1 protein decreases after treatment with 77 or 78 at 10 μM for 72 hr, or doxorubicin (D) at 1 μM for 24 hr. (D) Cellular level of p53 protein increases after treatment 77 or 78 at 10 μM for 72 hr, or D at 1 μM for 24 hr. (E) The p53 responsive genes p21, IGFBP3 and GADD45A are induced by 78 in a dose-dependent fashion (concentrations are 1, 3, 10 μM) after 72 hr treatment. (F) Alkaline comet assay shows no increase in genomic fragmentation after prolonged incubation with 78 (48 h, 10 μM). Error bars represent 90% range; boxes represents the upper and lower quartiles and median.

FIG. 33. Activity of 78 against LNCaP xenografts (A) timeline of treatment regimen. (B) Mouse weights throughout experiment. (C) Tumor weights at the experimental endpoint. Error bars represents maximum and minimum; boxes represents the upper and lower quartiles and median. p<0.01. (D) Serum chemistry analysis of wild type mice after 6 injections of 78. Serum levels of AST, ALT, total bilirubin, BUN, and creatinine were found to be within normal limits after compound treatment. (E) Hematological analysis of wild type mice after 6 injections of 78. The levels of white blood cells (WBC), red blood cells (RBC), hemoglobin (HGB), neutrophil, and lymphocytes were not significantly affected by polyamide treatment. Values represent average of 5 animals, errors are s.t.d.

FIG. 34. DNA thermal stabilization analysis of compounds 77-80.

Figure 35:
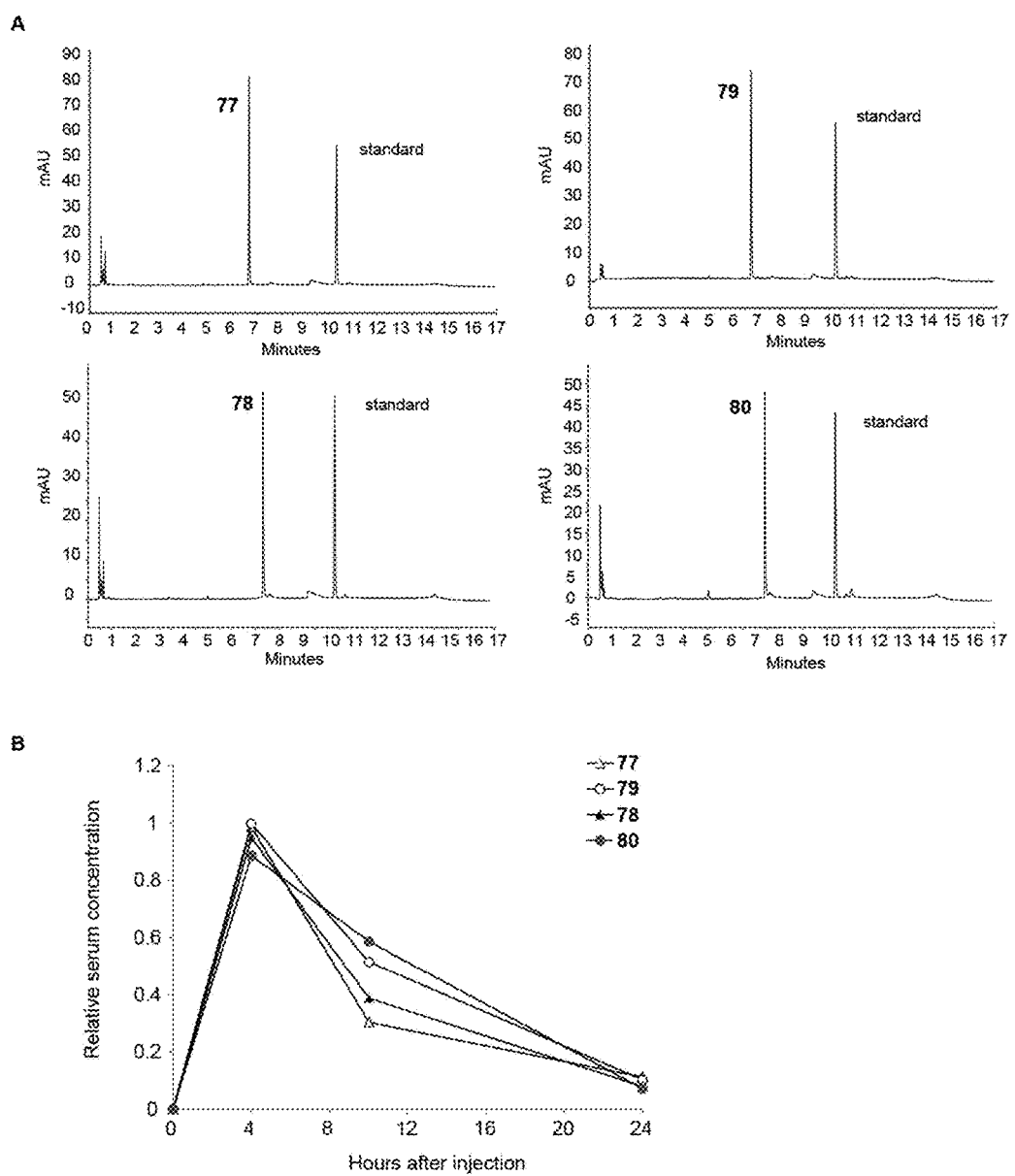

FIG. 35. (A) Analytical HPLC traces of compounds 77-80 in the serum 4 hr after injection. (B) Relative serum levels of compounds 77-80 at 4 hr, 10 hr, and 24 hr after a single subcutaneous injection of each compound at 10 mg/kg.

Figure 36:
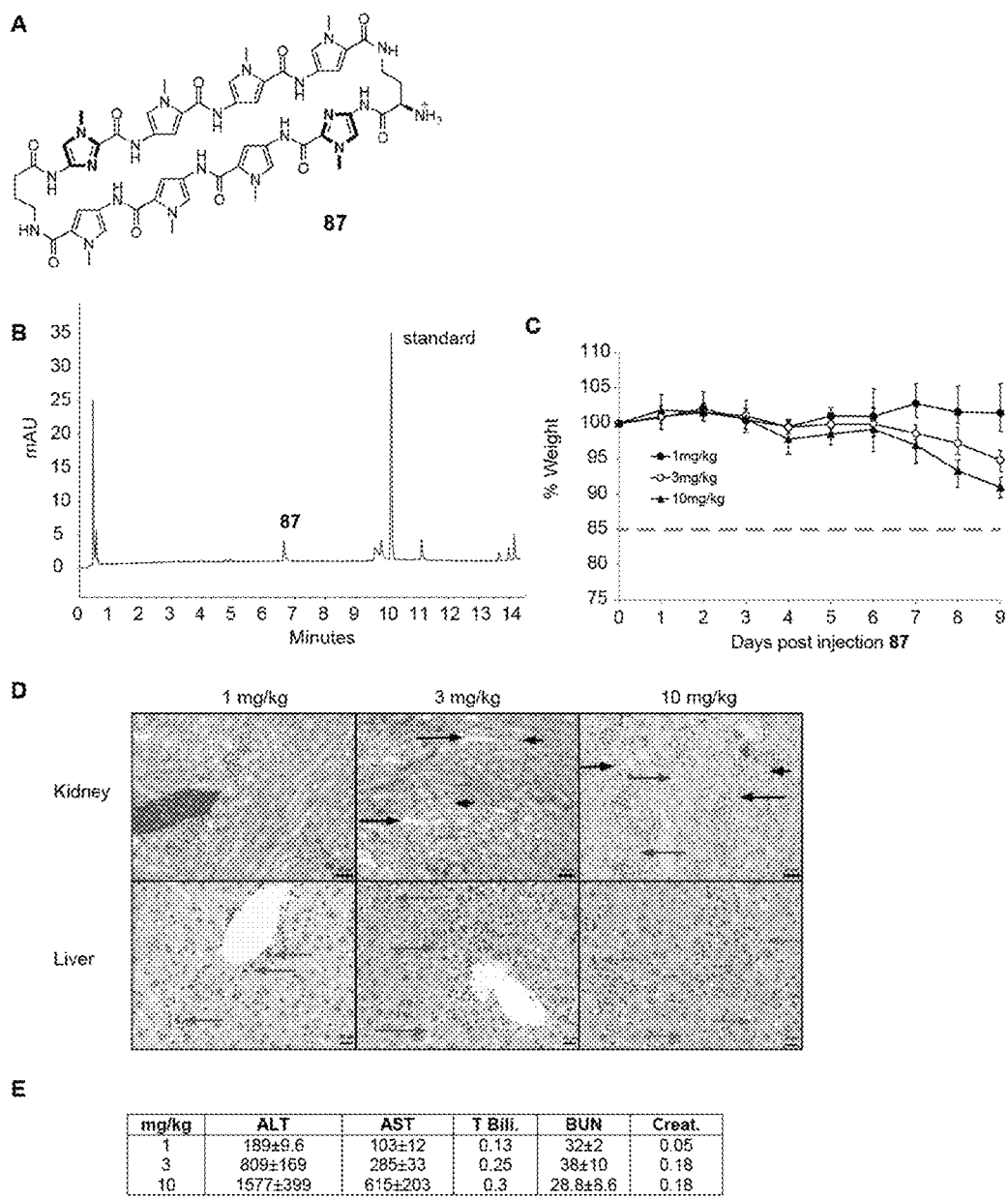

FIG. 36. Characterization of a cyclic polyamide targeting the sequence 5'-WGWWCW-3'. (A) Chemical structure of compound 87. (B) Serum circulation of 87 4 hr after SC injection. (C) Changes in animal weights after a single SC injection of 87 at the indicated concentrations. (D) Kidney and liver histology of sacrificed animals after 9 days of monitoring. (E) Serum chemistry of animals treated with 87.

Liver: long gray arrow=hepatocellular apoptosis/necrosis, arrowheads=outline area of bridging hepatocellular necrosis/apoptosis. Kidney: short gray arrow=tubular epithelial karyomegaly, long gray arrow=tubular epithelial apoptosis/necrosis, short black arrow=tubular epithelial mitoses, long black arrow=tubular epithelial attenuation.

Figure 37:
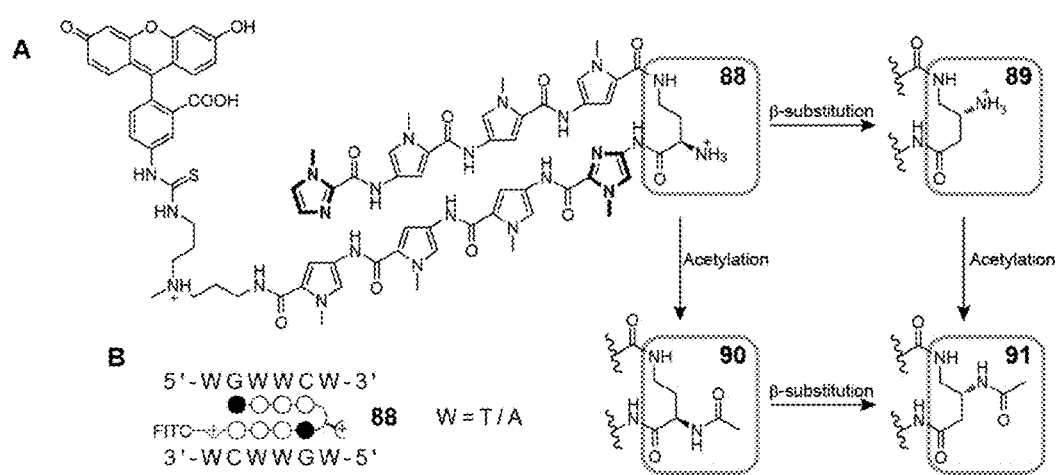

FIG. 37. Chemical structures. (A) Structures of polyamides 88-91. The compounds only vary by the amino substitution on the g-turn unit. (B) The preferred DNA binding sequence of the polyamide core. Polyamide 88 is shown bound to the sequence 5'-WGWWCW-3'. Closed circles represent imidazole units and open circles represent pyrrole units.

Figure 38:
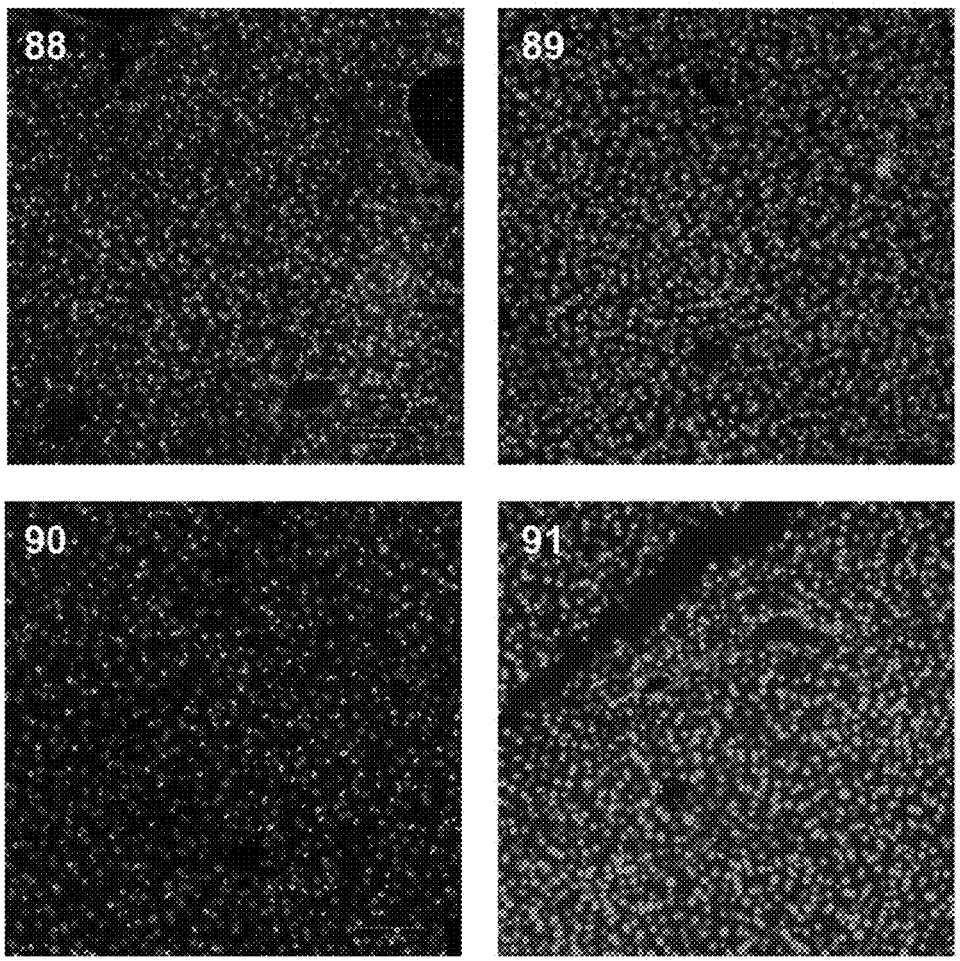

FIG. 38. Nuclear localization of compounds 88-91 in the liver 24 hr after SC injection.

Figure 39:
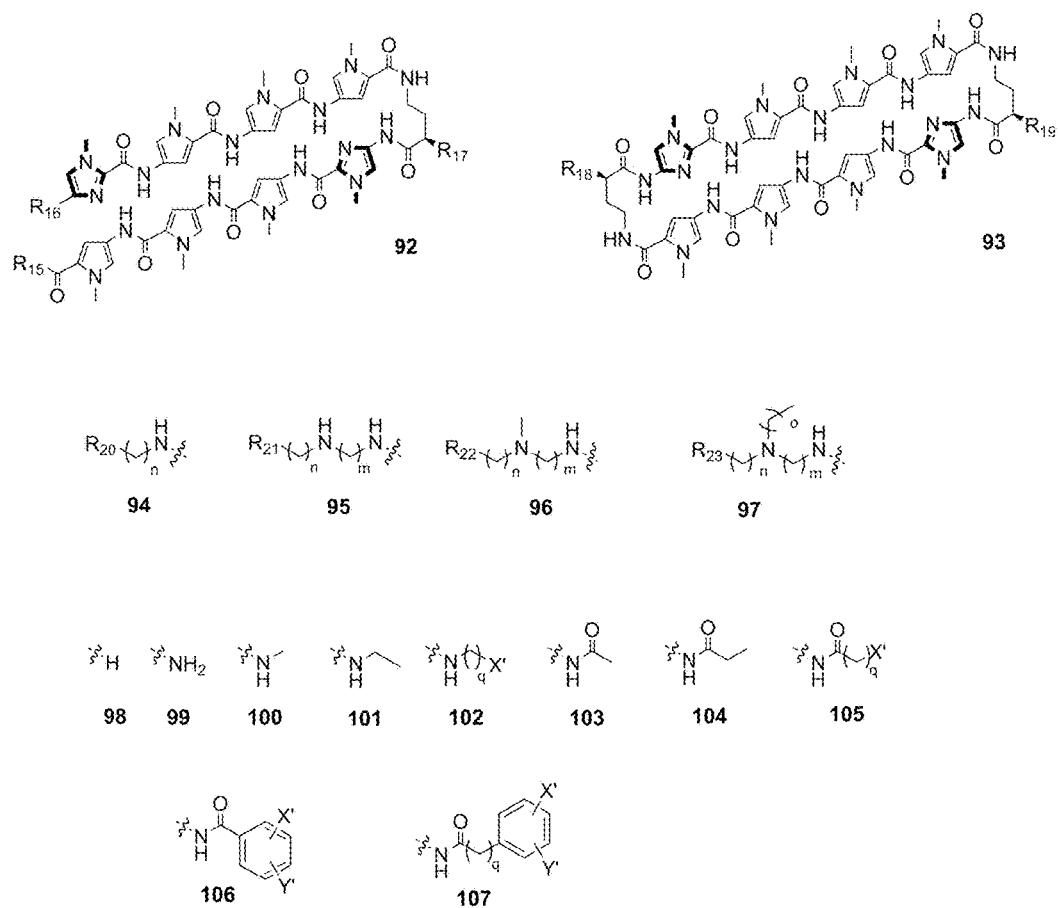

FIG. 39: Polyamides of certain embodiments of the invention are shown as structures 92 and 93. $R_{15}$ is selected from structures 94-97, wherein each m, n, o is independently selected from 1-10. Each $R_{16}$-$R_{23}$ is independently selected from structures 98-107, wherein each q is independently selected from 1-10, and wherein each X' and Y' are independently selected from H, OH, SH, $CH_3$, $CH_2CH_3$, $NH_2$, $NO_2$, COOH, COOMe, COOEt, F, Cl, Br, or I.

5.0 DETAILED DESCRIPTION OF THE INVENTION

The present invention relates to compositions capable of modulating the activity of an ARE, a GRE and/or an ERE. In certain embodiments, a composition of the invention comprises a polyamide, preferably a polyamide capable of binding an ARE, a GRE and/or an ERE in DNA, for example, in genomic DNA. A polyamide of the invention, in certain embodiments, is capable of modulating the expression of a gene that is regulated by an ARE, a GRE and/or an ERE. In certain preferred embodiments, a polyamide of the invention is capable of entering a cell and modulating the expression of a gene that regulated by an ARE, a GRE and/or an ERE.

5.1 Polyamides of the Invention

A polyamide of the invention, in certain embodiments, has structure 1 (FIG. 1). A polyamide of structure 1 may be one molecule, for example, if R1, R5, R3, R4 are linked through a turn of any one of structures 4-6, or two molecules, for example, a homodimer or a heterodimer. A monomer of a polyamide of structure 1 is capable of binding DNA independently of another monomer of a polyamide of structure 1 but preferably as part of a homodimer or heterodimer with another monomer of a polyamide of structure 1. Monomers of a homodimer or heterodimer of structure 1 are capable of binding DNA so that the monomers bind DNA side-by-side to each other, or within close proximity (for example, at sites that are separated by less than 10 base pairs, or by less than 50 base pairs).

Polyamides of the invention in certain embodiments comprise a structure 1, wherein each X is independently selected from CH, N, or OH (each p independently selected from 0 and 1), wherein each $R_2$ is independently selected from H, a $C_{1-10}$ alkyl, a $C_{1-10}$ alkenyl, a $C_{1-10}$ alkynyl, —$(CH2)_q$-NH—$R_6$ (each q independently selected from 1-10). In structure 1, each pyrrole unit of structure 2 may be independently replaced by a beta-alanine of structure 3. Each $R_3$ and $R_4$, and/or each $R_1$ and $R_5$ in structure 1 may be covalently linked by a turn of any one of structures 4-6 to form a hairpin- or a cyclic-shaped molecule. Any $R_2$ may be covalently linked to another $R_2$ to form an H- or U-shaped molecule. Each $R_7$, $R_8$ and $R_9$ in structures 4 and 5 may be independently selected from an R or S isomer, and is independently selected from structures 7-17 (each s independently selected from 1-10). Each $R_1$ and $R_4$ (e.g., in structure 1), and each $R_{10}$ (e.g., in structures 14 and 16), is independently selected from structures 18 (each u independently selected from 0 and 1), with each A independently selected from structure 21. Each $R_3$ and $R_5$ (e.g., in structure 1), each $R_6$ (e.g., in $R_2$), and each $R_{11}$ (e.g., in structures 15 and 17), is independently selected from structures 19 and 20 (each v and w independently selected from 0 and 1), with each A' independently selected from structures 22, and with each Z independently selected from structures 23 and 24. Each $R_{12}$ is independently selected from structures 25-54 (each d, e, f, h and j independently selected from 1-10), with each y independently selected from structures 55-57. Each t is independently selected from 1-10. Each $R_{13}$ is independently selected from structures 58-74 (each g and e independently selected from 1-10). In $R_{12}$ and $R_{13}$, each $R_{14}$ represents one, two, three, four, or five sidechains of the ring (up to the maximum number) with each $R_{14}$ being independently selected from H, OH, SH, $CH_3$, $NH_2$, halogen, F, Cl, Br, or I, and each amide linkage of structure 75 that occurs in structures 42-59 may be independently replaced by a thiourea linkage of structure 76. Polyamides of the current invention, in certain preferred embodiments, comprise any one or more of structures 77-84.

Polyamides of the invention in certain embodiments comprise any one or more of structures 92 and 93, wherein $R_{15}$ is selected from structures 94-97, wherein each m, n, o is independently selected from 1-10. Each $R_{16}$-$R_{23}$ is independently selected from structures 98-107, wherein each q is independently selected from 1-10, and wherein each X' and Y' are independently selected from H, OH, SH, $CH_3$, $CH_2CH_3$, $NH_2$, $NO_2$, COOH, COOMe, COOEt, F, Cl, Br, and I.

Polyamides of the present invention may be synthesized by any method known in the art, for example, by solid phase methods using compounds such as Boc-protected 3-methoxypyrrole, imidazole, pyrrole aromatic amino acids, and alkylated derivatives thereof, which are cleaved from the support by aminolysis, deprotected (e.g., with sodium thiophenoxide), and purified by reverse-phase HPLC, as well known in the art. The identity and purity of the polyamides may be verified using any of a variety of analytical techniques available to one skilled in the art such as $^1$H-NMR, analytical HPLC, and/or matrix-assisted laser-desorption ionization time-of-flight mass spectrometry (MALDI-TOF MS-monoisotropic). A tail-polyamide of the invention, in certain embodiments, may also comprise a protective group useful for purposes of polyamide synthesis, in certain other embodiments, a tail-polyamide does not comprise a protective group. Useful protective groups are known to those of skill in the art.

The aliphatic functionalities of linkable units can be provided, for example, by condensation of β-alanine or dimethylaminopropylamine during synthesis of the polyamide by methods well known in the art. Linkable units are typically supplied as amino acids, desamino acids, or descarboxy amino acids prior to amide bond formation by condensation methods well known in the art to form linking amide groups. The term "amino acid" refers to an organic molecule containing both an amino group ($NH_2$) and a carboxylic acid (COOH). The term "desamino" refers to an amino acid from which the amino functionality has been removed. The term "descarboxy" refers to an amino acid from which the carboxylic acid functionality has been removed. The term "chemical probe" refers to chemical functionalities having properties that facilitate location and identification of polyamides functionalized (i.e., covalently bonded) by such chemical probes. A chemical probe does not include fluorescein. Methods of conjugating chemical probes to polyamides of the invention are well known in the art.

Tail-polyamides may be synthesized by any method known in the art, including methods discussed herein. Methods of synthesizing organic compounds that are useful in synthesizing a tail-polyamide of the invention are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.2 Modulation of Gene Expression Using Polyamides of the Invention

A polyamide of the invention is useful for modulating the expression of a gene. A polyamide of the invention in certain embodiments is capable of modulating the expression of a gene in a cell, preferably a living cell, and most preferably a cell in a higher organism, for example, a human, an animal, a dog, a cat, a pet, a farm animal, a cow, a pig, a chicken, a fish, or any other animal, or a plant. A polyamide of the invention in certain embodiments is capable of entering a cell and preferably the nucleus of the cell. In certain embodiments, a polyamide of the invention is useful for modulating gene expression in a cell in culture. In certain other embodiments, a polyamide of the invention is useful for modulating gene expression in a patient to ameliorate a disease symptom and/or to modulate a physiological process, for example, cell behavior, cell growth, cell secretion, cell signaling, cell death, or any other process.

A polyamide of the present invention is capable of binding double stranded (i.e., duplex) DNA at a specific sequence (i.e., the target DNA sequence or target sequence or target site) with high affinity and selectivity. A recitation of a sequence of DNA herein contemplates the recited single-stranded DNA, the complementary (i.e., Watson-Crick) sequence, and the duplex molecule comprising the recited and complementary strands of DNA.

A target site for a polyamide of the invention is an ARE, a GRE and/or an ERE. An ARE, in certain embodiments, comprises a consensus sequence of 5'-GGWACANNNTGT-TCT-3' (SEQ ID NO:12) (with N=A, T, C, or G; and W=A or T) that is typically 15 base pairs in length and that is typically nearly palindromic. An ARE, in certain embodiments, comprises of two six base pair segments separated by a 3 base pair spacer. In certain other embodiments, an ARE comprises a consensus sequence of 5'-NGWACWNNNTG-TYCN-3' (SEQ ID NO:13) (with N=A, T, C, or G; and W=A or T; and Y=T, G or A). In certain other embodiments, an ARE comprises six base pair half sites of the sequences 5'-TGTTCT-3', 5'-NGWACW-3' and 5'-TGTYCN-3' (with N=A, T, C, or G; and W=A or T; and Y=G or A), which may be a functional ARE without the presence of the full 15 base pair ARE present. Background on the ARE can be found in Roche P J et al., A consensus DNA-binding site for the androgen receptor. Mol. Endocrinol. 1992 December; 6(12): 2229-35; Massie C E et al., New androgen receptor genomic targets show an interaction with the ETS1 transcription factor. EMBO Rep. 2007 September; 8(9):871-8, which are incorporated herein by reference.

A GRE, in certain embodiments, comprises the sequence 5'-GGTACANNNTGTTCT-3' (SEQ ID NO:1) or a half-site of the sequence 5'-TGTTCT-3'. An ERE, in certain embodiments, comprises a 13 base pair sequence 5'-GGT-CANNNTGACC-3' or a half site of the sequence 5'-NG-GTCA-3' (with N=A, T, C, or G). ER can also bind to six base pair half sites of the sequences, which can still be a functional ERE without the presence of a full 13 base pair ERE sequence. Background on the ERE can be found in Peale F V Jr et al., Properties of a high-affinity DNA binding site for estrogen receptor. Proc Natl Acad Sci USA. 1988 February; 85(4):1038-42, and Carroll J S et al., Genome-wide analysis of estrogen receptor binding sites. Nat. Genet. 2006 November; 38(11):1289-97, which are incorporated herein by reference.

Proteins of the nuclear hormone receptor family of transcription factors have structures consisting of a ligand binding domain, an amino-terminal domain, a hinge domain, and a DNA binding domain. The DNA binding domain is largely conserved between the different nuclear hormone receptors, contains two modules of zinc coordinated by four cysteines, and is related to the classical Cys-2-His-2 zinc finger motifs of DNA binding proteins.

Most nuclear hormone response bind as homo- or hetero-dimmers to their respective response elements on DNA at particular gene regulatory sequences for their target genes. The steroid receptor subgroup, including androgen receptor, estrogen receptor, glucocorticoid receptor, progesterone receptor, and mineralocorticoid receptor, each bind typically as homo-dimers. The response elements typically consist of two six base pair sequences, "half-sites," that are separated by an intervening spacer sequence of one to five, usually three, nucleotides. For most nuclear receptor response elements, the first and sixth base pairs are both either A-T or T-A pairs, moving from 5' to 3'. The second and fifth are G-C and C-G, respectively, moving from 5' to 3'. The nucleotides at the third and fourth positions vary depending on the particular receptor, and the particular response element. The ARE and GRE half sites are often of the sequence 5'-TGT-TCT-3',5'-NGWACW-3', or 5'-TGT(G/T/A)CN-3', where W=A or T, and N=A, T, G, or C. The ERE half sites are often of the sequence 5'-NGGTCA-3'. The half sites for the response elements are often oriented as palindromes or semi-palindromes about the intervening spacer sequence. (Khorasanizadeh S, Rastinejad F. Nuclear-receptor interactions on DNA-response elements. Trends Biochem Sci. 2001 June; 26(6):384-90.)

DNA binding polyamides composed of eight heterocyclic rings of imidazole or pyrrole linked by amide linkages can be designed to bind to the six base pair half sites of nuclear receptors. A polyamide could be designed to bind at one or both half sites for a particular response element, or two different polyamides could be designed to bind at each half site for a particular response element, or two or more polyamides could be designed to bind at one or more of the response elements for a nuclear receptor at different loci in the genome.

A DNA binding polyamide that is targeted to bind to an ARE, GRE, or ERE, or another binding site for some other nuclear receptor, includes in its structure an imidazole opposite a pyrrole in the minor groove at the second base pair (a G-C pair) of the six base pair half site such that the exocyclic amine of the guanine can hydrogen bond with the lone pair nitrogen of the imidazole at this position. Additionally, such a polyamide would also include in its structure a pyrrole opposite an imidazole at the fifth base pair (a C-G pair), likewise so that the exocyclic amine of the guanine can hydrogen bond with the lone pair nitrogen of the imidazole at this position. The imidazole or pyrrole content at positions three and four of the six-base pair half site are determined by the particular base pair sequence that is to be targeted such that a G-C pair is presented with an imidazole-pyrrole pair, a C-G pair is presented with a pyrrole-imidazole pair, and either an A-T or T-A is presented with a pyrrole-pyrrole pair. For example, a polyamide targeted to bind an ERE containing a half site of the sequence 5'-AGGTCA-3' would in part comprise an imidazole opposite a pyrrole at the G-C base pair at the third position of the half site. This polyamide would present a pyrrole opposite a pyrrole at the T-A base pair at the fourth position. In another example, a polyamide targeted to an ARE containing a half site of the sequence 5'-TGTGCA-3' would in part comprise a pyrrole opposite a pyrrole at the third position T-A base pair, and an imidazole opposite a pyrrole at the G-C base pair at the fourth position. In another example, a polyamide targeted to a GRE containing the half site of the sequence 5'-TGTTCT-3' would in part comprise a pyrrole opposite a pyrrole at both the T-A base pairs at the third and fourth positions. For polyamides targeted to bind at such half sites, the tail and turn of the polyamide lie over the first and sixth positions of the half site.

A polyamide of the present invention is useful to modulate gene expression, for example, by interfering with RNA polymerase II activity or by activating p53 signaling.

As used herein, "subnanomolar affinity" means binding that is characterized by a dissociation constant, $K_d$, of less than 1 nM, as measured by DNase I footprint titration. In certain preferred embodiments, a polyamide of the present invention is characterized by subnanomolar affinity for ARE, GRE and/or ERE. As used herein, the "selectivity" of the binding of a polyamide to an ARE, GRE and/or ERE is the ratio of the dissociation constant, $K_d$, as measured by DNase I footprint titration, when binding the polyamide to a mismatch DNA sequence divided by the corresponding dissociation constant when binding the polyamide to the ARE, GRE and/or ERE. In certain preferred embodiments, polyamides of the present invention are characterized by a selectivity of 5 or greater, or about 5 or greater, or 10 or greater, or about 10 or greater, or 20 or greater, or about 20 or greater, or 50 or greater, or about 50 or greater, or 100 or greater, or about 100 or greater.

In certain preferred embodiments, a polyamide of the invention has at least 5-fold greater affinity for an ARE, GRE and/or ERE than for a site differing from the target site by one, two, or three nucleotides, or at least 10-fold, or at least 20-fold, or at least 50-fold, or at least 100-fold, or at least 200-fold, or at least 500-fold. Preferably, a polyamide of the invention will interact with an ARE, GRE and/or ERE with an affinity, as measured by DNase footprint titration, of less than 100 nM, or preferably less than 50 nM, or preferably less than 25 nM, or preferably less than 15 nM, or preferably less than 10 nM, or preferably less than 5 nM, or preferably less than 1 nM, or preferably less than 0.2 nM, or preferably less than 0.1 nM.

In certain embodiments, a polyamide of the invention has a binding affinity $K_d$ for an ARE, GRE and/or ERE that is greater than $10^8 M^{-1}$, or preferably greater than $2 \times 10^8 M^{-1}$, or preferably greater than $5 \times 10^8 M^{-1}$, or preferably greater than $10^9$ $M^{-1}$, or preferably greater than $2 \times 10^9$ $M^{-1}$, or preferably greater than $5 \times 10^9$ $M^{-1}$, or preferably greater than $10^{10}$ $M^{-1}$, or preferably greater than $2 \times 10^{10}$ $M^{-1}$ or preferably greater than $5 \times 10^{10}$ $M^{-1}$, or preferably greater than $10^{11}$ $M^{-1}$. The reduction in affinity of a polyamide of the invention to an ARE, GRE and/or ERE with a mismatch of one, two or three nucleotides, when compared to ARE, GRE and/or ERE without a mismatch, in certain embodiments, is at least 3 fold, at least 5 fold, at least 10 fold, at least 20 fold, at least 50 fold, or at least 100 fold, or more. The affinity of a polynucleotide of the invention to DNA (or another molecule) can be determined by any method known in the art and as discussed herein.

A polyamide of the invention, in certain embodiments, can be examined to determine its affinity for its target DNA sequence and at mismatched and random sites, if desired. The affinity can be determined using DNase footprint analysis, as discussed herein. A polyamide of the invention, in certain embodiments, can also be examined to determine its ability to modulate gene expression, for example, by using an ARE, GRE and/or ERE involved in regulating the expression of a gene. For example, a polyamide may be administered to cells in culture at varying concentrations (e.g., at 0.2 µM, 0.5 µM, 1 µM, 2 µM, 5 µM, 10 µM, and 25 µM) and the expression of a gene that depends on an ARE, GRE and/or ERE may be determined by measuring levels of mRNA (messenger RNA) compared to mRNA levels in the absence of the polyamide. The analysis may be carried out, for example, as discussed in the examples below. An analysis of a polyamide's ability to modulate gene expression may be carried out in different cell types, for example, as described in Edelson et al., 2004, Nucleic Acids Res. 32:2802-2818. Other methods to analyze a polyamide's ability to modulate gene expression include the use of luciferase, protein quantitation, observing morphological and/or phenotypic changes, which are known to those of skill in the art.

Methods for the analysis of polyamides' ability to bind DNA and to modulate gene expression are further discussed, for example, in U.S. Pat. Nos. 7,087,378; 7,049,061; 6,958, 240; 6,673,940; 6,660,255; 6,635,417; 6,559,125; 6,555, 692; 6,545,162; 6,506,906; 6,472,537; 6,303,312; 6,143, 901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.3 Polyamides of the Current Invention as Research Tools

A polyamide of the invention, in certain embodiments, may be used as a research tool. For example, a polyamide of the invention may be used to modulate the expression of genes involved in a disease in cell culture or in an animal, for example, by down-regulating a gene so that the cells or the animal exhibits one or more traits of the disease. Following such modulation, a drug candidate may be tested in the cell culture and/or the animal to determine if the drug candidate is capable of compensating for the effects of gene modulation.

In certain other embodiments, a polyamide may be used to test the effectiveness of analytical techniques in a cell and/or an animal, for example by modulating gene expression and by testing the technique's ability to detect the effects thereof.

5.4 Therapeutic Applications of Polyamides of the Current Invention

A polyamide of the current invention, in certain embodiments, may be used in the treatment or prevention of a disease or condition in humans, animals and/or plants. It is contemplated that these compounds may be used independently or in conjunction with inactive excipients or active ingredients. As used herein, the term "agent" refers to compounds of the invention or compositions thereof comprising active and/or inactive ingredients.

In certain embodiments, polyamides of the invention may be used to modulate the expression of a gene, the expression of which depends at least in part on an ARE, GRE and/or ERE. In certain embodiments, polyamides of the invention may be used to modulate a gene with one, two, three, four, five, six or more AREs, GREs and/or EREs in a regulatory sequence of the gene, for example, in a promoter of the gene or an enhancer of the gene. A regulatory sequence of a gene may be within the gene (for example, in an intron, or in a 5 prime or 3 prime untranslated region), 5 prime (upstream) of the gene (for example, as part of a promoter that is located upstream of, and adjacent to or close to, the transcription initiation site), or 3 prime (downstream) of the gene (for example, 3 prime of the transcription termination site).

In certain embodiments, polyamides of the invention may be used to modulate the expression the PSA gene (prostate specific antigen), the klk2 gene, the tmprss2 gene, the DHCR24 gene, the LOC89944 gene, the NNMT gene, the GSTM1 gene, the UNC13 gene, the BICD1 gene, the ENTPD5 gene, the PFKFB3 gene, the ARL7 gene, the F112378 gene, the ATP2C1 gene, the C20orf167 gene, the SLC37A1 gene, the DOK4 gene, the FLJ14249 gene, the FLJ38482 gene, the TMEPAI gene, the KLK3 gene, the ASAH1 gene, the UNC5H2 gene, any gene listed in Table 3 (see below), any gene listed in Table 4 (see below). In certain embodiments, a polyamide of the present invention may be used to modulate gene expression, for example, by interfering with RNA polymerase II activity or by activating p53 signaling.

In certain embodiments, polyamides of the invention may be used to modulate the expression of a gene with an ARE, for example, a gene listed in Massie C E et al., New androgen receptor genomic targets show an interaction with the ETS1 transcription factor. EMBO Rep. 2007 September; 8(9):871-8; Bolton E C et al., Cell- and gene-specific regulation of primary target genes by the androgen receptor. Genes Dev. 2007 Aug. 15; 21(16):2005-17, which are incorporated herein by reference for any purpose. In certain embodiments, polyamides of the invention may be used to modulate the expression of a gene with an ERE, for example, a gene listed in Carroll J S et al., Genome-wide analysis of estrogen receptor binding sites. Nat. Genet. 2006 November; 38(11):1289-97, which is incorporated herein by reference for any purpose.

In certain embodiments, polyamides of the invention may be used to modulate the expression of a gene that is expressed in a tissue or organ, but that is not expressed in other tissues or organs, or that is expressed in other tissues at significantly lesser levels (for example, less than 20 percent, or less than 10 percent, or less than 5 percent), in other words a tissue-specific gene. A tissue-specific gene may be expressed in the prostate (prostate-specific gene).

In certain embodiments, polyamides of the invention may be used to treat a disease. "Treating" as used herein refers to alleviation of at least one symptom associated with a disease (for example, cancer), or halt of further progression or worsening of such disease, or prevention or prophylaxis of such disease. In certain embodiments, polyamides of the invention may be used to treat cancer, prostate cancer, a prostate-specific disease, hair-loss or alopecia, male-pattern hair loss, breast cancer, lung cancer, brain cancer, bone cancer, adrenal cancer, cervical cancer, esophageal cancer, eye cancer, myeloma, neuroblastoma, retinoblastoma, laryngeal cancer, sarcoma, skin cancer, pancreatic cancer, retinoblastoma, throat cancer, testicular cancer, uterine sarcoma, vaginal cancer, anal cancer, melanoma, neurofibromatosis, oral cancer, osteosarcoma, pituitary cancer, thyroid cancer, stomach cancer, lymphoma, gallbladder cancer, colon cancer, Kaposi sarcoma, Hodgkin disease, kidney cancer, leukemia, liver cancer, lung cancer, inflammatory diseases or diseases involving inflammation, diseases or conditions affecting fertility, ovarian cancer, colorectal cancer, endometrial cancer, osteoporosis, neurodegenerative diseases, cardiovascular disease, insulin resistance, lupus erythematosus, endometriosis, obesity, metabolic diseases, or any other disease involving the expression of a gene that is regulated by an ARE, GRE and/or ERE.

A polyamide of the invention, in certain embodiments, may be delivered to a patient in any way known in the art. The particular delivery mode selected will depend upon the polyamide selected, the condition being treated, the severity of the condition, whether the treatment is therapeutic or prophylactic, and the dosage required for efficacy. Therapeutic delivery of polyamides of the invention may be practiced using any mode of administration that is medically acceptable, meaning any mode that produces effective levels of the active compounds without causing clinically unacceptable adverse effects. Any dosage forms containing effective amounts are well within the bounds of routine experimentation and therefore, well within the scope of the instant invention. A therapeutically effective dose may vary depending upon the route of administration and dosage form. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the agent in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

Direct administration of a polyamide of the present invention to a designated site may be preferred for some methods provided herein. For example, treatment with a polyamide via topical administration in and around affected areas may be performed. In still other embodiments, a polyamide may be delivered by injection directly into the tissue with, for example, a biopsy needle and syringe.

Systemic administration may be preferred in some instances such as, for example, if the subject is known to have or is suspected of having metastases. In this embodiment, all tumor sites, whether primary or secondary, may receive the polyamide. Systemic delivery may be accomplished through for example, oral or parenteral administration Inhalation may be used in either systemic or local delivery, as described below.

A polyamide of the invention, in certain embodiments, is administered in therapeutically effective amounts. A therapeutically effective amount is an amount sufficient to delay the onset of, inhibit the progression of, or halt altogether the particular condition being treated. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. A therapeutically effective dose results in amelioration of at least one undesirable symptom. It is preferred generally that a maximum dose be used, that is, the highest safe dose according to sound medical judgment. Dosing amounts, dosing schedules, routes of administration and the like can be selected so as to affect bio-activity of the present compounds. Such determinations are routine and well known to one of ordinary skill in the art.

A therapeutically effective amount typically varies from 0.01 mg/kg (weight of polyamide over weight of patient) to about 1000 mg/kg, preferably from about 0.1 mg/kg to about 200 mg/kg, and most preferably from about 0.2 mg/kg to about 20 mg/kg, in one or more dose administrations daily, for one or more days. In some embodiments, a polyamide is administered for more than 7 days, more than 10 days, more than 14 days, or more than 20 days. In still other embodiments, a polyamide is administered over a period of weeks, or months. In still other embodiments, a polyamide is delivered on alternate days. For example, the polyamide is delivered every two days, or every three days, or every four days, or every five days, or every six days, or every week, or every month.

A polyamide of the invention, in certain embodiments, is administered in prophylactically effective amounts. In these embodiments, a polyamide is administered in an amount effective to prevent the development of an abnormal or undesirable condition or disease. For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow or halt the development of or the progression of a cell mass such as, for example, a tumor. As used in the embodiments, "inhibit" embraces all of the foregoing.

For example, in connection with methods directed to inhibition of mammalian cell proliferation, a therapeutically effective amount will be an amount necessary to extend the dormancy of micrometastases or to stabilize any residual primary tumor cells following surgical or drug therapy.

Compositions presented herein may include DNA-binding polymers of the invention in combination with any standard physiologically and/or pharmaceutically acceptable carrier known in the art. The term "pharmaceutically acceptable carrier" as used herein means one or more compatible solid or liquid fillers, diluents or encapsulating substances which are suitable for administration to a subject. The term "carrier" denotes an organic or inorganic ingredient, natural or synthetic, which with the DNA-binding polymer is combined to facilitate delivery of the composition. The components of the pharmaceutical compositions also are capable of being co-mingled with the molecules of the present invention, and with each other, in a manner so as to not substantially impair the desired pharmaceutical efficacy. Pharmaceutically acceptable further means a non-toxic material that is compatible with a biological system such as a cell, cell culture, tissue, or organism. The particular carrier may vary depending on the route of therapeutic delivery.

Pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or DNA-binding polymers of the instant invention can also be administered in a local rather than a systemic fashion, such as injection as a sustained release formulation. The following dosage forms are given by way of example and should not be construed as limiting the instant invention.

Compositions suitable for parenteral administration conveniently comprise a sterile aqueous preparation of the agent, which is preferably isotonic with the blood of the recipient. This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found, for example, in "Remington's Pharmaceutical Sciences" Mack Publishing Co., New Jersey (1991), which is incorporated herein by reference.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, lozenges, each containing a predetermined amount of the agent. Other compositions include suspensions in aqueous liquids or non-aqueous liquids such as a syrup, elixir or an emulsion. Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

Compositions may comprise a biocompatible microparticle or implant that is suitable for implantation. Biocompatible and biodegradable polymeric matrix materials may also be added. The polymeric matrix may be used to achieve sustained release of the agent in a subject. DNA-binding polymers of the invention may be encapsulated or dispersed within a biocompatible and biodegradable polymeric matrix. The polymeric matrix can be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Such polymers may be natural or synthetic polymers. Synthetic polymers are preferred. The polymer is selected based on the period of time over which release is desired, generally in the order of a few hours to a year or longer. The polymer optionally is in the form of a hydrogel that can absorb up to about 90% of its weight in water and further, optionally is cross-linked with multi-valent ions or other polymers.

Exemplary synthetic polymers which can be used include: polycarbonates, polyalkylenes, polyalkylene glycols, polyalkylene oxides, polyalkylene terpthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone. Examples of non-biodegradable polymers include ethylene vinyl acetate, poly(meth)acrylic acid, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers may also be included in the present compositions. Examples of such bioadhesive polymers include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

Compositions of the present invention may be formulated as timed release, delayed release, or sustained release delivery systems. Such systems can avoid the need for repeated administrations of the agent of the invention, increasing convenience to the subject and the physician. Many types of release delivery systems are available and known to those of ordinary skill in the art. They include the above-described polymeric systems, as well as polymer base systems such as poly(lactide-glycolide), polyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854, 480, 5,133,974 and 5,407,686. In addition, pump-based hardware delivery systems can be used, some of which are adapted for implantation.

Use of a long-term sustained release implant may be used in the treatment of chronic conditions, such as the suspected presence of dormant metastases. Long-term release, are used herein, means that the implant is constructed and arranged to deliver therapeutic levels of the active ingredient for at least 30 days, at least 60 days and more preferably for several months. Long-term sustained release implants are well-known to those of ordinary skill in the art and include some of the release systems described above.

For oral, buccal, and sublingual administration, powders, suspensions, granules, tablets, pills, capsules, gelcaps, and caplets are acceptable as solid dosage forms. These can be prepared, for example, by mixing one or more DNA-binding polymers of the instant invention, or pharmaceutically acceptable salts or tautomers thereof, with at least one additive or excipient such as a starch or other additive. Suitable additives or excipients are sucrose, lactose, cellulose, sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents, or perfuming agents. Additionally, dyestuffs or pigments may be added for identification. Tablets and pills may be further treated with suitable coating materials known in the art.

As noted above, suspensions may include oils. Such oils include, but are not limited to, peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or DNA-binding polymers of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or diluents include sterilized water, Ringer's solution, or an isotonic aqueous saline solution. For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more DNA-binding polymers of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Compositions of the present invention embrace pharmaceutically acceptable salts of DNA-binding polymers of the invention. Pharmaceutically acceptable salts include a salt with an inorganic base, organic base, inorganic acid, organic acid, or basic or acidic amino acid. As salts of inorganic bases, the invention includes, for example, salts of alkali metals (such as sodium or potassium) and alkaline earth metals (such as calcium and magnesium or aluminum, and ammonia). As salts of organic bases, the invention includes, for example, salts of trimethylamine, triethylamine, pyridine, picoline, ethanolamine, diethanolamine, triethanolamine. As salts of inorganic acids, the instant invention includes, for example, salts of hydrochloric acid, hydroboric acid, nitric acid, sulfuric acid, and phosphoric acid. As salts of organic acids, the instant invention includes, for example, salts of formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

The present invention is further illustrated by the following examples, which are not intended to be limiting in any way whatsoever.

EXAMPLES

Example 1

1.1 Abstract

Androgen receptor (AR) is essential for the growth and progression of prostate cancer in both hormone-sensitive and hormone-refractory disease. A DNA-binding polyamide that targets the consensus androgen response element binds the prostate-specific antigen (PSA) promoter androgen response element, inhibits androgen-induced expression of PSA and several other AR-regulated genes in cultured prostate cancer cells, and reduces AR occupancy at the PSA promoter and enhancer. Down-regulation of PSA by this polyamide was comparable to that produced by the synthetic antiandrogen bicalutamide (Casodex) at the same concentration. Genome-wide expression analysis reveals that a similar number of transcripts are affected by treatment with the polyamide and with bicalutamide. Direct inhibition of the AR-DNA interface by sequence-specific DNA binding small molecules could offer an alternative approach to antagonizing AR activity.

Abbreviations: AR, androgen receptor; ARE, androgen response element; PSA, prostate-specific antigen; DHT, dihydrotestosterone.

1.2 Introduction

The androgen receptor (AR) is a member of the ligand-activated nuclear receptor family of transcription factors (1). Ligand binding to AR initiates release from the cytoplasm, dimerization, binding to the androgen response elements (ARE) of target genes, and gene activation through interaction with coactivators and the general transcription machinery (2). Functional AREs, consensus sequence 5'-GGTA-CAnnnTGTTCT-3' (SEQ ID NO:1) (FIG. 7A) (3) can occur in proximal promoter sequences or in enhancers located up to several thousand base pairs upstream or downstream of the transcription start site.

The regulation of prostate-specific antigen (PSA) (KLK3) expression by AR has been extensively studied as a model for AR-mediated gene activation (4-7). Androgenic induction of PSA is mediated by AR binding to the proximal promoter ≈170 bp from the transcription start site and to several low-affinity AREs in an enhancer ≈4,000 bp upstream (4-6). AREs in both the promoter and enhancer are important for induction after androgen stimulation. AR occupies both the promoter and enhancer regions and recruits transcriptional coactivators including p160 and p300, TATA-binding protein, mediator, and RNA polymerase II to form the AR transcription complex (7, 8). Chromatin-capture assays suggest that the PSA enhancer is located near the promoter in this complex (8).

AR signaling regulates normal prostate development and contributes to the progression of prostate cancer (9). Surgical or drug therapies that act to limit circulating androgen levels or directly antagonize ligand binding to AR initially slow prostate cancer growth (10, 11). However, nearly all patients treated with antiandrogen therapies will eventually develop hormone-refractory disease (12). Dysregulation of AR activity, together with activation of the PTEN/AKT pathway, is thought to contribute to this transition (13). Up-regulation of AR mRNA was found to occur in all transitions from hormone-sensitive to hormone-refractory disease in a mouse tumor-xenograft model of prostate cancer (14). Additionally, a transgenic mouse with a mutated AR that inappropriately interacts with transcriptional coregulators developed metastatic neoplastic disease (15). Mutations in the AR ligand-binding domain can render antagonists such as bicalutamide or flutamide ineffective or, in some models of hormone-refractory disease, convert them to agonists (14, 16). Given that genotropic AR activity is thought to be necessary throughout prostate cancer progression, direct antagonism of AR-DNA binding could inhibit androgen receptor activity in hormone-refractory conditions where androgen antagonists that target the ligand-binding pocket are ineffective (9).

DNA-binding polyamides represent one approach to inhibiting protein-DNA interactions. Polyamides containing N-methylimidazole (Im) and N-methylpyrrole (Py) comprise a class of programmable DNA-binding ligands capable of binding to a broad repertoire of DNA sequences with affinities and specificities comparable to those of natural DNA-binding proteins (17, 18). Sequence specificity is programmed by side-by-side pairings of the heterocyclic amino acids in the minor groove of DNA: Im/Py distinguishes G.C from C.G; Py/Py binds both A.T and T.A (19, 20). Previously, a hairpin polyamide targeted to the hypoxia response element (HRE) inhibited hypoxia-induced expression of several HIF-1-regulated genes, including VEGF, in cultured cells (21, 22).

In this study, we have designed a cell-permeable polyamide to target the sequence 5'-WGWWCW-3', found in the consensus ARE, with the goal of disrupting AR-mediated gene expression (FIG. 7). We show that this polyamide binds the ARE found in the PSA promoter, inhibits expression of PSA as well as ≈35% of the transcripts that were induced by dihydrotestosterone (DHT) in cultured prostate cancer cells, and reduces AR occupancy at the PSA promoter and enhancer. Down-regulation of PSA by this polyamide was comparable to the effects of the synthetic antiandrogen bicalutamide (Casodex) at the same concentration. A control polyamide targeted to a different sequence had less effect.

1.3 Materials and Methods

1.3.1 Synthesis of polyamides

Polyamides 1 (structure 39, FIG. 4) and 2 were synthesized by solid-phase methods on Kaiser oxime resin (Nova Biochem, Darmstadt, Germany) according to established protocols (43). Polyamides were cleaved from resin with 3,3'-diamino-N-methyl-dipropylamine and purified by reverse-phase HPLC. Isophthalic acid was activated with PyBOP (Nova Biochem) and conjugated to the polyamides as described (22). Purities and identities of the polyamides were assessed by HPLC, UV-visible spectroscopy, and MALDI-TOF MS.

1.3.2 Determination of DNA-Binding Affinity and Sequence Specificity

Plasmid pAR-PSA was constructed by inserting a 70-bp sequence from the PSA promoter containing the ARE into pUC19 plasmid. Quantitative DNase I footprint titration experiments were used to measure the binding affinities of 1 and 2 on a 5'-$^{32}$P-labeled fragment of pAR-PSA that contains the PSA promoter ARE. Detailed experimental protocols are reported elsewhere (44).

1.3.3 Electrophoretic Mobility Shift Assay

The oligonucleotide 5'-GCATTGC AGAACAGCAAGTGCTAGCTCTCCC-3' (SEQ ID NO:14) containing the PSA promoter ARE (underlined) was end-labeled with $^{32}$P and annealed to its complement. Polyamides 1 and 2 were incubated with the duplex for 3 h in previously optimized buffer conditions (45). Nuclear extract from DHT-treated LNCaP cells (Genetex, San Antonio, Tex.) was then added for an additional 45 min. Complexes were run on a 5% polyacrylamide gel and visualized on a phosphorimager.

1.3.4 Measurement of Androgen-Induced PSA mRNA and Protein

LNCaP cells (ATCC) were plated in 24-well plates at a density of 40-50×10$^3$ cells per well (80-100×10$^3$ cells per ml) in RPMI medium 1640 (ATCC) supplemented with 10% FBS (Irvine Scientific, Santa Ana, Calif.). After 72 h, the medium was replaced with RPMI medium 1640 containing 10% charcoal stripped FBS with or without polyamides at the designated concentrations. Cells were grown for an additional 48 h and then treated with 1 nM DHT for 16 h. When appropriate, bicalutamide was added 2 h before DHT stimulation. Isolation of RNA and cDNA synthesis was performed as described (21). Quantitative real-time RT-PCR was performed with SYBR Green PCR Master Mix (Applied Biosystems, Foster City, Calif.) on an ABI 7300 instrument. PSA mRNA was measured relative to β-glucuronidase as an endogenous control. Primer sequences are available upon request. Cell-culture supernatants were collected for an ELISA (R & D Systems, Minneapolis, Minn.) to measure PSA protein according to the manufacturer's protocol.

1.3.5 Chromatin Immunoprecipitation

LNCaP cells were plated in 15-cm diameter plates at a density of $2 \times 10^6$ cells per plate. Media, polyamide treatment, time course, and DHT stimulation were the same as described above. After the 16-h DHT treatment, cells were treated with 1% formaldehyde for 10 min. Chromatin was isolated and sheared. Antibodies to AR (AR-20, Santa Cruz Biotechnology, Santa Cruz, Calif.) were used to immunoprecipitate AR-bound DNA fragments. Crosslinks were reversed, and PCRs using primers targeted to the regions of interest were used to assess enrichment of bound fragments as compared with mock-precipitated (no antibody) controls. PCRs were monitored with SYBR Green PCR Master Mix (Applied Biosystems) on an ABI 7300 instrument. Primer sequences and a more detailed experimental protocol are available upon request.

1.3.6 Analysis of Gene Expression with Oligonucleotide Microarrays

LNCaP cells were plated in 12-well plates at a density of $80\text{-}100 \times 10^3$ cells per well. Media, polyamide treatments, and time courses were the same as described above. Bicalutamide was added 2 h before DHT stimulation. RNA was isolated as described in ref. 21. From this point, experiments were carried out at the Millard and Muriel Jacobs Gene Expression Facility at the California Institute of Technology. Labeled mRNA was hybridized to Affymetrix high-density Human Genome U133 Plus 2.0 arrays according to established protocols. Gene expression was analyzed by using Resolver (Rosetta Biosoftware, Seattle, Wash.). Data were uploaded to the Gene Expression Omnibus repository (accession no. GSE7708).

1.4 Results 1.4.1 Binding Affinities of Polyamides to the ARE of the PSA Promoter The proximal PSA promoter contains the ARE 5'-AGAACAGCAAGTGCT-3' (SEQ ID NO:15) (FIG. 8A). The DNA binding of polyamides 1 and 2 on this sequence was measured by quantitative DNase I footprint titrations using a 5'-$^{32}$P-labeled PCR fragment of pAR-PSA, which contains the PSA ARE. Polyamide 1 has a $K_a = 8.3 \pm 1.7 \times 10^9$ $M^{-1}$ for the ARE consensus half-site 5'-AGAACA-3' (FIG. 8B). Binding of polyamide 2, which targets the sequence 5'-WGWCGW-3', to the ARE is not measurable by these methods ($K_a < 1 \times 10^7$) (FIG. 8C). Minimal binding of polyamide 1 is observed at the other half-site of the ARE: 5'-AGTGCT-3', which is formally a single base pair mismatch site for 1. However, 1 is observed to bind the sequence 5'-AGATCA-3' ≈12 bp 5' to the ARE, which is an expected binding site for this molecule.

1.4.2 Electrophoretic Mobility Shift Assay

The effects of polyamides 1 and 2 on the binding of factors present in the nuclear extract isolated from DHT-stimulated LNCaP cells to the ARE site in the PSA promoter was measured by an electrophoretic mobility shift assay (FIG. 8D). Polyamide 1 inhibits binding to the 5'-$^{32}$P-labeled duplex at concentrations as low as 10 nM. Polyamide 2 has minimal effect at the same concentrations.

1.4.3 Inhibition of Androgen-Inducted PSA Expression

Induction of PSA mRNA by DHT in the presence of polyamides 1 and 2 and bicalutamide in LNCaP cells was measured by quantitative real-time RT-PCR. Bicalutamide and polyamide 1 inhibit the expression of DHT-induced PSA in a dose-dependent manner up to ≈70% at 10 μM, as measured in this assay (FIG. 9A). Polyamide 2 has a more modest effect. Secretion of PSA protein after DHT stimulation of LNCaP cells in the presence of 1 and 2 was measured by ELISA (FIG. 9B). Supernatant concentrations of PSA protein are reduced in cells pretreated with 1 as compared with 2 or an untreated control. AR occupancy at the PSA promoter and enhancer was assessed by chromatin immunoprecipitation (FIG. 9C). Chromatin immunoprecipitation assays with anti-AR antibody treatment indicate decreased occupancy of AR at the PSA promoter and enhancer in the presence of 10 μM 1. Polyamide 2 has minimal effect. Polyamides 1 and 2 display no obvious detrimental effects on cell growth over the course of the experiment. AR mRNA is minimally affected by 1 (FIG. 11).

1.4.4 Inhibition of Androgen-Induced FKBP5 Expression

Recent studies have identified FKBP5 as one of the most strongly induced genes in androgen-stimulated prostate cancer cells (23). Two functional AREs with the sequences 5'-AGCACATCGAGTTCA-3' (SEQ ID NO:16) and 5'-AGAACAGGGTGTTCT-3' (SEQ ID NO:17) have been mapped to an enhancer within the fifth intron (24). Polyamide 1 inhibits DHT-induced expression of FKBP5 by ≈60% (FIG. 9D). Bicalutamide was more potent, however, inhibiting expression by almost 95%. Polyamide 2 has minimal effect on FKBP5 expression. Chromatin immunoprecipitation assays indicate decreased occupancy of AR at the FKBP5 intronic enhancer in the presence of 10 μM 1 (FIG. 9E), whereas polyamide 2 has no measurable effect.

1.4.5 Global Effects on Androgen-Induced Gene Expression

Figure 10A:
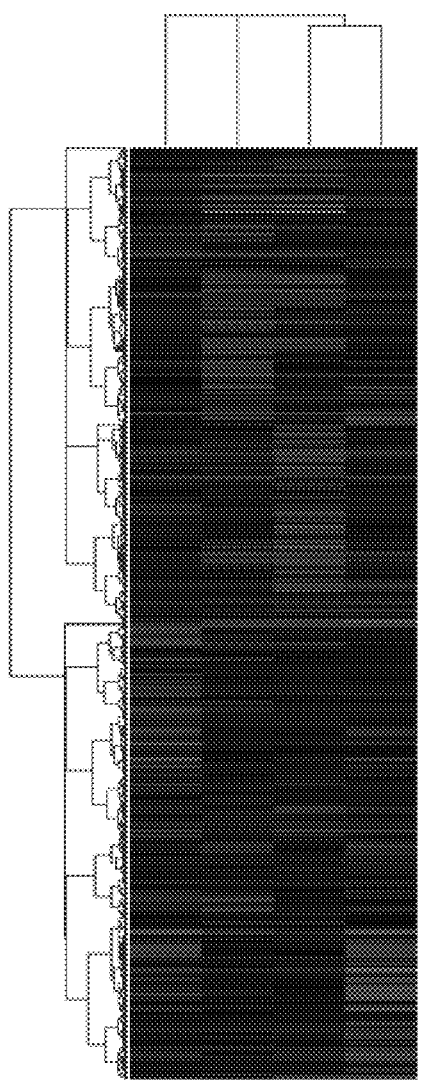

Global effects of polyamides 1 and 2 and bicalutamide on gene expression in DHT-stimulated LNCaP cells were monitored with Affymetrix (Santa Clara, Calif.) high-density Human Genome U133 Plus 2.0 arrays, which interrogate >50,000 transcripts. As compared with DHT-induced controls, polyamide 1 (10 μM) affected the expression of 1,053 transcripts by at least 2-fold (P≤0.01) (Table 1), which represents less than 2% of interrogated transcripts. Of this total, 706 were down-regulated. At the same threshold, bicalutamide (10 μM) affected the expression of 1,213 transcripts, with 602 of these being down-regulated. Polyamide 2 (10 μM) affected the expression of 379 transcripts, which represents <1% of interrogated transcripts. A divisive clustering analysis over all interrogated transcripts suggests that the expression profiles of cells treated with bicalutamide, 1, and 2 are largely distinct (FIG. 10A). Analysis of transcripts affected by both bicalutamide and 1 shows that 122 and 90 transcripts are commonly down- and up-regulated, respectively, at least 2-fold (P≤0.01) (FIG. 10B). Of the 122 transcripts down-regulated by both bicalutamide and 1, 117 are also observed to be induced by DHT at the same thresholds. Of the 90 up-regulated transcripts, 59 are observed to be repressed by DHT.

TABLE 1

Number of transcripts affected relative to DHT-induced controls. (p ≤ 0.01)

| | Treatment | | | |
|---|---|---|---|---|
| | — | B | 1 | 2 |
| | | DHT | | |
| | − | + | + | + |
| up-regulated (fold change ≥2.0) | 486 | 611 | 347 | 95 |
| down-regulated (fold change ≤−2.0) | 782 | 602 | 706 | 284 |

TABLE 1-continued

Number of transcripts affected relative to DHT-induced controls. (p ≤ 0.01)

| | Treatment | | | |
|---|---|---|---|---|
| | — | B | 1 | 2 |
| | DHT | | | |
| | − | + | + | + |
| up-regulatd (fold change ≥4.0) | 88 | 96 | 42 | 11 |
| down-regulated (fold change ≤−4.0) | 199 | 133 | 126 | 32 |

Figure 10C:
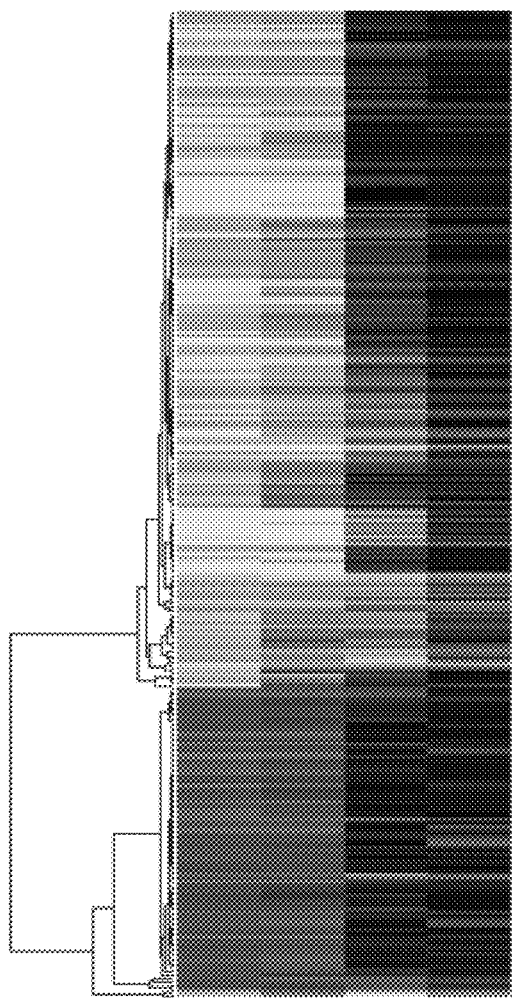

The response of cultured prostate cancer cells to androgen has been extensively studied (23, 25). We find that DHT induced the expression of a set of 199 transcripts by at least 4-fold (P≤0.01). Of this set, 70 were also inhibited by polyamide 1 by at least 2-fold (P≤0.01). For comparison, polyamide 2 inhibited 20, and bicalutamide inhibited 186, of the 199 DHT-induced transcripts with the same thresholds (FIG. 10C). DHT repressed the expression of a set of 88 transcripts by at least 4-fold (P≤0.01). Of this set, eight were also derepressed, as compared with DHT-treated controls, by polyamide 1 by at least 2-fold (P≤0.01). For comparison, polyamide 2 derepressed 3, and bicalutamide derepressed 87, of the 88 transcripts repressed by DHT with the same thresholds (FIG. 10C). A complete list of the DHT-induced transcripts and those affected by 1 is provided in Tables 3 and 4. It is not known what proportions of these genes are direct targets of AR. Table 2 displays the effects of each treatment on the expression of a few selected genes that were observed to be induced by DHT and are known to be targets of AR (26, 27). Effects on the expression of KLK2 and TMPRSS2 were verified by quantitative real-time RT-PCR (FIG. 11).

TABLE 2

Fold-changes of selected AR-target genes relative to DHT-induced controls.

| | Treatment | | | |
|---|---|---|---|---|
| | — | B | 1 | 2 |
| | | DHT | | |
| Gene | − | + | + | + |
| KLK2 | −23.0 | −14.7 | −2.4 | −1.1 |
| KLK3 (PSA) | −6.1 | −3.2 | −3.3 | −1.4 |
| TMPRSS2 | −6.2 | −4.1 | −2.3 | −1.4 |
| FKBP5 | −42.9 | −36.4 | −3.1 | 1.5 |

TABLE 3

Transcripts induced at least 4-fold (p ≤ 0.01) by dihydrotestosterone. Fold change is expressed as DHT non-induced compared to DHT-induced.

| Name | Accession # | Fold Change | P-value |
|---|---|---|---|
| FLJ23153 | AA650281 | −100.0 | 0.000 |
| ORM1 | NM_000607 | −95.9 | 0.000 |
| ORM1 | NM_000607 | −43.4 | 0.000 |
| FKBP5 | NM_004117 | −42.9 | 0.000 |
| FLJ39502 | NM_173648.1 | −35.5 | 0.000 |
| HPGD | AL574184 | −27.2 | 0.000 |
| MAK | NM_005906 | −24.0 | 0.000 |
| KLK2 | AF188747 | −23.0 | 0.000 |
| HPGD | J05594 | −21.3 | 0.000 |
| DKFZp761P0423 | BF739767 | −21.0 | 0.000 |
| MAF | NM_005360 | −19.4 | 0.000 |
| ORM2 | NM_000608 | −18.4 | 0.000 |
| FLJ11937 | NM_022765 | −17.2 | 0.000 |
| FKBP5 | W86302 | −17.2 | 0.000 |
| FLJ11264 | NM_018371 | −15.4 | 0.000 |
| AKAP1 | AB003476 | −15.4 | 0.000 |
| WBSCR5 | AF257135 | −14.7 | 0.000 |
| SLC41A1 | AW439816 | −14.6 | 0.000 |
| SLC15A2 | BF223679 | −13.9 | 0.000 |
| PIK3AP1 | AW575754 | −13.6 | 0.000 |
| FKBP5 | AI753747 | −13.6 | 0.000 |
| SLUG | AI572079 | −13.4 | 0.000 |
| SLC26A3 | NM_000111 | −13.1 | 0.000 |
| KLK2 | BC005196 | −13.0 | 0.000 |
| SLC2A3 | NM_006931 | −13.0 | 0.000 |
| KLK2 | AA595465 | −12.7 | 0.000 |
| BM040 | NM_018456 | −12.7 | 0.000 |
| SGK | NM_005627 | −12.7 | 0.000 |
| 230577_at | AW014022 | −12.4 | 0.000 |
| 242391_at | AW052176 | −11.8 | 0.000 |
| HPGD | NM_000860 | −11.4 | 0.000 |
| CEP3 | AI754416 | −11.3 | 0.000 |
| MAF | AF055376 | −10.9 | 0.000 |
| KIAA0056 | AI796581 | −10.2 | 0.000 |
| SPOCK | AF231124 | −10.1 | 0.000 |
| MYBPC1 | BF593509 | −10.0 | 0.000 |
| EMP1 | NM_001423 | −9.8 | 0.000 |
| TRG@ | M27331 | −9.8 | 0.000 |
| GNMT | AF101477 | −9.6 | 0.000 |
| HSY11339 | Y11339 | −9.5 | 0.000 |
| MAF | BE674528 | −9.4 | 0.000 |
| KIAA1145 | BG177562 | −9.4 | 0.000 |
| 244650_at | AA581439 | −9.2 | 0.000 |
| TRG@ | M16768 | −9.1 | 0.000 |
| F5 | NM_000130 | −9.1 | 0.000 |
| HPGD | U63296 | −9.0 | 0.000 |
| TRGC2 | M13231 | −8.9 | 0.000 |
| IGF1R | H05812 | −8.8 | 0.001 |
| NAT3 | NM_018018 | −8.6 | 0.000 |
| PNLIP | NM_000936 | −8.5 | 0.000 |
| PLEC1 | NM_000445 | −8.5 | 0.003 |
| KIAA0869 | AK001727 | −8.5 | 0.000 |
| MGC18216 | AL044092 | −8.4 | 0.000 |
| LIFR | AW592684 | −8.3 | 0.000 |
| NDRG1 | NM_006096 | −8.2 | 0.000 |
| FAM105A | AF052146 | −8.0 | 0.000 |
| LIFR | NM_002310 | −7.8 | 0.000 |
| ERN1 | AW194689 | −7.6 | 0.000 |
| FLJ11127 | NM_019018 | −7.5 | 0.000 |
| MOGAT2 | AK000245 | −7.4 | 0.000 |
| CEP3 | AI801777 | −7.2 | 0.000 |
| TMCC3 | N51717 | −7.1 | 0.000 |
| DKFZP434B0335 | BF513674 | −7.1 | 0.000 |
| LIFR | AI680541 | −7.0 | 0.000 |
| LAMA1 | AI990816 | −6.9 | 0.000 |
| 228559_at | BF111626 | −6.9 | 0.000 |
| BCAP29 | N57499 | −6.9 | 0.000 |
| NNT | U40490 | −6.9 | 0.000 |
| PTPRN2 | NM_002847 | −6.8 | 0.000 |
| CTNNA2 | NM_004389 | −6.8 | 0.000 |
| LRRFIP2 | AW137053 | −6.8 | 0.000 |
| FLJ11278 | NM_018378 | −6.7 | 0.000 |
| AFF3 | AW085505 | −6.7 | 0.000 |
| MGC13102 | BC005094 | −6.7 | 0.000 |
| PDEF | AI435670 | −6.6 | 0.000 |
| TRG@ | M30894 | −6.6 | 0.000 |
| CECR6 | AF307451 | −6.6 | 0.000 |
| TMEPAI | AL035541 | −6.6 | 0.000 |
| FLJ10055 | NM_017983 | −6.5 | 0.000 |
| LOC401623 | AI743452 | −6.5 | 0.000 |
| SLC2A3 | AI631159 | −6.5 | 0.001 |
| 235445_at | BF965166 | −6.4 | 0.000 |
| KIAA1330 | AB037751 | −6.4 | 0.001 |
| PCDH1 | NM_002587 | −6.4 | 0.000 |

TABLE 3-continued

Transcripts induced at least 4-fold (p ≤ 0.01) by dihydrotestosterone. Fold change is expressed as DHT non-induced compared to DHT-induced.

| Name | Accession # | Fold Change | P-value |
|---|---|---|---|
| STAT12 | NM_003877 | −6.3 | 0.000 |
| TMPRSS2 | AI660243 | −6.2 | 0.000 |
| FER1L3 | NM_013451 | −6.2 | 0.000 |
| PRKCA | AI471375 | −6.1 | 0.000 |
| KLK3 | U17040 | −6.1 | 0.000 |
| SMPD2 | NM_003080 | −6.1 | 0.009 |
| MPHOSPH9 | X98258 | −6.0 | 0.000 |
| TBX15 | AI039005 | −6.0 | 0.000 |
| IGF1R | AI830698 | −5.9 | 0.000 |
| ELL2 | NM_012081 | −5.9 | 0.000 |
| TRPM8 | AI272941 | −5.9 | 0.000 |
| DSC1 | NM_004948 | −5.9 | 0.000 |
| CRIP2 | U36190 | −5.8 | 0.000 |
| TMEPAI | NM_020182 | −5.8 | 0.000 |
| FLJ23563 | AW138767 | −5.8 | 0.000 |
| KIAA1001 | AW052084 | −5.7 | 0.000 |
| BM039 | AK023669 | −5.7 | 0.000 |
| STAT12 | AB004903 | −5.7 | 0.000 |
| TMEPAI | AL035541 | −5.6 | 0.000 |
| KLK3 | NM_001648 | −5.6 | 0.000 |
| POV1 | NM_003627 | −5.5 | 0.000 |
| CNKSR2 | AI670947 | −5.5 | 0.000 |
| STK17B | N51102 | −5.5 | 0.000 |
| 232397_at | R14890 | −5.5 | 0.000 |
| ATRNL1 | BC035157.1 | −5.5 | 0.001 |
| HAK | AI741514 | −5.4 | 0.003 |
| ANKH | NM_019847 | −5.4 | 0.000 |
| LOC144481 | AK054607 | −5.4 | 0.000 |
| FER1L3 | AF207990 | −5.3 | 0.000 |
| ANK1 | NM_020479 | −5.3 | 0.001 |
| FLJ23153 | NM_024636 | −5.2 | 0.000 |
| PER1 | NM_002616 | −5.2 | 0.000 |
| 230782_at | AV699883 | −5.2 | 0.000 |
| ALAS2 | Z83821 | −5.1 | 0.000 |
| FLJ20624 | NM_017906 | −5.1 | 0.000 |
| TMPRSS2 | AF270487 | −5.1 | 0.000 |
| RAB3B | BC005035 | −5.0 | 0.000 |
| dJ646B12.1, dJ646B12.2 | AL096776 | −5.0 | 0.000 |
| 238975_at | AI671390 | −5.0 | 0.006 |
| PPFIBP2 | AI692180 | −4.9 | 0.000 |
| MAP3K10 | NM_002446 | −4.9 | 0.002 |
| LIFR | AA701657 | −4.9 | 0.000 |
| PHLDB2 | AK025444 | −4.9 | 0.000 |
| KRT19 | NM_002276 | −4.9 | 0.000 |
| MAF | BF508646 | −4.9 | 0.001 |
| C1orf21 | NM_030806 | −4.8 | 0.000 |
| KRT8 | AL024458 | −4.8 | 0.000 |
| MGC4827 | NM_024114 | −4.8 | 0.000 |
| PTGER4 | AA897516 | −4.8 | 0.000 |
| 230710_at | W05495 | −4.7 | 0.000 |
| 1556185_a_at | BC035072.1 | −4.7 | 0.000 |
| DKFZP434B044 | AL136861 | −4.7 | 0.000 |
| TBC1D1 | BC028196.1 | −4.7 | 0.000 |
| ALDH4A1 | NM_003748 | −4.7 | 0.000 |
| DGCR14 | AL137713 | −4.7 | 0.003 |
| CSRP2 | NM_001321 | −4.7 | 0.000 |
| KIAA0194 | D83778 | −4.6 | 0.000 |
| FLJ11200 | AA886870 | −4.6 | 0.000 |
| GG2-1 | BC005352 | −4.6 | 0.000 |
| GG2-1 | NM_014350 | −4.6 | 0.000 |
| TMPRSS2 | NM_005656 | −4.6 | 0.000 |
| ABCC1 | NM_004996 | −4.5 | 0.000 |
| C1orf21 | AI159874 | −4.5 | 0.000 |
| ABCC4 | NM_005845 | −4.5 | 0.000 |
| IGF1 | AI972496 | −4.5 | 0.000 |
| BMPR1B | D89675 | −4.5 | 0.004 |
| ADH1C | NM_000669 | −4.5 | 0.004 |
| SLC16A6, LOC440459 | AI873273 | −4.5 | 0.000 |
| RAB3B | AU156710 | −4.5 | 0.000 |
| PIG11 | NM_006034 | −4.5 | 0.002 |
| KIAA0575 | NM_014668 | −4.5 | 0.000 |
| 241950_at | BG034847 | −4.4 | 0.007 |
| LOC221981 | R33964 | −4.4 | 0.001 |
| KCNMA1 | AI129381 | −4.4 | 0.000 |
| CAMKK2 | AA181179 | −4.4 | 0.000 |
| SEC14L2 | NM_012429 | −4.4 | 0.000 |
| FZD5 | NM_003468 | −4.4 | 0.010 |
| OACT2 | AI761250 | −4.4 | 0.000 |
| LIG1 | AB050468 | −4.4 | 0.000 |
| F5 | AA910306 | −4.4 | 0.004 |
| LOC90268 | AA723152 | −4.4 | 0.000 |
| bK215D11.1, bK215D11.2, bK215D11.3 | AL034417 | −4.4 | 0.000 |
| ABCC4 | AI248055 | −4.4 | 0.000 |
| FACL3 | D89053 | −4.4 | 0.000 |
| KIAA1921 | BE465475 | −4.3 | 0.000 |
| PDEF | NM_012391 | −4.3 | 0.000 |
| ELL2 | AI745624 | −4.3 | 0.000 |
| WRCH-1 | AB051826 | −4.2 | 0.000 |
| C1orf21 | AL563236 | −4.2 | 0.000 |
| RFXDC1 | NM_173560.1 | −4.2 | 0.000 |
| KCNMA1 | U11058 | −4.2 | 0.000 |
| KLF5 | AF132818 | −4.2 | 0.000 |
| ZNF145 | NM_006006 | −4.2 | 0.000 |
| ELL2 | AI924426 | −4.2 | 0.000 |
| CXCR4 | AJ224869 | −4.2 | 0.000 |
| MGC13102 | AW090182 | −4.2 | 0.000 |
| LIN-7B | NM_022165 | −4.1 | 0.000 |
| DKFZP434E2135 | NM_030804 | −4.1 | 0.000 |
| ACY1L2 | AI654133 | −4.1 | 0.001 |
| PGC | NM_002630 | −4.1 | 0.000 |
| HOMER-2B | Y19026 | −4.1 | 0.000 |
| SLC2A3 | BE550486 | −4.1 | 0.000 |
| UCHL1 | NM_004181 | −4.1 | 0.001 |
| OACT2 | W63676 | −4.1 | 0.000 |
| FACL3 | NM_004457 | −4.1 | 0.000 |
| MAF | AA442149 | −4.1 | 0.006 |
| SEC14L2 | R49343 | −4.1 | 0.002 |
| 229814_at | BG149337 | −4.0 | 0.000 |
| ABHD2 | AI832249 | −4.0 | 0.002 |
| FAM13C1 | BC036453.1 | −4.0 | 0.000 |
| TBC1D1 | BE882538 | −4.0 | 0.000 |
| NAT3 | AF193836 | −4.0 | 0.000 |
| FLJ10350 | NM_018067 | −4.0 | 0.000 |
| CEP2 | W81196 | −4.0 | 0.003 |
| AZGP1 | D90427 | −4.0 | 0.000 |

TABLE 4

Transcripts inhibited at least 2-fold (p ≤ 0.01) by polyamide 1 that are also induced at least 4-fold (p ≤ 0.01) by dihydrotestosterone.

| Name | Accession # | Fold Change | P-value |
|---|---|---|---|
| ANKH | NM_019847 | −7.3 | 0.000 |
| FLJ11264 | NM_018371 | −6.6 | 0.000 |
| KCNMA1 | U11058 | −6.3 | 0.000 |
| FER1L3 | NM_013451 | −6.2 | 0.000 |
| AKAP12 | AB003476 | −5.7 | 0.000 |
| ORM2 | NM_000608 | −5.6 | 0.000 |
| TMCC3 | N51717 | −5.4 | 0.000 |
| FER1L3 | AF207990 | −5.2 | 0.000 |
| KCNMA1 | AI129381 | −5.1 | 0.000 |
| PRKCA | AI471375 | −5.1 | 0.000 |
| LOC144481 | AK054607 | −5.1 | 0.000 |
| PTPRN2 | NM_002847 | −4.8 | 0.000 |
| AFF3 | AW085505 | −4.8 | 0.000 |
| ORM1 | NM_000607 | −4.5 | 0.000 |
| SPOCK | AF231124 | −4.4 | 0.000 |
| BMPR1B | D89675 | −4.3 | 0.001 |
| TRG@ | M16768 | −4.2 | 0.000 |
| C1orf21 | NM_030806 | −4.2 | 0.000 |
| TRGC2 | M13231 | −4.1 | 0.000 |
| LOC221981 | R33964 | −3.9 | 0.000 |

TABLE 4-continued

Transcripts inhibited at least 2-fold (p ≤ 0.01) by polyamide 1 that are also induced at least 4-fold (p ≤ 0.01) by dihydrotestosterone.

| Name | Accession # | Fold Change | P-value |
|---|---|---|---|
| TRG@ | M27331 | −3.8 | 0.000 |
| RFXDC1 | NM_173560.1 | −3.8 | 0.000 |
| CRIP2 | U36190 | −3.8 | 0.000 |
| ORM1 | NM_000607 | −3.7 | 0.000 |
| ANK1 | NM_020479 | −3.5 | 0.010 |
| C1orf21 | AI159874 | −3.5 | 0.000 |
| KLK3 | NM_001648 | −3.5 | 0.000 |
| KLK3 | U17040 | −3.3 | 0.000 |
| MGC18216 | AL044092 | −3.3 | 0.000 |
| FLJ23153 | AA650281 | −3.3 | 0.000 |
| 230710_at | W05495 | −3.1 | 0.000 |

TABLE 4-continued

Transcripts inhibited at least 2-fold (p ≤ 0.01) by polyamide 1 that are also induced at least 4-fold (p ≤ 0.01) by dihydrotestosterone.

| Name | Accession # | Fold Change | P-value |
|---|---|---|---|
| SLC15A2 | BF223679 | −2.3 | 0.000 |
| MPHOSPH9 | X98258 | −2.2 | 0.000 |
| KLK2 | AA595465 | −2.2 | 0.000 |
| LIFR | AI680541 | −2.2 | 0.000 |
| TMPRSS2 | NM_005656 | −2.2 | 0.000 |
| TBX15 | AI039005 | −2.1 | 0.000 |
| DKFZP434B0335 | BF513674 | −2.1 | 0.000 |
| SLC41A1 | AW439816 | −2.1 | 0.000 |
| FAM105A | AF052146 | −2.1 | 0.001 |
| AZGP1 | D90427 | −2.1 | 0.000 |
| MAF | NM_005360 | −2.1 | 0.000 |
| STK17B | N51102 | −2.0 | 0.000 |

TABLE 5

IC50 values for inhibition of PSA mRNA expression

| Compound | | LNCaP +DHT | LNAR +DHT | LNAR −DHT |
|---|---|---|---|---|
| 3 | Match | 500 ± 100 nM | 300 ± 30 nM | 120 ± 30 nM |
| 4 | Mismatch | >10 μM | >10 μM | >10 μM |
| | Bic | 900 nM | >1 mM | (3.5 μM) |

TABLE 4-continued

Transcripts inhibited at least 2-fold (p ≤ 0.01) by polyamide 1 that are also induced at least 4-fold (p ≤ 0.01) by dihydrotestosterone.

| Name | Accession # | Fold Change | P-value |
|---|---|---|---|
| TRG@ | M30894 | −3.1 | 0.000 |
| C1orf21 | AL563236 | −3.1 | 0.000 |
| KIAA0869 | AK001727 | −3.1 | 0.000 |
| ABCC4 | AI248055 | −3.0 | 0.000 |
| DKFZP434B044 | AL136861 | −2.9 | 0.000 |
| KIAA1145 | BG177562 | −2.9 | 0.000 |
| 242391_at | AW052176 | −2.8 | 0.000 |
| STATI2 | NM_003877 | −2.8 | 0.000 |
| ELL2 | AI745624 | −2.7 | 0.000 |
| FAM13C1 | BC036453.1 | −2.7 | 0.000 |
| KIAA1921 | BE465475 | −2.7 | 0.000 |
| NDRG1 | NM_006096 | −2.7 | 0.000 |
| SLC26A3 | NM_000111 | −2.6 | 0.000 |
| TRPM8 | AI272941 | −2.6 | 0.000 |
| STATI2 | AB004903 | −2.5 | 0.000 |
| MAK | NM_005906 | −2.5 | 0.000 |
| MGC4827 | NM_024114 | −2.5 | 0.000 |
| PHLDB2 | AK025444 | −2.5 | 0.000 |
| 1556185_a_at | BC035072.1 | −2.4 | 0.000 |
| KLK2 | AF188747 | −2.4 | 0.000 |
| RAB3B | AU156710 | −2.4 | 0.000 |
| CNKSR2 | AI670947 | −2.4 | 0.002 |
| TMPRSS2 | AI660243 | −2.3 | 0.000 |
| 230782_at | AV699883 | −2.3 | 0.000 |
| TMPRSS2 | AF270487 | −2.3 | 0.000 |
| KLK2 | BC005196 | −2.3 | 0.000 |
| LIN-7B | NM_022165 | −2.3 | 0.000 |

Polyamide 1 was tested for its ability to inhibit AR binding and expression of AR regulated genes in a cell line model of hormone refractory prostate cancer. The cell line LNAR was used, which has been engineered to over-express AR (14). LNAR cells over-express AR and form hormone refractory tumors when xenografted in mice (14). AR regulated genes in LNAR-CS cells are not inhibited by antiandrogens such as bicalutamide (14). Upregulation of androgen receptor defeats many synthetic anti-androgens targeted to the ligand-binding pocket. Polyamide 1 disrupts the AR/ARE interface and maintains efficacy in hormone refractory cells such as LNAR. Inhibition of DHT-induced PSA in LNAR cells by 1 and 2 and basal PSA expression (no DHT) by 1 and 2 is shown (FIGS. 12 B and C). Bicalutamide induces expression of PSA in LNAR-CS cells (FIG. 12 C).

Polyamide 3, an analog of polyamide 1 that differs only at the "turn," also inhibits PSA mRNA expression in DHT-induced LNCaP and LNAR cells, as well as basal expression of PSA mRNA in LNAR cells. Polyamide 4 is a corresponding analog of polyamide 2 and has little effect on PSA expression under these conditions. The structures of 3 and 4 are depicted in FIG. 13 A. Representative isotherms are shown depicting the effects of polyamide 3 that targets the ARE (square), and control polyamide 4 (circle), and bicalutamide (triangle) on PSA mRNA expression in LNCaP cells (FIG. 13 B) and LNAR cells (FIG. 13 C). Bicalutamide does not inhibit PSA mRNA expression in LNAR cells (FIG. 13 C). Basal PSA mRNA expression (no DHT) is inhibited by polyamide 3 and inducted by bicalutamide (FIG. 13 D).

Table 5 shows the IC50 values for inhibition of PSA mRNA expression by polyamides 3 and 4 and bicalutamide (Bicalutamide induces PSA mRNA in LNAR cells). The effects on secreted PSA protein mirror the effects on mRNA; polyamide 3 inhibits secretion of PSA in hormone refractory LNAR prostate cancer cells. Polyamide 4 (control) has minimal effect. Bicalutamide fails to inhibit PSA secretion, and further induces PSA expression upon DHT-stimulation (FIG. 14).

1.5 Discussion

Because numerous signaling pathways converge on a smaller number of transcription factors to exert their effects on gene expression, it has been proposed that transcription factors could be among the most appropriate drug targets in oncology (28, 29). This possibility has underscored the challenge to design small molecules capable of selectively disrupting protein-protein interactions between coactivators as well as protein-DNA interactions between transcription factors and their target sites in gene regulatory sequences.

Prostate cancer cells depend on stimulation by circulating androgens that exert their effects through the AR signaling axis. Hormone therapies that block AR activity by starving it of androgens or inhibiting ligand binding are initially successful but ultimately fail to control disease (12). This failure can occur through up-regulation of AR, mutations in the ligand-binding pocket, and ligand-independent activation from upstream signaling proteins (13, 30, 31). It is thought, however, that intact activity of AR signaling is necessary for disease progression (9). Inhibition of the AR-DNA interaction by a sequence-specific DNA-binding molecule could be expected to interfere with AR signaling under both hormone-sensitive and hormone-refractory conditions.

Polyamide 1 binds to a half-site of the ARE of the PSA promoter with a subnanomolar $K_d$ and inhibits expression of ≈35% of transcripts that are observed to be induced at least 4-fold by DHT in LNCaP cells. Down-regulation of PSA by this polyamide is comparable to that produced by the synthetic antiandrogen bicalutamide at the same concentration. Control polyamide 2, which targets a different DNA sequence, 5'-WGWCGW-3', had significantly less effect on androgen-induced gene expression. Expression of PSA (KLK3), KLK2, TMPRSS2, and FKBP5, which are direct AR targets, were all affected by 1. TMPRSS2 encodes a transmembrane protease and can undergo a chromosomal deletion in which a member of the ETS transcription factor family is placed under control of the strongly androgen-responsive TMPRSS2 5' regulatory region (27, 32).

At the same concentration, polyamide 1 and bicalutamide affected a comparable number of transcripts, whereas polyamide 2 affected significantly fewer. When using bicalutamide as a point of reference, the overall effects on genomic transcription by 1 and 2 are relatively modest. Although it is difficult to compare across experimental conditions, the observation that a limited number of genes are affected by each polyamide in this study is consistent with previous reports (21). A comparison of the expression data for cells treated with polyamide 1 or 2 reveal that some transcripts are similarly affected, but many are differentially affected by the two polyamides (FIG. 10A), which is consistent with previous comparisons of gene expression profiles of cells treated with polyamides of different target sequence (21, 33).

Polyamide 1, as well as related polyamide 3 which targets the same DNA sequence, retains its antagonism of AR in the hormone-refractory model cell line LNAR that over-expresses AR. In this cell line bicalutamide loses all activity as an antagonist and displays weak agonist activity.

The AR, glucocorticoid receptor, and estrogen receptor share a highly conserved DNA-binding domain (34-36). This domain, related to the classical Cys-2-His-2 zinc finger motifs (37), contains two modules of zinc coordinated by four cysteines. Previously, a polyamide targeted to the estrogen receptor response element inhibited binding of estrogen receptors α and β in gel-shift assays (38). In separate in vitro experiments, minor groove-binding polyamides have been shown to inhibit the major groove binding of Zif268 and other zinc finger proteins to their target sites on DNA by an allosteric mechanism (39). In light of this observation, it is not unexpected that a polyamide targeted to the ARE would inhibit AR binding.

The ARE is sufficiently degenerate such that a single polyamide is not likely to affect all AR-regulated genes simultaneously. The identities of the particular AR target genes involved in prostate cancer progression are not fully known. In the absence of this knowledge, it was our goal to target the ARE broadly to maximize the number of AR target genes affected by using a single polyamide. However, the programmability of polyamides might allow selective inhibition of a predetermined subset of AR target genes by one or a small mixture of tailored polyamide molecules. The utility of disrupting the AR-ARE interface with DNA-binding small molecules will depend on continued experimentation in small animal models of hormone refractory prostate cancer and AR-regulated gene expression (40-42).

Example 2

2.1 Abstract

Glucocorticoid receptor (GR) regulates expression of genes involved in many biological processes including inflammation. A DNA-binding polyamide that targets the consensus glucocorticoid response element binds the glucocorticoid-induced leucine zipper glucocorticoid response element (GRE), inhibits dexamethasone-induced expression of GILZ in cultured lung cancer cells, and reduces GR occupancy at the GILZ enhancer. Direct inhibition of the GR-DNA interface by sequence-specific DNA binding small molecules could offer an alternative approach to modulating GR activity.

Abbreviations: GR, glucocorticoid receptor; GRE, glucocorticoid response element; GILZ, glucocorticoid induced leucine zipper.

2.2 Introduction

Because polyamide 1, which is expected to bind to most AREs, inhibited the expression of DHT-induced AR regulated genes in LNCaP cells, it was hypothesized that the polyamide 1 might also inhibit the expression of dexamethasone-induced GR regulated genes, since the sequence preferences of AR and GR are very similar as are the amino acid sequences of their respective DNA binding domains. The glucocorticoid receptor (GR) is also a member of the ligand-activated nuclear receptor family of transcription factors (46, 47). Like AR, ligand binding to GR initiates release from the cytoplasm, dimerization, binding to the glucocorticoid response elements (GRE) of target genes, and gene activation through interaction with co-activators and the general transcription machinery. The GREs, consensus 5'-GGTACAnnnTGTTCT-3' (SEQ ID NO:1), can occur near transcription start sites or in enhancers that are several thousand base pairs up or down stream. GR interacts with co-activator proteins to up- or down-regulate specific target genes in a cell-type specific manner (46, 47). Target genes are involved in a large array of biological processes including the immune response. In addition to direct effects on gene transcription through interaction with GREs, GR mediates non-genotropic effects through interaction with cytoplasmic signaling proteins.

DNA-binding polyamides represent one approach to inhibiting protein-DNA interactions. Polyamides containing N-methylimidazole (Im) and N-methylpyrrole (Py) comprise a class of programmable DNA-binding ligands capable of binding to a broad repertoire of DNA sequences with affinities and specificities comparable to those of natural DNA-binding proteins (17, 18). Sequence specificity is programmed by side-by-side pairings of the heterocyclic amino acids in the minor groove of DNA: Im/Py distinguishes G.C from C.G; Py/Py binds both A.T and T.A (19, 20). Previously, a hairpin polyamide targeted to the hypoxia response element (HRE) inhibited hypoxia-induced expression of several HIF-1-regulated genes, including VEGF, in cultured cells (21, 22).

A polyamide that targets the sequence 5'-WGWWCW-3', might be expected antagonize GR-mediated gene expression through interaction with GREs at the regulatory sequences of GR-target genes (FIG. 15 A). We show that such a polyamide binds two GREs found in the GILZ enhancer, inhibits expression of GILZ, and reduces GR occupancy at the GILZ enhancer. A control polyamide targeted to a different sequence had less effect. The modulation of GR activity at the level of DNA binding could have implications for selectively antagonizing genotropic GR activity while leaving non-genotropic activity unaffected. This separation of activity of GR might have useful applications in modulating the effects from glucocorticoid treatment, and is likely not possible using drugs or other molecules currently available.

2.2 Materials and Methods 2.2.1 Synthesis of polyamides

Polyamides 1 and 2 were synthesized by solid-phase methods on Kaiser oxime resin (Nova Biochem, Darmstadt, Germany) according to established protocols (43).

2.2.2 Determination of DNA-Binding Affinity and Sequence Specificity

Quantitative DNase I footprint titration experiments were used to measure the binding affinities of 1 and 2 on a 5'-$^{32}$P-labeled fragment of plasmid pKAM5 that contains the GILZ enhancer GREs. Detailed experimental protocols are reported elsewhere (44).

2.2.3 Electrophoretic Mobility Shift Assay

Polyamides 1 and 2 were incubated with a 5'-$^{32}$P labeled duplex containing the GILZ GREs, and GR protein was added. Complexes were run on a polyacrylamide gel and visualized on a phosphorimager.

2.2.4 Measurement of Androgen-Induced PSA mRNA and Protein

A549 cells (ATCC) were plated in 24-well plates. After 48 h, the medium was replaced and polyamides added at the designated concentrations. Cells were grown for an additional 48 h and then treated with 100 nM dexamethasone. Isolation of RNA and cDNA synthesis was performed as described (21). Quantitative real-time RT-PCR was performed with SYBR Green PCR Master Mix (Applied Biosystems, Foster City, Calif.) on an ABI 7300 instrument. PSA mRNA was measured relative to β-glucuronidase as an endogenous control. Primer sequences are available upon request\

2.3.5 Chromatin Immunoprecipitation

A549 cells were plated in 15-cm diameter plates. Media, polyamide treatment, time course, and DHT stimulation were the same as described above. After dexamethasone treatment, cells were treated with 1% formaldehyde for 10 min. Chromatin was isolated and sheared. Antibodies to GR (graciously gifted by Keith Yamamoto) were used to immunoprecipitate GR-bound DNA fragments. Crosslinks were reversed, and PCRs using primers targeted to the regions of interest were used to assess enrichment of bound fragments as compared with mock-precipitated (no antibody) controls. PCRs were monitored with SYBR Green PCR Master Mix (Applied Biosystems) on an ABI 7300 instrument. Primer sequences and a more detailed experimental protocol are available upon request.

2.4 Results 2.4.1 Binding Affinities of Polyamides to the GREs of the GILZ Enhancer The GILZ enhancer contains two GREs separated by 22 base pairs (46). GRE 1 is 5'-GCCTGCACTTTGTTCT=3' (SEQ ID NO:5) and GRE 2 is GCAAACACCGTGTTCA-3' (SEQ ID NO:7). The DNA binding of polyamides 1 and 2 on these sequences was measured by quantitative DNase I footprint. Polyamide 1 has a $K_a=1.9\pm0.8\times10^{10}$ for GRE1 and $K_a=8.8\pm1.8\times10^9$ for GRE2 (FIG. 16 A-C).

2.4.3 Inhibition of Dexamethasone-Induced GILZ Expression

Induction of GILZ mRNA by dexamethasone in the presence of polyamides 1 and 2 in A549 cells was measured by quantitative real-time RT-PCR. Polyamide 1 inhibits the expression of DHT-induced PSA in a dose-dependent manner up to ≈60% at 10 μM, as measured in this assay (FIG. 17A). Polyamide 2 has a more modest effect. GR occupancy at the GILZ enhancer was assessed by chromatin immunoprecipitation (FIG. 17B). Chromatin immunoprecipitation assays with anti-GR antibody treatment indicate decreased occupancy of GR at the GILZ enhancer in the presence of 10 μM 1.

Example 3

3.1 Overview

It is possible to inhibit the protein-DNA interactions AR-ARE and GR-GRE using polyamides targeted to sequences found in the consensus ARE and GRE. A cell permeable polyamide targeted to these sequences that can access chromatin in cells, bind target sequences, and prevent or displace the binding of the AR or GR, was able to affect the expression of genes regulated by AR or GR.

Because the DNA binding domains of androgen receptor, glucocorticoid receptor, and estrogen receptor are similar in structure, it is here hypothesized that a polyamide targeted to bind at estrogen response elements, EREs, could be expected to antagonize estrogen receptor (ER) activity in cells. Two forms of ER, ER-alpha and ER-beta, exist. These receptors are also members of the ligand-activated nuclear receptor family of transcription factors (48). Like AR and GR, ligand binding to ER initiates release from the cytoplasm, dimerization, binding to the estrogen response elements (ERE) of target genes, and gene activation through interaction with co-activators and the general transcription machinery. The EREs, consensus 5'-AGGTCAnnnT-GACCT-3' (SEQ ID NO:11), can occur near transcription start sites or in enhancers that are several thousand base pairs up or down stream. ER interacts with co-activator proteins to up- or down-regulate specific target genes.

Significantly, ER plays an important role in the growth of breast cancer. Close to two-thirds of breast cancers express either or both of the ER subtypes. Such cancers can be treated hormonally with selective estrogen receptor modulators, such as tamoxifen, or aromatase inhibitors, such as letrozole. However, breast cancers that are initially sensitive to these treatments can become resistant to these treatments over time. This resistance is thought to involve cellular adaptations to low levels of estrogen in which other signaling pathways, that activate the estrogen receptors at extremely low levels of ligand or even in its absence (49, 50). Inhibiting the ER-ERE interaction with a DNA binding molecules could be expected to retain activity under cellular conditions in which tamoxifen or aromatase inhibitors are inactive. Therefore, cell permeable molecules that can bind to EREs and inhibit the binding of or displace ER, for example a DNA binding polyamide targeted to bind the sequence 5'-WGGWCW-3', could be useful for the treatment of breast cancer. Because estrogen receptors play a role in regulating fertility, such molecules could also be useful for treatment of conditions characterized by infertility. Some breast cancers express progesterone receptor (PR), which is also a member of the steroid hormone receptor family of transcription factors.

FIG. 18 depicts an approach to inhibiting the ER-ERE protein-DNA interaction using DNA-binding Py-Im-polyamides. A polyamide targeted to bind the sequence 5'-WGGWCW-3' is expected to bind many possible EREs and inhibit the binding of ER to these sequences in cells, antagonizing the activity of ER at genes regulated by these EREs.

References for Examples 1-3

1. Tsai, M J & Omalley, B W. (1994) *Annu Rev Biochem* 63, 451-486.
2. Tyagi, R K, Lavrovsky, Y, Ahn, S C, Song, C S, Chatterjee, B & Roy, A K. (2000) *Mol Endocrinol* 14, 1162-1174.
3. Roche, P J, Hoare, S A & Parker, M G. (1992) *Mol Endocrinol* 6, 2229-2235.
4. Cleutjens, K B, van der Korput, H A, van Eekelen, C C, van Rooij, H C, Faber, P W & Trapman, J. (1997) *Mol Endocrinol* 11, 148-161.
5. Cleutjens, K B, van Eekelen, C C, van der Korput, H A, Brinkmann, A O & Trapman, J. (1996) *J Biol Chem* 271, 6379-6388.
6. Huang, W B, Shostak, Y, Tarr, P, Sawyers, C & Carey, M. (1999) *J Biol Chem* 274, 25756-25768.
7. Shang, Y F, Myers, M & Brown, M. (2002) *Mol Cell* 9, 601-610.
8. Wang, Q B, Carroll, J S & Brown, M. (2005) *Mol Cell* 19, 631-642.
9. Scher, H I & Sawyers, C L. (2005) *J Clin Oncol* 23, 8253-8261.
10. Huggins, C & Hodges, C V. (1941) *Cancer Res* 1, 293-297.
11. Huggins, C, Stevens, R E & Hodges, C V. (1941) *Arch Surg* (Chicago) 43, 209-223.
12. Oefelein, M G, Agarwal, P K & Resnick, M I. (2004) *J Urol* 171, 1525-1528.
13. Xin, L, Teitell, M A, Lawson, D A, Kwon, A, Mellinghoff, I K & Witte, O N. (2006) *Proc Natl Acad Sci USA* 103, 7789-7794.
14. Chen, C D, Welsbie, D S, Tran, C, Baek, S H, Chen, R, Vessella, R, Rosenfeld, M G & Sawyers, C L. (2004) *Nat Med* 10, 33-39.
15. Han, G Z, Buchanan, G, Ittmann, M, Harris, J M, Yu, X Q, DeMayo, F J, Tilley, W & Greenberg, N M. (2005) *Proc Natl Acad Sci USA* 102, 1151-1156.
16. Bohl, C E, Gao, W Q, Miller, D D, Bell, C E & Dalton, J T. (2005) *Proc Natl Acad Sci USA* 102, 6201-6206.
17. Hsu, C F, Phillips, J W, Trauger, J W, Farkas, M E, Belitsky, J M, Heckel, A, Olenyuk, B Z, Puckett, J W, Wang, C C C & Dervan, P B. (2007) *Tetrahedron* 10.1016/j.tet. 2007.03.041.
18. Dervan, P B & Edelson, B S. (2003) *Curr Opin Struct Biol* 13, 284-299.
19. Kielkopf, C L, Baird, E E, Dervan, P D & Rees, D C. (1998) *Nat Struct Biol* 5, 104-109.
20. White, S, Szewczyk, J W, Turner, J M, Baird, E E & Dervan, P B. (1998) *Nature* 391, 468-471
21. Olenyuk, B Z, Zhang, G J, Klco, J M, Nickols, N G, Kaelin, W G & Dervan, P B. (2004) *Proc Natl Acad Sci USA* 101, 16768-16773.
22. Nickols, N G, Jacobs, C S, Farkas, M E & Dervan, P B. (2007) *Nucleic Acids Res* 35, 363-370.
23. DePrimo, S E, Diehn, M, Nelson, J B, Reiter, R E, Matese, J, Fero, M, Tibshirani, R, Brown, P O & Brooks, J D. (2002) *Genome Biol* 3, research0032.1-research0032.12.
24. Magee, J A, Chang, L W, Stormo, G D & Milbrandt, J. (2006) *Endocrinology* 147, 590-598.
25. Nelson, P S, Clegg, N, Arnold, H, Ferguson, C, Bonham, M, White, J, Hood, L & Lin, B Y. (2002) *Proc Natl Acad Sci USA* 99, 11890-11895.
26. Mitchell, S H, Murtha, P E, Zhang, S B, Zhu, W & Young, C Y F. (2000) *Mol Cell Endocrino1* 168, 89-99.
27. Tomlins, S A, Rhodes, D R, Perner, S, Dhanasekaran, S M, Mehra, R, Sun, X W, Varambally, S, Cao, X H, Tchinda, J & Kuefer, R, et al. (2005) *Science* 310, 644-648.
28. Darnell, J E. (2002) *Nat Rev Cancer* 2, 740-749.
29. Pandolfi, P P. (2001) *Oncogene* 20, 3116-3127.
30. Mellinghoff, I K, Vivanco, I, Kwon, A, Tran, C, Wongvipat, J & Sawyers, C L. (2004) *Cancer Cell* 6, 517-527.
31. Chen, T S, Wang, L H & Farrar, W L. (2000) *Cancer Res* 60, 2132-2135.
32. Tomlins, S A, Mehra, R, Rhodes, D R, Smith, L R, Roulston, D, Helgesson, B E, Cao, X H, Wei, J T, Rubin, M A & Shah, R B, et al. (2006) *Cancer Res* 66, 3396-3400.
33. Burnett, R, Melander, C, Puckett, J W, Son, L S, Wells, R D, Dervan, P B & Gottesfeld, J M. (2006) *Proc Natl Acad Sci USA* 103, 11497-11502.
34. Shaffer, P L, Evan, A, Dollins, D E, Claessens, F & Gewirth, D T. (2004) *Proc Natl Acad Sci USA* 101, 4758-4763.
35. Luisi, B F, Xu, W X, Otwinowski, Z, Freedman, L P, Yamamoto, K R & Sigler, P B. (1991) *Nature* 352, 497-505.
36. Schwabe, J W R, Chapman, L, Finch, J T & Rhodes, D. (1993) *Cell* 75, 567-578.
37. Pavletich, N P & Pabo, C O. (1991) *Science* 252, 809-817.
38. Gearhart, M D, Dickinson, L, Ehley, J, Melander, C, Dervan, P B, Wright, P E & Gottesfeld, J M. (2005) *Biochemistry* 44, 4196-4203.

39. Nguyen-Hackley, D H, Ramm, E, Taylor, C M, Joung, J K, Dervan, P B & Pabo, C O. (2004) *Biochemistry* 43, 3880-3890.
40. Klein, K A, Reiter, R E, Redula, J, Morad, H, Zhu, X L, Brothman, A R, Lamb, D J, Marcelli, M, Belldegrun, A & Witte, O N, et al. (1997) *Nat Med* 3, 402-408.
41. Ellwood-Yen, K, Wongvipat, J & Sawyers, C. (2006) *Cancer Res* 66, 10513-10516.
42. Iyer, M, Salazar, F B, Lewis, X, Zhang, L, Wu, L, Carey, M & Gambhir, S S. (2005) *Transgenic Res* 14, 47-55.
43. Belitsky, J M, Nguyen, D H, Wurtz, N R & Dervan, P B. (2002) *Bioorg Med Chem* 10, 2767-2774.
44. Trauger, J W & Dervan, P B. (2001) *Methods Enzymol* 340, 450-466.
45. Zhang, J Y, Zhang, S B, Murtha, P E, Zhu, W, Hou, S S M & Young, C Y F. (1997) *Nucleic Acids Res* 25, 3143-3150.
46. Wang J C, Derynck M K, Nonaka D F, Khodabakhsh D B, Haqq C, Yamamoto K R. (2004) *Proc Natl Acad Sci USA*. 44, 15603-15608.
47. So A Y, Chaivorapol C, Bolton E C, Li H, Yamamoto K R. (2007) *PLoS Genet.* 6. e94.
48. Kumar V, Green S, Stack G, Berry M, Jin J R, Chambon P. (1987) *Cell.* 51, 941-51.
49. Sabnis G J, Jelovac D, Long B, Brodie A. (2005) *Cancer Res.* 65, 3903-10.
50. Moy B, Goss P E. (2006) *Clin Cancer Res.* 12, 4790-3.

Example 4

4.1 Abstract

Many cancer therapeutics target DNA and exert cytotoxicity through the induction of apoptosis by DNA damage and inhibition of transcription. We report that a DNA minor groove binding hairpin pyrrole-imidazole (Py-Im) polyamide interferes with RNA polymerase II (RNAP2) activity in cell culture. Polyamide treatment activates p53 signaling in LNCaP prostate cancer cells without detectable DNA damage. Genome-wide mapping of RNAP2 binding shows reduction of occupancy preferentially at transcription start sites (TSS), while occupancy at enhancer sites are unchanged. Polyamide treatment results in a time- and dose-dependent depletion of RNAP2 large subunit RPB1 that is preventable with proteasome inhibition. This polyamide demonstrates antitumor activity in a prostate tumor xenograft model with limited host toxicity.

4.2 Introduction

Several chemotherapeutics including the anthracyclines and cisplatin exert part of their cytotoxicity through the inhibition of transcription (1). Transformed cells often require constant expression of anti-apoptotic genes for survival, making transcription inhibition a relevant therapeutic strategy in oncology (1, 2). Many radio- and chemotherapy treatments that target DNA, including UV irradiation, cisplatin, and the topoisomerase inhibitors, introduce obstacles to RNAP2 elongation by generating bulky or helix distorting lesions (3-5). In cell culture experiments, transcription blockade has been shown to induce the degradation of the RNAP2 large subunit (RPB1), and function as a signal for p53 mediated apoptosis (6, 7). While many DNA targeted therapeutics effectively inhibit transcription and induce apoptosis, clinical treatment with genotoxic agents can also damage DNA in normal cells, increasing symptomatic toxicity and potentially leading to secondary cancers (8). The question arises whether high affinity, non-covalent DNA-binding ligands offer an approach to transcription inhibition without DNA damage.

Hairpin Py-Im polyamides are synthetic oligomers with programmable sequence recognition that bind the minor groove of DNA with high affinity (9). Py-Im polyamide-DNA binding induces allosteric changes in the DNA helix that can interfere with protein-DNA interactions (10, 11). Py-Im polyamides have been used as molecular probes in cell culture to modulate inducible gene expression pathways (12-14). In rodents, 8-ring hairpin Py-Im polyamides circulate in blood for several hours after administration, and affect changes in gene expression in tissues (15-17).

We have previously reported that polyamide 77 (FIG. 19), which targets the sequence 5'-WGWWCW-3' found in the androgen response element, inhibited a subset of dihydrotestosterone (DHT) induced genes in LNCaP cells (12). Here, we explore the effects of this polyamide on the RNAP2 transcription machinery. We find that RNAP2 is preferentially reduced from transcription start sites genome-wide without significant perturbation at enhancer loci. This is accompanied by proteasome dependent degradation of the RNAP2 large subunit RPB1. Polyamide treatment induces p53 accumulation that is consistent with what is observed for other transcription inhibitors that interact with DNA (4, 5), but without evidence of DNA damage. This polyamide demonstrates efficacy in vivo against prostate cancer xenografts in mice with limited host toxicity.

4.3 Results 4.3.1 The Effects of Polyamide 1 on Global Occupancy of RNAP2

Polyamide 77 was previously shown to inhibit the induction of a subset of DHT driven genes in LNCaP cell culture (12). We interrogated the effects of 77 on the RNAP2 transcription machinery by mapping the global occupancy of RNAP2 using ChIP-seq. Under DHT induction, select androgen receptor (AR) driven genes, such as KLK3, showed increased RNAP2 occupancy over genic regions, which was decreased in the presence of 77 (FIG. 20A). While RNAP2 occupancy across constitutively expressed genes such as GAPDH did not change with DHT induction, cotreatment with 77 reduced RNAP2 occupancy across these genes (FIG. 20B). This reduction in RNAP2 occupancy by 77 was in the context of a global decrease of RNAP2 occupancy across genic regions (FIG. 24), particularly at transcription start sites (TSS) (FIG. 20C). However, 77 did not significantly change RNAP2 occupancy at enhancer loci (FIG. 20D), suggesting 77 may affect the active elongation of RNAP2 without disturbing the transcription apparatus anchored at enhancers, and that the observed differences in RNAP2 occupancy are not due to technical variation in ChIP success between experiments. Reduction in DNA occupancy of RNAP2 has also been reported in cells treated with α-amanitin, a cyclic octapeptide inhibitor of RPB1 (18).

Inhibition of RNAP2 elongation can be caused by a multitude of genotoxic agents and often results in the degradation of the RPB1 subunit (3, 19, 20). Indeed, in addition to reduced RNAP2 DNA occupancy, immunoblot analysis of LNCaP cells treated with 77 shows depletion of RPB1 in a time- and concentration-dependent manner (FIG. 20E). To examine if the effects of RPB1 degradation was transcription dependent we measured levels of RPB1 mRNA (FIG. 20F). The expression of RPB1 modestly increased with polyamide treatment, suggesting this depletion is post-transcriptional.

4.3.2 Polyamide Cytotoxicity is Reduced by Proteasomal Inhibition and Serum Starvation Inhibition of RNAP2 has been reported to induce apoptosis (4, 6, 21), and may contribute to polyamide cytotoxicity observed in LNCaP cells cultured with 77 (FIG. 21A). A previous study with trabectidin, a DNA minor groove alkylator that causes RPB1 degradation, showed the toxicity induced by the molecule can be reduced by cotreatment with the proteasome inhibitor MG132 (21). To evaluate if polyamide-induced toxicity was also reducible by proteasomal inhibition we treated LNCaP cells with 85 in the presence and absence of MG132. We developed analog 85 specifically for this application because prolonged incubation with MG132 alone is cytotoxic, and conjugation of an aryl group to the γ-aminobutyric acid turn have been shown to improve cellular uptake and cytotoxicity of polyamides. Cell viability experiments showed that 85 induced cell death more rapidly than 77 without significant change to DNA binding (FIG. 25A-B). Cell culture experiments revealed coincubation with MG132 reduced cytotoxicity induced by 85 (FIG. 21B) and prevented degradation of RPB1 (FIG. 21C). Polyamide nuclear uptake was not affected by MG132 (FIG. 25C-D). In addition, cytotoxicity studies of cells treated with UV radiation and α-amanitin have shown increased cellular sensitivity to transcription inhibition upon S phase entry (6, 22). Similarly, 85 was less toxic to LNCaP cells arrested in $G_1/G_0$ by serum starvation as compared to cells grown in normal media (FIGS. 21D and 25E).

4.3.3 Accumulation of p53 and Expression of p53 Targets in the Absence of DNA Damage Previously published microarray data of LNCaP cells cotreated with DHT and 77 revealed the induction of several p53 target genes (12). Despite depletion of RPB1, treatment of LNCaP cells with 77 alone induced expression of p53 genes that are characteristic of genotoxic stress (FIG. 22A) (23). Many of these genes were previously observed to be induced in A549 cells treated with polyamide as well as polyamide-alkylator conjugates (14, 24). To examine if direct DNA damage was contributing to p53 activity, we looked for evidence of DNA damage in LNCaP cells after extended treatment with 77. Alkaline comet assay showed no evidence of DNA fragmentation (FIG. 22B). Additionally, treatment with 77 did not induce cellular markers of DNA damage including phosphorylation of γH2A.X, ATM, DNA-PKcs, p53, or Chk2 (FIG. 22C). However, modest accumulation of p53 and PARP cleavage were observed. This data suggest that 77 activates p53 through transcriptional inhibition without DNA damage, a mechanism that has been observed for non-DNA targeting agents that exert transcriptional stress such as the protein kinase inhibitor 5,6-dichlorobenzimidazole (DRB) and α-amanitin(5, 6, 25).

4.3.4 Effects of Polyamide Treatment on Prostate Cancer Xenografts

We recently reported the toxicity and pharmacokinetic (PK) profile of 77 in mice (16). Subcutaneous (SC) injection of 77 also results in detectable circulation (FIG. 26). We thus selected this molecule for further testing against xenografts in vivo. Male NSG mice bearing LNCaP xenografts were treated with either vehicle or 20 nmol (~1 mg/kg) 77 by SC injection once every 3 days for a cycle of three injections. At the experimental end point, mice treated with 77 had smaller tumors and lower serum PSA as compared to vehicle controls (FIG. 23A-B). Immunohistological analysis of selected tumors showed evidence of cell death by TUNEL stain (FIG. 23C). While tumor-free NSG mice treated with 77 under this regimen showed no signs of distress or weight loss, LNCaP tumor-bearing NSG mice exhibited weight loss by the experimental end point (FIG. 27). This was accompanied by an elevation in serum uric acid that was not observed in either control group (FIG. 23D).

4.4 Discussion

DNA targeting agents including cisplatin, the anthracyclines, minor groove binders and UV radiation have been demonstrated to affect a multitude of DNA dependent enzymes such as the RNA polymerases, DNA polymerase, topoisomerases, and helicases (21, 27, 28). Our research group and others have used polyamides as molecular tools to modulate gene expression programs (12-14, 29). The programmable sequence specificity of Py-Im polyamides offers a unique mechanism to target specific transcription factor-DNA interfaces and thereby modulate particular gene expression pathways. In previous studies we focused our analysis on specific changes to inducible pathways of gene expression. For example, we have shown polyamide 77 affects approximately 30% of the DHT-induced transcripts in LNCaP cells, which may result from inhibition of the transcription factor AR-DNA interface (12). However, the cellular cytotoxicity of this polyamide may not be due to only inhibition of DHT-induced gene expression since analogs of 77 exhibits toxicity in a variety of cancer cells (26). It is more likely that polyamides perturb a multitude of DNA dependent cellular processes (transcription, replication) that contribute to cytotoxicity. In this study we show that 77 interferes with RNAP2 elongation resulting in the degradation of RPB1, activation of p53, and triggering of apoptosis, without detectable genomic damage.

Our previous study has shown polyamide 77 decreased the expression of a large number of genes in LNCaP cells (12). To examine the effect of 77 on the transcription machinery we performed genome-wide mapping of RNAP2 occupancy by ChIP-seq. We found that while DHT induction increased RNAP2 occupancy at select AR driven genes, cotreatment with 77 caused a genome-wide decrease of RNAP2 occupancy across genic regions. The effect was most pronounced at transcription start sites. Interestingly, RNAP2 occupancy at enhancer loci, where the transcription assemblies may be attached to via contacts through other proteins, was not significantly affected by polyamide treatment. This suggests polyamide 77 may preferentially affect RNAP2 loading at regions where RNAP2 is actively engaged, a mechanism that has been previously proposed for the gene regulatory activity of polyamides (27).

The displacement of RNAP2 from DNA is caused by many DNA damaging agents that pose an impediment to RNAP2 elongation, this effect is normally coupled with the degradation of large RNAP2 subunit RPB1. Indeed, the cellular level of RPB1 in LNCaP cells was found to decrease in both a time- and concentration-dependent manner when treated with polyamide 77. Polyamide 85, a more cytotoxic analog of 77, also reduced cellular RPB1 in LNCaP cells and induced cell death. Cotreatment of 85 with a proteasomal inhibitor MG132 was able to prevent the degradation of RPB1 and reduce the toxicity of 85 in cell culture. In addition, the cytotoxic effects of other RNAP2 inhibitors were found to be attenuated by preventing S phase entry. LNCaP cells arrested in $G_0/G_1$ by serum starvation also exhibited reduced sensitivity to 85 as compared to cells grown in normal media. The finding that cytotoxicity is partially rescued by MG132 treatment and $G_0/G_1$ arrest, suggests RPB1 degradation contributes to cytotoxicity; however, contributions from other DNA dependent processes are not ruled out.

While transcription inhibition can activate p53 signaling, both events can be caused by DNA damage. Analysis of previously published microarray data revealed the induction of several p53 target genes in LNCaP cells cotreated with DHT and 77 (12). Further validation of transcript levels of these genes in this study also showed a time dependent increase in the expression of GADD45A, MDM2, IGFBP3, P21, BAX and DDIT3 (FIG. 22A). Since these genes are also markers of genotoxic stress (23), and were found to be induced in A549 cells treated with alkylating polyamide derivatives (24), we searched for signs of DNA damage to determine if it was causing transcription inhibition and p53 activation. Interestingly, both comet assay and immunoblot analysis of cellular DNA damage markers showed no significant signs of DNA damage. While faint phosphorylation of γH2A.X was visible, it is likely caused by cellular apoptosis as indicated by the concurrent PARP cleavage. This data is consistent with studies in yeast mutants that are hypersensitive to DNA damage, which showed no increased sensitivity to polyamide treatment, suggesting these reversible DNA binders do not compromise genomic integrity (28).

The activation of p53 by transcription inhibition in the absence of DNA damage has been observed for DNA independent inhibitors of RNAP2 such as DRB, alpha-amanitin, and various RNAP2 targeted antibodies (5, 6, 25). Distamycin A, the natural product, which provided the structural inspiration for Py-Im polyamides, inhibits the initiation of RNA synthesis in cell-free assays (29). In cell culture, distamycin also induces degradation of RPB1 and activates p53 (30, 31). However, low antitumor potency and poor stability limit its utility.

To assess the therapeutic potential of polyamide 77 as an antitumor agent, LNCaP xenografts in a murine model were treated with 77 or PBS vehicle. After three rounds of treatment, tumor growth was found to be reduced by 64% in the treated group. While treatment with 77 alone did not cause changes in animal body weight or obvious signs of toxicity in tumor free animals, treatment in tumor bearing animals resulted in weight loss after 3 treatments. The accompanied elevation in serum uric acid may be an indication of tumor lysis syndrome (32) that is associated with rapid tumor cell turnover upon polyamide treatment. We anticipate that Py-Im polyamides could also demonstrate efficacy in additional xenograft models.

4.5 Methods 4.5.1 Compounds and Reagents

Py-Im polyamides 77, 85 and 86 were synthesized on oxime resin as described (26, 33, 34). (R)-MG132 (MG132) was from Santa Cruz Biotechnology.

4.5.2 Cell Viability Assays

LNCaP cells were plated in clear bottom 96 well plates at 5,000-7,500 cells per well. The cells were allowed to adhere for 24-36 h before compounds were added in fresh media. Cell viability was determined by the WST-1 assay (Roche) for 77 and 85 after 24 h or 72 h incubation with cells. Cells in cytotoxicity rescue experiments were treated with 85 alone or with 3 μM for 24 h. For cell cycle arrest experiments LNCaP cells were seeded at 2,500-5,000 cells per well in normal media and allowed to adhere for 24-36 h. The media was replaced with media supplemented with 0.5% FBS and incubated for 48 h prior to treatment with compound.

4.5.3 In Vivo Xenografts Experiments

All mice experiments were conducted under an approved protocol by the Institutional Animal Care and Use Committee of the California Institute of Technology. Male NOD scid gamma (NSG) mice were purchased from The Jackson Laboratory. The animals were individually caged and maintained on a standard light-dark cycle. NSG mice were engrafted with LNCaP cells (2.5 million cells) in a mixture of 1:1 media and matrigel in the left flank. Tumors were grown to ~100 mm$^3$ (L×W$^2$) before beginning treatment with compound or vehicle. Py-Im polyamide 77 was administered once every 3 days in a 5% DMSO:PBS vehicle solution until the experiment endpoint.

4.5.4 Serum Measurements

To investigate if polyamide 77 could be detected in peripheral blood after SC injections, 120 nmol of 77 (in 5% DMSO/PBS) was injected into the right flank of four C57BL/6 mice. Blood was collected from anesthetized mice via retroorbital collection at 5 minutes, 4 h, and 12 h after injection, then processed by methods previously described and analyzed by HPLC (35). For measurement of serum PSA (KLK3) and uric acid, blood was collected from anesthetized mice via retroorbital collection at experimental endpoint and serum was separated from blood by centrifugation. Serum PSA (KLK3) was measured by ELISA (R&D systems) according to manufacturer's instructions. Uric acid was measured as described (36).

4.5.5 Chromatin Immunoprecipitation

Genomic occupancy of RNA polymerase II was determined by chromatin immunoprecipitation (ChIP) with the 4H8 antibody (Abcam). LNCaP cells were plated at 35 million cells per plate in RPMI supplemented with 10% CTFBS and allowed to adhere for 24-36 h. The cells were treated with compound 77 in fresh media (10% CTFBS) for 48 h. Cells treated and untreated with 77 were incubated with 1 nM DHT for 6 h. Two step crosslinking was performed as previously described (37). After DSG removal, chromatin was immunopreciated by previously published methods (38). DNA was harvested by phenol chloroform extraction and purified with the QIAquick purification kit (Qiagen). Quantitative PCR was used to validate enrichment at the GAPDH transcription start site (Primers: F-GGTTTCTCTCCGCCCGTCTT (SEQ ID NO:18), R-TGTTCGACAGTCAGCCGCAT (SEQ ID NO:19)) compared to an internal negative locus (Primers: F-TAGAAGGGGGATAGGGGAAC (SEQ ID NO:20), R-CCAGAAAACTGGCTCCTTCTT (SEQ ID NO:21)). Each sample was immunoprecipated as 5 technical replicates. The 3 most consistent samples were combined and submitted for sequencing on an Illumina genome analyzer. Biological replicates were acquired.

4.5.6 Data Processing and Analysis

Sequencing reads were trimmed down to 36 bp and then mapped against the male set of human chromosomes (excluding all random chromosomes and haplotypes) using the hg19 version of the human genome as a reference. Bowtie 0.12.7 was used for aligning reads (39), with the following settings: "-v 2-t—best—strata". Signal profiles over genomic locations were generated using custom written python scripts; the refSeq annotation was used for gene coordinates. Enhancers and promoters were defined using previously published histone marker data (40). ChIP-seq peaks were called using MACS2 with default settings (41). Enhancers were defined as H3K4me1-positive regions that did not intersect with H3K4me3-positive regions and promoters as H3K4me3-positive regions that did not intersect with H3K4me1-positive regions. Clustering was performed with Cluster 3.0 (42) and visualized with Java TreeView (43).

4.5.7 Comet Assay

LNCaP cells were plated at 1 million cells per 10 cm plate and allowed to adhere for 24 to 36 h. Cells were then incubated with either 10 μM 77 for 48 h or 5 μM doxorubicin for 4 h. DNA damage was assayed using the Trevigen CometAssay® system and samples were prepared from harvested cells according to the manufacture protocol. Comets were imaged on a confocal microscope (Exciter, Zeiss) at 10× magnification. Percentage of DNA in the tail was determined using Comet Assay Lite IV (Perceptive Instruments). More than one hundred comets were scored for each condition.

4.5.8 Immunoblot Assay

Samples for immunoblot analysis were prepared by plating LNCaP or DU145 cells at 1 million cells per 10 cm plate. Cells were allowed to adhere for 24-36 hr prior to incubation with compound. After the appropriate incubation time cells were washed once with ice cold PBS and harvested in ice cold 125 μL lysis buffer (50 mM Tris-HCl pH 7.4, 150 mM NaCl, 1 mM EDTA, 1% Triton X100) containing protease inhibitor cocktail (Roche), 1 mM PMSF (Sigma), and phosphatase inhibitors (Sigma). Samples were allowed incubate on ice for 10 min with vortexing once every 3 min. Cellular debris was pelleted by spinning at 14,000 rpm for 15 min to collect the supernatant. Samples were then quantified for protein content with the Bradford assay (Bio-rad) and boiled with 4× sample buffer (Li-Cor) for 5 min. Protein electrophoresis was performed in 4-20% precast Tris glycine SDS gels (Bio-rad) and transferred to PVDF membranes. Membrane blocking was done with Odyssey Blocking Buffer (Li-Cor). The following antibodies used to probe changes in protein levels or phosphorylation states: RBP1 (Santa Cruz Biotechnology, N20), p53 (Santa Cruz Biotechnology, DO1), phospho-Chk2-Thr68 (Cell Signaling Technology), Phospho-p53-Ser15 (Cell Signaling Technology), phosphor-H2A.X-Ser139 (Cell Signaling Technology), phosphor-ATM-Ser1981 (Abcam), phosphor-DNA-PKcs-Ser2056 (Abcam), and β-actin (Abcam). Near-IR secondary antibodies (Li-Cor) were used for imaging. Experiments were performed in biological replicates.

4.5.9 Flow Cytometry

To determine cell cycle distribution of LNCaP cells grown in normal media or under serum starved conditions 1 million cells were seeded to each 10 cm plate and allowed to adhere for 24-36 h. Media was then replaced with fresh normal media (10% FBS) or serum starved media (0.5% FBS) and incubated for an additional 48 h. Cells were then trypsinized and prepared for analysis as previously described (44). Samples were analyzed in biological triplicate on a FACSCalibur (Becton-Dickinson) instrument. Data analysis was performed using FlowJo 7.6.5.

4.5.10 Quantitative RT-PCR

RNA was extracted using RNEasy columns (Qiagen) according to manufacturer's protocols. cDNA was generated from RNA by reverse transcriptase (Transcriptor First Strand cDNA kit, Roche). Quantitative real-time RT-PCR was performed using SYBR Green PCR Master Mix (Applied Biosystems) on an ABI 7300 instrument. mRNA was measured relative to β glucuronidase as an endogenous control. Table 6 shows the primer sequences.

TABLE 6

| Gene | Forward (5'-3') | Reverse (5'-3') |
|---|---|---|
| P21 | GCCATTAGCGCATCACAGT (SEQ ID NO: 22) | ACCGAGGCACTCAGAGGAG (SEQ ID NO: 23) |
| GADD45a | GCAGGATCCTTCCATTGAGA (SEQ ID NO: 24) | CTCTTGGAGACCGACGCTG (SEQ ID NO: 25) |
| MDM2 | CTGATCCAACCAATCACCTG (SEQ ID NO: 26) | AAGCCTGGCTCTGTGTGTAA (SEQ ID NO: 27) |
| IGFBP3 | CGGTCTTCCTCCGACTCAC (SEQ ID NO: 28) | CTCTGCGTCAACGCTAGTGC (SEQ ID NO: 29) |
| BAX | CAGCCCATGATGGTTCTGAT (SEQ ID NO: 30) | GACATGTTTTCTGACGGCAA (SEQ ID NO: 31) |
| RPB1 | CTCAATCACCCCCTGCC (SEQ ID NO: 32) | GAGTCCTGAGTCCGGATGAA (SEQ ID NO: 33) |
| GUSB | CTCATTTGGAATTTTGCCGATT (SEQ ID NO: 34) | CCGAGTGAAGATCCCCTTTTT (SEQ ID NO: 35) |

4.5.11 Confocal Microscopy

Cells were plated in 35 mm optical dishes (MatTek) and dosed with polyamide 86 at 2 μM for 24 hours with or without 3 μM MG132. Cells were then washed with PBS and imaged on a confocal microscope (Exciter, Zeiss) using a 63× oil immersion lens. Confocal imaging was performed following established protocols (33).

4.5.12 Histology and Immunohistochemistry

Tumors were resected immediately after euthanasia and fixed in neutral buffered formalin. Selected samples were embedded in paraffin, sectioned and stained with hematoxylin and eosin (H&E). Selected sections were assessed by deoxynucleotidyltransferase dUTP nick-end labeling (TUNEL) as described (45).

4.5.13 Thermal Denaturation Assays

Polyamides 77 and 85 were incubated with duplex DNA 5'-CGA<u>TGTTCA</u>AGC-3' (SEQ ID NO:36), which contains the predicted target site for these compounds (underscore). Melting temperature analyses were performed on a Varian Cary 100 spectrophotometer as described (46). Melting temperatures were defined as a maximum of the first derivative of absorbance at 260 nm over the range of temperatures.

4.5.14 Statistical Analysis

Statistical significance was calculated using the student's t test with two tailed variance. Results were considered significant when p<0.05.

References for Example 4

1. Derheimer F A, Chang C W, & Ljungman M (2005) *Eur. J. Cancer* 41(16):2569-2576.
2. Koumenis C & Giaccia A (1997) *Mol. Cell. Biol.* 17(12):7306-7316.
3. Jung Y & Lippard S J (2006) *J. Biol. Chem.* 281(3):1361-1370.
4. Ljungman M & Zhang F F (1996) *Oncogene* 13(4):823-831.
5. Ljungman M, Zhang F F, Chen F, Rainbow A J, & McKay B C (1999) *Oncogene* 18(3):583-592.
6. Arima Y, et al. (2005) *J. Biol. Chem.* 280(19):19166-19176.
7. Nguyen V T, et al. (1996) *Nucleic Acids Res.* 24(15):2924-2929.
8. Arseneau J C, et al. (1972) *N Engl J Med* 287(22):1119-1122.

9. Dervan P B & Edelson B S (2003) *Curr. Opin. Struct. Biol.* 13(3):284-299.
10. Chenoweth D M & Dervan P B (2009) *Proc. Natl. Acad. Sci. U.S.A.* 106(32):13175-13179.
11. Chenoweth D M & Dervan P B (2010) *J. Am. Chem. Soc.* 132(41):14521-14529.
12. Nickols N G & Dervan P B (2007) *Proc. Natl. Acad. Sci. U.S.A.* 104(25):10418-10423.
13. Nickols N G, Jacobs C S, Farkas M E, & Dervan P B (2007) *ACS Chem. Biol.* 2(8):561-571
14. Muzikar K A, Nickols N G, & Dervan P B (2009) *Proc. Natl. Acad. Sci. U.S.A.* 106(39):16598-16603.
15. Matsuda H, et al. (2011) *Kidney Int.* 79(1):46-56.
16. Synold T W, et al. (2012) *Cancer Chemother Pharmacol.*
17. Raskatov J A, et al. (2012) *Proc. Natl. Acad. Sci. U.S.A.* 109(40):16041-16045.
18. Palstra R J, et al. (2008) *PloS one* 3(2).
19. Bregman D B, et al. (1996) *Proc. Natl. Acad. Sci. U.S.A.* 93(21):11586-11590.
20. Ratner J N, Balasubramanian B, Corden J, Warren S L, & Bregman D B (1998) *J. Biol. Chem.* 273(9):5184-5189.
21. Aune G J, et al. (2008) *Clin. Cancer Res.* 14(20):6449-6455.
22. McKay B C, Becerril C, Spronck J C, & Ljungman M (2002) *DNA Repair* 1(10):811-820.
23. El-Deiry W S (1998) *Semin. Cancer Biol.* 8(5):345-357.
24. Kashiwazaki G, et al. (2012) *J. Med. Chem.* 55(5):2057-2066.
25. Derheimer F A, et al. (2007) *Proc. Natl. Acad. Sci. U.S.A.* 104(31):12778-12783.
26. Meier J L, Montgomery D C, & Dervan P B (2012) *Nucleic Acids Res.* 40(5):2345-2356.
27. Carlson C D, et al. (2010) *Proc. Natl. Acad. Sci. U.S.A.* 107(10):4544-4549.
28. Marini N J, et al. (2003) *Chem. Biol.* 10(7):635-644.
29. Puschendorf B, Petersen E, Wolf H, Werchau H, & Grunicke H (1971) *Biochem. Biophys. Res. Commun.* 43(3):617-624.
30. Zhang Z, et al. (2009) *Biochem. Pharmacol.* 78(10):1316-1322.
31. Hirota M, Fujiwara T, Mineshita S, Sugiyama H, & Teraoka H (2007) *Int. J. Biochem. Cell Biol.* 39(5):988-996.
32. Coiffier B, Altman A, Pui C H, Younes A, & Cairo M S (2008) *J. Clin. Oncol.* 26(16):2767-2778.
33. Best T P, Edelson B S, Nickols N G, & Dervan P B (2003) *Proc. Natl. Acad. Sci. U.S.A.* 100(21):12063-12068.
34. Puckett J W, Green J T, & Dervan P B (2012) *Org. Lett.* 14(11):2774-2777.
35. Raskatov J A, Hargrove A E, So A Y, & Dervan P B (2012) *J. Am. Chem. Soc.* 134(18):7995-7999.
36. Dai K S, et al. (2005) *Clin. Biochem.* 38(3):278-281.
37. Nowak D E, Tian B, & Brasier A R (2005) *BioTechniques* 39(5):715-725.
38. Reddy T E, et al. (2009) *Genome Res.* 19(12):2163-2171.
39. Langmead B, Trapnell C, Pop M, & Salzberg S L (2009) *Genome Biology* 10(3).
40. Yu J D, et al. (2010) *Cancer cell* 17(5):443-454.
41. Zhang Y, et al. (2008) *Genome Biol.* 9(9):R137.131.
42. de Hoon M J, Imoto S, Nolan J, & Miyano S (2004) *Bioinformatics* 20(9):1453-1454.
43. Saldanha A J (2004) *Bioinformatics* 20(17):3246-3248.
44. Diamond R A & DeMaggio S (2000) *In living color: protocols in flow cytometry and cell sorting* (Springer, Berlin; N.Y.) pp xxv, 800 p.
45. Zisman A, et al. (2003) *Cancer Res.* 63(16):4952-4959.
46. Dose C, Farkas M E, Chenoweth D M, & Dervan P B (2008) *J. Am. Chem. Soc.* 130(21):6859-6866.

Example 5

5.1 Abstract

A hairpin pyrrole-imidazole polyamide (77) targeted to the androgen receptor consensus half-site was found to exert antitumor effects against prostate cancer xenografts. A previous animal study showed 77, which has a chiral amine at the α position of the γ-aminobutyric acid turn (γ-turn), did not exhibit toxicity at doses less than 10 mg/kg. In the same study, a polyamide with an acetamide at the β position of the γ-turn resulted in animal morbidity at 2.3 mg/kg. To identify structural motifs that cause animal toxicity we synthesized polyamides 77-80 with variations at the α and β positions in the γ-turn. Weight loss, histopathology, and serum chemistry were analyzed in mice post-treatment. While serum concentration was similar for all four polyamides after injection, dose limiting liver toxicity was only observed for three polyamides. Polyamide 78, with an α-acetamide, caused no significant evidence of rodent toxicity and retains activity against LNCaP xenografts.

5.2 Introduction

Prostate cancer is a major contributor of cancer death in American males (1). The malignant transformation of prostate epithelial tissue is caused by an altered pattern of gene expression driven by the androgen receptor (AR). Clinically, localized prostate cancer is curable by surgery or radiation (2, 3). Advanced prostate cancer is treated with systemic therapies that target testosterone signaling (enzalutamide, abiraterone), immunotherapy (sipuleucel T), and taxane-based chemotherapy (docetaxel, cabazitaxel) (4). These new agents have shown survival benefits to patients with castration resistant, metastatic disease. However, all patients will eventually progress on these drugs. Resistance to the second-generation antiandrogen enzalutamide and the CYP17 inhibitor abiraterone may be due to the action of splice variants of AR that lack the ligand-binding domain (AR-V) (5, 6). Therefore, therapy resistant prostate cancer is an unmet clinical need, and novel systemic therapies are needed in patients after these treatments have failed (4).

Direct interference of AR driven transcription at the protein-DNA interface is a strategy that can circumvent resistance conferred by AR-V. Genomic DNA is the predominant target of many chemo- and radio-therapies. The interactions of these therapies with DNA result in the inhibition of DNA-dependent processes that are over-active in cancer cells such as transcription (7-9). While AR driven transcription can be inhibited by DNA-targeted agents (10, 11), most conventional DNA-targeted therapeutics are genotoxic and can induce secondary malignancies (12). DNA-damaging agents may also contribute to tumor metastasis through effects on non-cancerous cells in the tumor microenvironment (13). Small molecules that interact with DNA without genotoxicity could be a significant advance over conventional DNA-targeted therapeutics.

Pyrrole (Py)-Imidazole (Im) polyamides are minor groove binders that have been shown to affect gene expression in a number of inducible transcription systems (14-20). As non-covalent DNA-binding oligomers, these compounds form specific hydrogen bonds to the minor groove floor with programmable sequence recognition and high affinity (21-

23). Py-Im polyamides are toxic to a variety of cancer cell lines, including prostate cancer, and exhibit no apparent genotoxicity (24). A typical hairpin oligomer consists of eight aromatic amino acid rings joined in the middle by a γ-aminobutyric acid (γ-turn) (25). While sequence recognition is predominately directed by the antiparallel pairing of N-methylpyrrole and N-methylimidazole carboxamides, structural modifications to the γ-turn, such as substitution at the prochiral α and β positions, have been shown to influence the DNA affinity (26), cell uptake, and the biological activity of polyamides in both cell culture and animals (27, 28).

To date, we have reported the pharmacokinetic (PK) profiles of two eight-ring hairpin-polyamides targeted to the androgen response element half-site 5'-WGWWCW-3' (W=A or T) in mice. The oligomers 77 and 80 of primary sequence ImPyPyPy-γ-ImPyPyPy~NHMe~IPA (FIG. 28) differ in substitution at the γ-turn and were found to have distinct PK profiles. Both compounds were bioavailable in serum after intravenous injection for more than 24 hours, however 80 was found to have longer retention in both the serum and tissues. Both compounds were minimally excreted through the feces, but significant renal clearance was exclusive to 80 (28). In addition to differences in the PK profiles, hairpins 77 and 80 also exhibited different degrees of toxicity to female C57BL/6J mice. While single subcutaneous administrations of 77 in female mice at 2.5 mg/kg and 5 mg/kg did not adversely affect the animals, escalated dosing to 10 mg/kg resulted in weight loss greater than 15%. In comparison, 80 caused acute animal toxicity in addition to weight loss at 2.3 mg/kg and 4.5 mg/kg (28). To dissect the differences in toxicities, there are two variables on the turn that must be sorted out (α versus β position and amino versus acetamide substitution).

More recently oligomer 77 was found to suppress the growth of LNCaP xenografts in immunocompromised mice after three subcutaneous injections at 1 mg/kg (24). Thus, a systematic toxicity study of 77 and related polyamides with modifications to the γ-turn may yield structures with reduced animal toxicity. In addition, an extensive toxicity study of polyamides in animals to identify target organs of pathology is a necessary step towards translation of this technology into the clinic.

In this paper, we report the animal toxicity of four structurally related polyamides with identical Py-Im sequence but with different substitutions at the γ-turn (FIG. 28), a change that does not alter binding sequence preference. We assessed mouse weight, organ histopathology, and serum chemistry in wild type male mice after single and multiple dosing regimens. Dose limiting toxicity was observed at the highest dose for three of the four molecules. From this study, we have identified one polyamide that demonstrates no detectable toxicity by histopathology or serum analysis after single or repeated subcutaneous injections.

5.3 Results

5.3.1 Selection of Py-Im Polyamides

We synthesized four structurally related polyamides (FIG. 28) that have an identical Py-Im sequence ImPyPyPy-γ-ImPyPyPy~NHMe~IPA. These polyamides demonstrate thermal stabilization of DNA duplexes containing their target sequence (FIG. 34). Polyamide 77, ImPyPyPy-2-(R)$^{H2N}$γ-ImPyPyPy~NHMe~IPA, suppressed LNCaP xenografts in mice (24). Polyamide 79, ImPyPyPy-3-(R)$^{H2N}$γ-ImPyPyPy~NHMe~IPA, differs from 77 in that the γ-turn is substituted at the β position. Polyamide 78, ImPyPyPy-2-(R)$^{AcHN}$γ-ImPyPyPy~NHMe~IPA, differs from 77 in that the primary amine is acetylated. Polyamide 80, ImPyPyPy-3-(R)$^{AcHN}$γ-ImPyPyPy~NHMe~IPA, incorporates both changes from 79 and 78. Our previous report in female mice showed 77 and 80 both circulated in serum after intravenous injection (28). To determine if 77-80 demonstrated comparable serum levels after subcutaneous injection, male C57BL/6J mice were injected with 10 mg/kg each of 77-80 and blood collected by retroorbital bleed at various time points. All polyamides were bioavailable and detectable up to 24 h after subcutaneous injection (FIG. 35).

5.3.2 Escalating Single Dose Subcutaneous Injections

To determine the acute effects of subcutaneous dosing of 77-80 and dose-limiting organ toxicities, 8 week-old male C57BL/6J mice (n=4 per dosing group) were treated with 1, 3, 10 mg/kg 77-80 and observed for 9 days and then sacrificed (FIG. 29). Representative mice (n=2 per dosing group unless otherwise noted) were subjected to histopathology analysis by a veterinary pathologist. Blood from all mice was sampled and sent for analysis of serum markers of target organs. Mice treated with 77 and 79 demonstrated significant weight loss only at 10 mg/kg. Polyamide 80 was only tolerated at 1 mg/kg; all mice treated with 80 at 3 or 10 mg/kg exhibited hunched posture, loss of mobility, and acute morbidity. Mice treated with polyamide 79 at 10 mg/kg demonstrated similar morbidity. These mice were euthanized when significant duress was apparent. All other mice, including those treated with 77 at 10 mg/kg and 78 at all concentrations, demonstrated no change in behavior and appearance.

Histopathology revealed lesions consistent with toxicity in the liver, kidney and spleen in animals receiving a single injection of polyamides 77, 79 and 80. The most severe lesions characterized by diffuse hepatocellular necrosis and apoptosis or multifocal bridging hepatocellular necrosis and apoptosis were identified in animals treated with polyamide 79 at 10 mg/kg and polyamide 80 at both 3 and 10 mg/kg, respectively. Mild hepatocellular necrosis and apoptosis was observed in animals treated with polyamide 77 at doses of 3 and 10 mg/kg, polyamide 79 at 3 mg/kg and polyamide 80 at 1 mg/kg (FIG. 30A). Moderate atypical tubular regeneration (karyomegaly, tubular attenuation, mitotic figures) and/or tubular epithelial necrosis and apoptosis were seen in the kidneys in animals treated with polyamide 79 at 3 mg/kg and polyamide 80 at 3 and 10 mg/kg (FIG. 30B). Milder tubular regeneration and karyomegaly was observed in animals treated with polyamide 77 at 10 mg/kg and polyamide 80 at 1 mg/kg. Mild lymphoid apoptosis in the white pulp of the spleen was noted in animals treated with polyamide 79 at 10 mg/kg and polyamide 80 at 3 and 10 mg/kg. Polyamide 78 demonstrated no detectable toxicity at any dose level tested. No lesions consistent with toxicity were observed in the gastrointestinal tract, heart, lung, pancreas, or stomach in any animals.

Because toxicity to the liver and kidneys were identified as the target organs at risk, serum markers for these organ systems were measured (FIG. 30C). Mice treated with polyamide 77 demonstrated significant elevation of AST, ALT, and total bilirubin at 10 mg/kg, indicative of acute damage to liver cells, and moderate elevation of ALT at 3 mg/kg. Elevation of creatinine and blood urea nitrogen (BUN) was not observed for any dose level of 77. Polyamide 79 treated mice had severe elevation of AST, ALT, and total bilirubin at 10 mg/kg and to a lesser extent at 3 mg/kg. These mice also had elevated BUN at 10 mg/kg. Mice treated with polyamide 80 demonstrated marked and severe elevations of AST, ALT, and total bilirubin at both 3 mg/kg and 10 mg/kg. In addition, these mice had significantly elevated creatinine and BUN at 10 mg/kg, and elevated BUN at 3 mg/kg. Mice treated with polyamide 78 demonstrated no elevation of these markers at the dose levels tested.

In a previous circulation study, it was found that a cyclic form of a hairpin polyamide targeted to the sequence 5'-WG-GWWW-3' had increased animal toxicity (29). However, in addition to the motif change from hairpin to cycle, the γ-turn of the cyclic compound was also changed from a (R)-2,4-diaminobutyric acid turn to (R)-3,4-diaminobutyric acid turn. To determine if the toxicity is dependent on the polyamide shape or the γ-turn, we synthesized cyclic polyamide 87 (FIG. 36). The compound was found to be bioavailable after subcutaneous injection at 10 mg/kg and did not cause significant weight loss in animals. However compound 87 did affect the kidney and liver and caused levels of ALT and AST to increase in a dose dependent manner.

5.3.3 Multiple-Dose Subcutaneous Injections

In addition to single dose injections, the effects of repeated dosing of polyamides 77-80 in mice were examined. In this experiment, 8 week-old male C57BL/6J mice (n=3 per dosing group) were treated with 1 mg/kg of polyamides 77-80 by subcutaneous injection every 3 days, for a cycle of three injections and then sacrificed two days after the final injection (FIG. 31A). As in the single dosing experiments, two mice per group were subjected to histopathology analysis and all blood samples were sent for analysis. Mice treated with 77, 79 and 78 demonstrated no loss in weight or physical morbidities. Two sequential injections of 80 at 1 mg/kg resulted in dramatic weight loss, loss of mobility, and hunched posture within six days (FIG. 31B). These mice were promptly euthanized.

Histopathology of these mice treated with polyamide 77 and 79 revealed mild multifocal hepatocellular necrosis and apoptosis in the liver and mild variable tubular attenuation, karyomegaly and epithelial necrosis and apoptosis in the kidney. There was marked hepatocellular necrosis and apoptosis in the liver and hyaline droplet accumulation in the kidneys of animals treated with polyamide 80 (FIG. 31C). Because mice treated with 80 did not tolerate two sequential injections at 1 mg/kg, and single dosing resulted in moderate liver and mild kidney damage at 3 mg/kg, we chose not to test this compound further. Consistent with the findings on histopathology, mice treated with 77 and 79 had elevated AST and ALT (FIG. 31D). Mice treated with 78 had no histopathologic lesions consistent with toxicity or alterations in liver and kidney serum markers.

5.3.4 In Vitro Liver Microsomal Stability Assay

Liver pathology was the most striking abnormality and was most severe for 80. To assess if liver pathology was related to the stability of these compounds, we investigated the metabolic stability of these polyamides to liver microsome isolates. Stability to human and mouse liver microsomes with and without NADPH was tested for polyamides 77-80. Polyamide 77-79 all demonstrated high stability (>90% intact) after 1 hour incubations (Table 7). However, less than 5% of polyamide 80 remained intact after 1 hour incubation with either human or mouse liver microsomes independent of the presence of NADPH.

TABLE 7

Microsomal stability analysis of 77-80 in the presence and absence of NADPH. Samples were incubated for 1 hr at 37° C. with 1 mg/ml of human or mouse microsomes.

| | Test conc (μM) | Test species | Mean remaining parent with NADPH (%) | Mean remaining parent NADPH-free (%) |
|---|---|---|---|---|
| Verapamil high metabolism control | 1 | Human | 4.2% | 100% |
| | 1 | Mouse | 1.1% | 100% |
| Warfarin low metabolism control | 1 | Human | 100% | 100% |
| | 1 | Mouse | 100% | 100% |
| 77 | 1 | Human | 96.9% | 92.3% |
| | 1 | Mouse | 95.2% | 96.8% |
| 79 | 1 | Human | 91.9% | 100% |
| | 1 | Mouse | 92.4% | 100% |
| 78 | 1 | Human | 95.3% | 94.9% |
| | 1 | Mouse | 97.3% | 100% |
| 80 | 1 | Human | 3.0% | 3.8% |
| | 1 | Mouse | 4.0% | 4.9% |

5.3.5 Liver Uptake of Fluorescein-Polyamide Conjugates

To determine if the chemical modifications of the γ-turn corresponding to 77-80 could influence liver uptake of polyamides of otherwise identical structure, we synthesized four polyamide analogous to 77-80, but with fluorescein isothiocyanate replacing isophthalic acid at the C-terminus (FIG. 37). Mice treated with FITC-polyamide conjugate 90, which has a γ-turn substitution identical to that of 78, demonstrated less nuclear fluorescence in liver sections than the other FITC-polyamide conjugates (FIG. 38). Mice treated with FITC-polyamide conjugate 91, which has the γ-turn corresponding to 80, demonstrated the most intense nuclear fluorescence in liver sections.

5.3.6 Cellular Uptake and Cytotoxicity

To determine the biological activity of 78 in LNCaP cells we first looked for evidence nuclear localization using fluorescein analog 90. The fluorescein analog of 77, compound 88, was used as benchmark. Confocal microscopy of LNCaP cells incubated with 2 μM of 88 or 90 for 24 hr showed robust nuclear localization (FIG. 32A). Viability of LNCaP cells was also reduced in a dose dependent manner by 78, with the half maximal inhibitory concentration at 2.1±0.3 μM (FIG. 32B).

5.3.7 Biological Characterization

Previously we found 77 to affect the RNA polymerase II holoenzyme, leading to the degradation of the large subunit, RPB1, and increase cellular p53 protein (24). Similarly, polyamide 78 reduced RPB1 levels when incubated with LNCaP cells at 10 μM for 72 h (FIG. 32C). The level of p53 protein, as well as the transcripts of several p53 target genes, was also increased after treatment with 78 (FIG. 32D-E). In addition, treatment of LNCaP cells with 10 μM of 78 for 48 h did not result in increased DNA damage by the comet assay (FIG. 32F).

5.3.8 Antitumor Activity

Next, we tested the activity of 78 against LNCaP xenografts in immunocompromised mice. Male NSG immunocompromised mice were engrafted with 2.5 million LNCaP cells. When the tumors reached 200 mm$^3$ (0.5×L×W$^2$) treatment was initiated. Mice were treated with either 78 (SC, 1 mg/kg in 20% DMSO/normal saline, n=14) or vehicle (20% DMSO/normal saline, n=14) once every three days for a cycle of six injections. The animals were then sacrificed two days after the final injection (FIG. 33A). Both groups of animals demonstrated minimal weight loss and no signs of distress during the course of the experiment (FIG. 33B).

Mice treated with 78 had smaller tumors than those treated with vehicle (T/C=52.4%) (FIG. 33C).

To assess the toxicity of the treatment regimen in healthy animals, male C57BL/6J mice were treated with an identical regimen as the tumor-bearing mice and were sacrificed two days after the final injection. Because the liver and kidney were identified as the target organs of toxicity in our previous study, we assessed relevant serum markers for liver and kidney pathology (FIG. 33D). Treated mice demonstrated no elevations in AST, ALT, total bilirubin, creatinine, or BUN. To examine if 78 has an effect on circulating blood counts, whole blood was sampled before treatment and at the time of sacrifice. No significant hematologic changes were noted for the total white blood cell, total red blood cell, hemoglobin, neutrophil, or lymphocyte count (FIG. 33E).

5.4 Discussion

Py-Im polyamides interfere with DNA-dependent processes, including transcription, through non-covalent binding to the minor groove and do not result in significant levels of genotoxicity (24). These characteristics of polyamides may represent an advancement over current DNA-targeted cancer therapies since development of treatment resistance and secondary diseases has been linked to drug induced DNA damage (12, 13, 30). Our recent demonstration of the antitumor efficacy of polyamide 77 against LNCaP xenografts raises the possibility that the Py-Im polyamide technology platform could be developed into a new class of oncologic therapeutics (24). However, a more thorough understanding of the effects of selected polyamides in preclinical animal models is required. Although extensive prior work has demonstrated bioavailability of hairpin polyamides in rodents (28, 31-33), the physiological effects of polyamides in an animal model have not been systematically examined. Based on our lead polyamide 77, we synthesized three additional polyamides and varied the γ-turn. This chemical change does not alter DNA target sequence, but affects animal toxicity and tissue distribution in mice (28).

We find that subtle changes to the substitution on the γ-turn can dramatically impact systemic toxicity of the selected polyamides in rodents. In line with previously published work, compound 77 caused weight reduction in animals treated at 10 mg/kg but caused no other visible side effects (28). Compound 80 lead to pronounced deterioration in the animals' condition at 3 and 10 mg/kg. Initially, the toxicity associated with compound 80 was attributed to the acetylation of the primary amine since acetylation generally leads to increased toxicity in cell culture (27). However, the un-acetylated version of 80, compound 79, also demonstrated marked toxicity towards the animals while the acetylated version of 77, compound 78, showed no adverse effects, suggesting the acetylation of the amine is not the sole contributor to differences in toxicity.

Furthermore, a previous study reported that a cyclic polyamide with a (R)-3,4-diaminobutyric acid turn β-substitution) was more toxic than its hairpin counterpart, which possessed a (R)-2,4-diaminobutyric acid turn (α-substitution). To see if the cyclic version of 77 lead to increased animal toxicity we synthesized 87. This compound was detectable in the serum after SC injection and was found to have less effect on animal weight than 77. This suggests the increase in polyamide induced toxicity is associated with the transition of the (R)-2,4-diaminobutyric acid turn to the (R)-3,4-diaminobutyric acid turn. Whether this is a general finding for the entire class of Py-Im polyamides remains to be seen.

To identify the cause of animal morbidity we conducted histopathological analysis on sacrificed animals. We found the liver and kidney to be the main organs of pathology for compounds 77, 79, 80, and 87. Compound 78 caused no detectable organ damage. Liver damage was most pronounced for 79 at 10 mg/kg, and 80 at 3 and 10 mg/kg. Compound 87 caused moderate damage to both the liver and kidney at 3 and 10 mg/kg. We further confirmed our histopathology results with serum measurements of ALT, AST, total bilirubin, BUN, and creatinine. The liver damage markers ALT and AST were significantly elevated at higher doses of 77, 79, 80, and 87. Blood urea nitrogen levels were found to be elevated for 79 at 10 mg/kg and 80 at 3 and 10 mg/kg.

In addition to single dose experiments we also examined the effects of 77-80 on animal health after multiple treatments with an injection regimen that was identical to the treatment cycle used in our previous xenograft study (24). We found compounds 77-78 had minimal effect on animal weight over 3 injections of 1 mg/kg, while compound 80 caused acute distress in the animals after 2 injections. Histopathology and serum marker analysis was able to detect liver and kidney damage in animals treated with all compounds except 78.

Since the liver is most affected by polyamides, we speculated enzymatic degradation of the compounds may contribute to animal toxicity. To test the stability of compounds 77-80 in the liver we conducted microsomal degradation assays with human and mice liver microsomes. Compounds 77-79 was found to be >90% intact after a 60 min incubation with 1 mg/ml of microsomes. Therefore, the reduced liver toxicity by 78 as compared to 77, 79, and 80, may not be explained on the basis of differing stability to liver microsomes. Interestingly, while 80 was previously reported to be stable against rat and human microsomes (34), less than 5% of compound 80 was remaining at the end of the assay. This may be explained by the lower amount of enzyme (0.3 mg/ml) used in the previous assay.

The tissue distribution of Py-Im polyamides is affected by structure (28, 35). In our previous pharmacokinetic study we showed 80 had greater localization to the lung, liver, and kidney than 77 (28). Thus, differences in liver uptake of compounds 77-80 may contribute to the differences in animal toxicity. To visualize nuclear uptake we synthesized fluorescein analogues of 77-80. Of the four compounds, 90 (the fluorescein analogue of 78) showed the least amount of nuclear localization, which may explain the apparent lack of animal toxicity. A detailed pharmacokinetic analysis of 78 and 79 could provide more information on the structural dependent bioavailability of these compounds. However, t remains a challenge for the field whether predictable correlation between polyamide structure and tissue distribution can be achieved.

Polyamide 77 was shown to exert cellular toxicity, in part, through the inhibition of transcription (24). In line with previous work, polyamide 78, was also found to affect cellular level of RPB1 and p53, which suggests the cytotoxic effects of 78 also stems from transcription inhibition. Furthermore, no increased DNA fragmentation was observed when cells were treated with 78, indicating the compound interferes with transcription in a nongenotoxic manner.

In addition to exhibiting similar biological activity in cell culture and having reduced animal toxicity, 78 also demonstrated antitumor activity towards LNCaP xenografts. Tumor-bearing animals and wild type animals were able to sustain 6 injections of 78 without showing any signs of duress. Further characterization of serum chemistries and hematology markers indicates compound 78 is well tolerated by the animals.

In conclusion, we have identified a structural motif that affects the animal toxicity of Py-Im polyamides. The transition of the (R)-2,4-diaminobutyric acid turn to a (R)-3,4-diaminobutyric acid turn significantly increases the animal liver and kidney damage caused by polyamides in this study. From the four compounds, we have identified polyamide 78, which contains an acetamide at the α-position of the turn unit demonstrates no detectable animal toxicity at 10 mg/kg. This compound behaves similarly to 77 in cell culture, and retains antitumor activity towards LNCaP xenografts. This second-generation hairpin polyamide provides a promising lead for the development of Py-Im polyamides as anticancer therapeutics.

5.5 Methods 5.5.1 Synthesis of Polyamides

Py-Im polyamides 77-80 and 88-91 were synthesized on Kaiser oxime resin (Novabiochem) as previously described (15, 36). Complete oligomers were cleaved from resin using 3,3'-diamino-N-methyl-dipropylamine and purified by reverse-phase HPLC in 0.1% aqueous TFA and acetonitrile (37). Isophthalic acid and fluorescein isothiocyanate conjugates were synthesized as previously described (38). Cyclic polyamide 87 was synthesized on 2-Chlorotrityl chloride resin (Bachem) as previously described (39). Deprotection of the γ-turn was performed as described (26). Hairpin polyamides 78, 80, 90, and 91 were acetylated as previously described (26, 34). Polyamides 77-80 and 87-91 were purified again by reverse phase HPLC after final conjugation. All polyamide molecular weight was measured by MALDI-ToF mass spectrometry (Table 8), and compound purity of >95% was determined by analytical HPLC.

TABLE 8

MALDI-ToF analysis of compounds.

| Compound | Chemical Formula | | Calculated Mass | Observed Mass |
|---|---|---|---|---|
| 77 | C65H76N22O12 | [M + H]+ | 1357.44 | 1357.86 |
| 79 | C65H76N22O12 | [M + H]+ | 1357.44 | 1357.69 |
| 78 | C67H78N22O13 | [M + H]+ | 1399.48 | 1399.91 |
| 80 | C67H78N22O13 | [M + H]+ | 1399.48 | 1399.36 |
| 87 | C54H61N21O10 | [M + Na]+ | 1186.5 | 1186.6 |

5.5.2 Chemicals and Animals

Ten percent neutral buffered formalin was purchased from Richard-Allan Scientific. Six to eight week old male C57BL/6J mice were purchased from Jackson labs.

5.5.3 Thermal Denaturation Assay

Thermal stabilization of the DNA oligo 5'-TTGC TGTTCTGCAA-3' (SEQ ID NO:37) by 77-80 (target sequence underlined) was determined as previously described (26).

5.5.4 Animal Weight Loss Analysis

All animal experiments were conducted under an approved protocol at the California Institute of Technology. Animals were allowed to adjust for 3 days after arrival before treatment. Compounds were quantified with a UV/Vis spectrophotometer using extinction coefficient of 69500 $M^{-1} \cdot cm^{-1}$ at $\lambda_{max}$ near 315 nm. For single injection weight loss experiments, the animals were separated into 3 treatment groups receiving 1 mg/kg, 3 mg/kg, or 10 mg/kg of compound in up to 200 μL of a 25% DMSO/saline vehicle, with 4 animals per group. Animals were monitored daily for weight loss over 9 days and sacrificed. For repeated injection experiments the animals were separated into groups of 3 and injected with 1 mg/kg of 1-4 once every 3 days and sacrificed two days after the last injection. Weight was recorded on days of injection and at the experiment endpoint.

5.5.5 Animal Histopathology Analysis

Sacrificed animals from weight loss experiments were fixed in 10% formalin and sent for histopathology analysis by IDEXX-RADIL. Histopathologic analysis was performed on the cecum, duodenum, heart, ileum, kidney, liver, lung, pancreas, spleen, and stomach. Tissue analysis was performed as a blind study to the identity of the animals.

5.5.6 Serum Analysis

Serum from treated animals were collected by retroorbital bleeding. Blood samples were centrifuged at 6,000 rpm for 5 min to collect the serum. Serum ALT, AST, total bilirubin, BUN, and creatinine levels were sent for analysis by IDEXX-RADIL. Serum analysis was performed as a blind study to the identity of the animals. For hematology analysis, blood was collected from 5 male C57BL6/J mice by retroorbital bleed and sent for hematological analysis in $K_2$EDTA coated BD Microcontainers™. The animals were allowed to recover for 1 week before treatment with 79 using the same injection conditions as the NSG mice. At the treatment endpoint the animals were bled again and euthanized. Blood samples for serum chemistry analysis and hematology analysis were prepared separately. All samples were sent for analysis at IDEXX-RADIL.

5.5.7 Liver Microsomal Stability Analysis

Liver microsomal stability of 77-80 was performed by Apredica. Briefly, each polyamide was incubated with 1 mg/ml human or mouse microsomes at 37° C. The reaction was incubated in 100 mM $KH_2PO_4$, 2 mM NADPH, 3 mM $MgCl_2$ at pH 7.4. Samples were also incubated in the absence of NADPH to detect NADPH-free degradation. After 60 min the samples were mixed with an equal volume of ice cold methanol stop solution. The mixture was allowed to sit on ice for at least 10 min and mixed with an equal volume of water. The samples were then centrifuged to remove the precipitates and the samples were analyzed by LC/MS/MS. Data represents % remaining by comparing with time zero concentration. The experiments were performed in duplicate.

5.5.8 Tissue Distribution of Fluorescein Tagged Polyamides

Male C57BL/6J mice (n=2 per group) were injected with 50 nmol (~3 mg/kg) of 88-91 and then sacrificed 24 hours later. Tissue was excised and processed as previously described (20). The tissues were excised and fixed in 10% Neutral Buffered Formalin for 48 hours. They were subsequently cryoprotected in 15% and 30% aqueous sucrose solution (w/v) for 24 hours each, embedded in a medium for frozen sections (Sakura) and frozen on dry ice. Fluorescence intensity in liver tissue was assessed by laser confocal microscopy in 10 μm thick sections on slides mounted with a ProLong antifade reagent (Invitrogen).

5.5.9 Cell Viability Assays

LNCaP cells were plated in clear bottom 96-well plates at 5,000-7,500 cells per well and allowed to adhere for 36-48 h. Compounds were then added in fresh media. Cell metabolic activity was determined by the WST-1 assay (Roche) after 72-h incubation with cells. Quantification was performed on a Perkin Elmer Victor 3 plate reader. Assays were performed in biological triplicates.

5.5.10 Protein ELISA Assays

Cellular levels of RPB1 and p53 protein in LNCaP cells after treatment with 10 μM 3 for 72 h were determined by ELISA. Cells treated with DMSO vehicle and 1 μM doxorubicin for 24 h were used as control. Cellular RBP1 levels were determined by a RPB1 specific ELISA kit (Cusabio Life Sciences) according to manufacturer's instructions. Total cellular p53 protein level was determined with a pan-p53 ELISA kit (Roche) according to manufacturer's instructions. Assays were performed in biological triplicates.

5.5.11 Quantitative RT-PCR

LNCaP cells were plated in 12 well plates at 50,000 cells per well and allowed to adhere for 36-48 h. The cells were then treated with 1, 3, and 10 μM of 78 for 72 h. Total cellular RNA was extracted using RNEasy columns (Qiagen) following the manufacturer's protocols. Isolated RNA was reverse transcribed with Transcriptor First Strand cDNA kit (Roche). Quantitative real-time PCR was performed using SYBR Green PCR Master Mix (Applied Biosystems) on an ABI 7300 instrument. Amplification of p21, IGFBP3, and GADD45A cDNA was measured relative to β-glucuronidase using previously published primers (24). Experiments were performed in biological replicates.

5.5.12 Comet Assay

LNCaP cells were plated in 6 well plates at 100,000 cells per well and allowed to adhere for 36-48 h. The cells were then incubated with either 10 μM 78 for 48 h or 5 μM doxorubicin for 4 h. DNA damage was assayed using the Trevigen CometAssay system. Cells were harvested by gentle aspiration with PBS and prepared on slides according to the manufacturer's protocol. Comets slides were imaged on a confocal microscope (Exciter, Zeiss) at 10× magnification. Images were scored using Comet Assay Lite IV (Perceptive Instruments). More than 100 comets were scored for each condition. DNA damage is reported as percentage of DNA in the tail.

5.5.13 In Vivo Xenograft Experiments

Mice experiments were conducted under an approved protocol by the Institutional Animal Care and Use Committee of the California Institute of Technology. Male C57BL6/J mice and male NSG mice were purchased from The Jackson Laboratory. All animals were maintained on a standard light-dark cycle. LNCaP cells (2.5 million cells) were engrafted in a mixture of 1:1 media and matrigel in the left flank of NSG mice. Tumors were allowed grow to ~200 mm$^3$ (0.5×L×W$^2$) before treatment. Py-Im polyamide 78 was administered by SC injection once every 3 d at 1 mg/kg in a 20% (vol/vol) DMSO:Normal saline vehicle solution for 6 injections. Animals were sacrificed two days after the final injection. Animal weight and general health were monitored daily. Fourteen animals were used for each treatment group.

References for Example 5

1. Jemal, A.; Center, M. M.; DeSantis, C.; Ward, E. M.; *Cancer. Epidemiol. Biomarkers. Prev.* 2010, 19, 1893-1907.
2. Zelefsky, M. J.; Eastham, J. A.; Cronin, A. M.; Fuks, Z.; Zhang, Z.; Yamada, Y.; Vickers, A.; Scardino, P. T.; *J. Clin. Oncol.* 2010, 28, 1508-1513.
3. Tendulkar, R. D.; Reddy, C. A.; Stephans, K. L.; Ciezki, J. P.; Klein, E. A.; Mahadevan, A.; Kupelian, P. A.; *Int. J. Radiat. Oncol., Biol., Phys.* 2012, 82, 1397-1404.
4. Chen, Y.; Scher, H. I.; *Nat. Rev. Clin. Oncol.* 2012, 9, 70-72.
5. Li, Y.; Chan, S. C.; Brand, L. J.; Hwang, T. H.; Silverstein, K. A.; Dehm, S. M.; *Cancer Res.* 2013, 73, 483-489.
6. Mostaghel, E. A.; Marck, B. T.; Plymate, S. R.; Vessella, R. L.; Balk, S.; Matsumoto, A. M.; Nelson, P. S.; Montgomery, R. B.; *Clin. Cancer Res.* 2011, 17, 5913-5925.
7. Koumenis, C.; Giaccia, A.; *Mol. Cell. Biol.* 1997, 17, 7306-7316.
8. Jung, Y.; Lippard, S. J.; *J. Biol. Chem.* 2006, 281, 1361-1370.
9. Pommier, Y.; *Nat. Rev. Cancer* 2006, 6, 789-802.
10. Mantoni, T. S.; Reid, G.; Garrett, M. D.; *Oncogene* 2006, 25, 3139-3149.
11. Haffner, M. C.; Aryee, M. J.; Toubaji, A.; Esopi, D. M.; Albadine, R.; Gurel, B.; Isaacs, W. B.; Bova, G. S.; Liu, W. N.; Xu, J. F.; Meeker, A. K.; Netto, G.; De Marzo, A. M.; Nelson, W. G.; Yegnasubramanian, S.; *Nat. Genet.* 2010, 42, 668-675.
12. Arseneau, J. C.; Sponzo, R. W.; Levin, D. L.; Schnipper, L. E.; Bonner, H.; Young, R. C.; Canellos, G. P.; Johnson, R. E.; DeVita, V. T.; *N. Engl. J. Med.* 1972, 287, 1119-1122.
13. Sun, Y.; Campisi, J.; Higano, C.; Beer, T. M.; Porter, P.; Coleman, I.; True, L.; Nelson, P. S.; *Nat. Med.* 2012, 18, 1359-1368.
14. Dervan, P. B.; *Bioorg. Med. Chem.* 2001, 9, 2215-2235.
15. Best, T. P.; Edelson, B. S.; Nickols, N. G.; Dervan, P. B.; *Proc. Natl. Acad. Sci. U.S.A.* 2003, 100, 12063-12068.
16. Olenyuk, B. Z.; Zhang, G. J.; Klco, J. M.; Nickols, N. G.; Kaelin, W. G., Jr.; Dervan, P. B.; *Proc. Natl. Acad. Sci. U.S.A.* 2004, 101, 16768-16773.
17. Nickols, N. G.; Dervan, P. B.; *Proc. Natl. Acad. Sci. U.S.A.* 2007, 104, 10418-10423.
18. Nickols, N. G.; Jacobs, C. S.; Farkas, M. E.; Dervan, P. B.; *ACS Chem. Biol.* 2007, 2, 561-571.
19. Raskatov, J. A.; Meier, J. L.; Puckett, J. W.; Yang, F.; Ramakrishnan, P.; Dervan, P. B.; *Proc. Natl. Acad. Sci. U.S.A.* 2012, 109, 1023-1028.
20. Nickols, N. G.; Szablowski, J. O.; Hargrove, A. E.; Li, B. C.; Raskatov, J. A.; Dervan, P. B.; *Mol. Cancer. Ther.* 2013, 12, 675-684.
21. Kielkopf, C. L.; Baird, E. E.; Dervan, P. B.; Rees, D. C.; *Nat. Struct. Biol.* 1998, 5, 104-109.
22. Kielkopf, C. L.; White, S.; Szewczyk, J. W.; Turner, J. M.; Baird, E. E.; Dervan, P. B.; Rees, D. C.; *Science* 1998, 282, 111-115.
23. White, S.; Szewczyk, J. W.; Turner, J. M.; Baird, E. E.; Dervan, P. B.; *Nature* 1998, 391, 468-471.
24. Yang, F.; Nickols, N. G.; Li, B. C.; Marinov, G. K.; Said, J. W.; Dervan, P. B.; *Proc. Natl. Acad. Sci. U.S.A.* 2013, 110, 1863-1868.
25. Dervan, P. B.; Edelson, B. S.; *Curr. Opin. Struct. Biol.* 2003, 13, 284-299.
26. Dose, C.; Farkas, M. E.; Chenoweth, D. M.; Dervan, P. B.; *J. Am. Chem. Soc.* 2008, 130, 6859-6866.
27. Meier, J. L.; Montgomery, D. C.; Dervan, P. B.; *Nucleic Acids Res.* 2012, 40, 2345-2356.
28. Synold, T. W.; Xi, B.; Wu, J.; Yen, Y.; Li, B. C.; Yang, F.; Phillips, J. W.; Nickols, N. G.; Dervan, P. B.; *Cancer Chemother. Pharmacol.* 2012, 70, 617-625.
29. Raskatov, J. A.; Hargrove, A. E.; So, A. Y.; Dervan, P. B.; *J. Am. Chem. Soc.* 2012, 134, 7995-7999.
30. Salehan, M. R.; Morse, H. R.; Br. *J. Biomed. Sci.* 2013, 70, 31-40.
31. Nagashima, T.; Aoyama, T.; Yokoe, T.; Fukasawa, A.; Fukuda, N.; Ueno, T.; Sugiyama, H.; Nagase, H.; Matsumoto, Y.; *Biol. Pharm. Bull.* 2009, 32, 921-927.

32. Nagashima, T.; Aoyama, T.; Fukasawa, A.; Watabe, S.; Fukuda, N.; Ueno, T.; Sugiyama, H.; Nagase, H.; Matsumoto, Y.; *J. Chromatogr. B. Analyt. Technol. Biomed. Life. Sci.* 2009, 877, 1070-1076.
33. Fukasawa, A.; Nagashima, T.; Aoyama, T.; Fukuda, N.; Matsuda, H.; Ueno, T.; Sugiyama, H.; Nagase, H.; Matsumoto, Y.; *J. Chromatogr. B. Analyt. Technol. Biomed. Life. Sci.* 2007, 859, 272-275.
34. Chenoweth, D. M.; Harki, D. A.; Phillips, J. W.; Dose, C.; Dervan, P. B.; *J. Am. Chem. Soc.* 2009, 131, 7182-7188.
35. Harki, D. A.; Satyamurthy, N.; Stout, D. B.; Phelps, M. E.; Dervan, P. B.; *Proc. Natl. Acad. Sci. U.S.A.* 2008, 105, 13039-13044.
36. Puckett, J. W.; Green, J. T.; Dervan, P. B.; *Org. Lett.* 2012, 14, 2774-2777.
37. Belitsky, J. M.; Nguyen, D. H.; Wurtz, N. R.; Dervan, P. B.; *Bioorg. Med. Chem.* 2002, 10, 2767-2774.
38. Nickols, N. G.; Jacobs, C. S.; Farkas, M. E.; Dervan, P. B.; *Nucleic Acids Res.* 2007, 35, 363-370.
39. Li, B. C.; Montgomery, D. C.; Puckett, J. W.; Dervan, P. B.; *J. Org. Chem.* 2013, 78, 124-133.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All publications, including patent documents and scientific articles, referred to in this application and the bibliography and attachments are incorporated by reference in their entirety for all purposes to the same extent as if each individual publication were individually incorporated by reference. The article "a" as used herein means one or more unless indicated otherwise. All headings are for the convenience of the reader and should not be used to limit the meaning of the text that follows the heading, unless so specified.

What is claimed is:

1. A polyamide of structure 1 as follows:

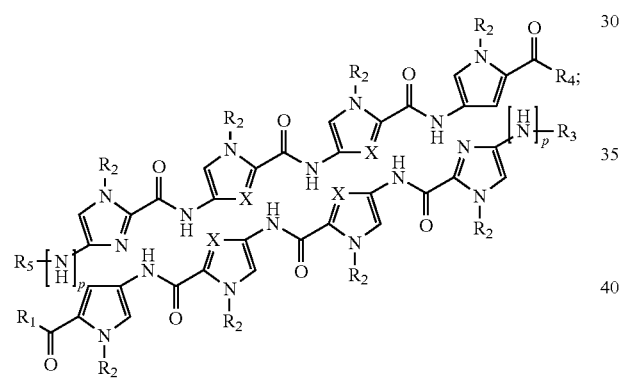

wherein each X is independently selected from CH, N, or COH; wherein each pyrrole unit of structure 2 as follows:

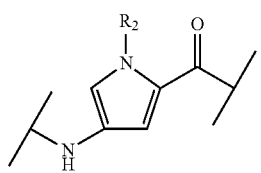

Pyrrole may be independently replaced by a beta-alanine of structure 3 as follows:

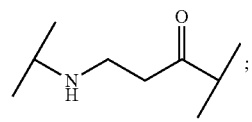

beta alanine wherein each $R_2$ is independently selected from H, a $C_{1-5}$ alkyl, a $C_{1-5}$ alkenyl, a $C_{1-5}$ alkynyl; wherein $R_3$ is linked to $R_4$ through structure 4 as follows:

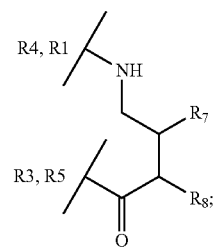

wherein $R_1$ is selected from structure 25 as follows:

and from structures 27 and 29-31, 37, 39-41 as follows:

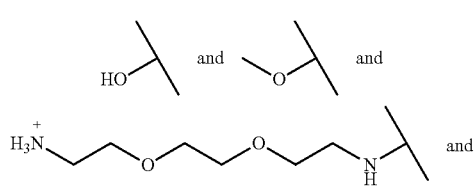

-continued

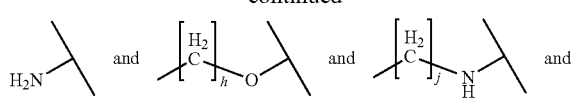

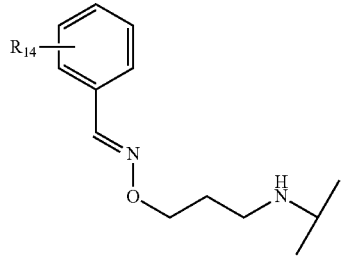

and

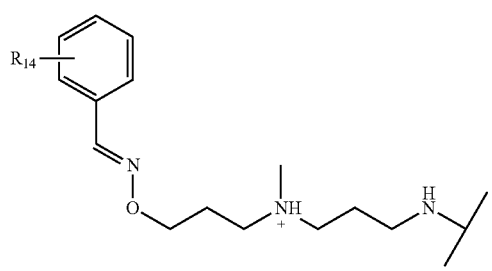

and from structures 49-54 as follows:

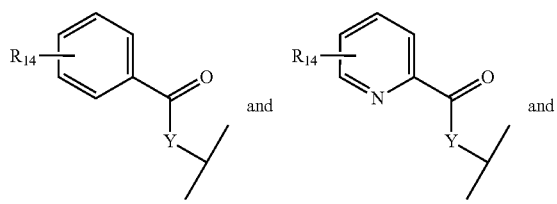

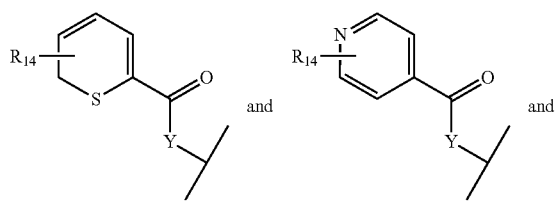

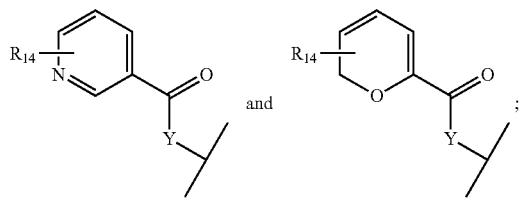

wherein y is selected from structures 55-57 as follows:

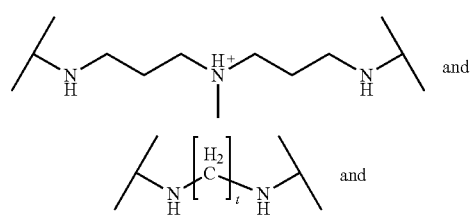

-continued

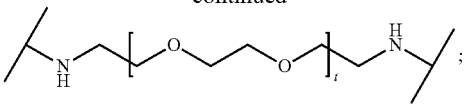

wherein $R_5$ is selected from $CH_3$ and from structures 58-61 as follows:

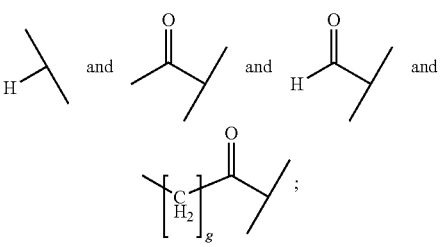

wherein one of $R_7$ and $R_5$ is structure 7 as follows:

and the other one of $R_7$ and $R_5$ is selected from OH, SH, $CH_3$, $NH_2$, $CH_2CH_3$, $NO_2$, COOH, COOMe, COOEt, halogen, F, Cl, Br, I, $CH_2F$, $CH_2Cl$, $CH_2Br$, $CH_2I$, $CHF_2$, $CHCl_2$, $CHBr_2$, $CHI_2$, $CF_3$, $CCl_3$, $CBr_3$, and $Cl_3$ and from structures 8-13 as follows:

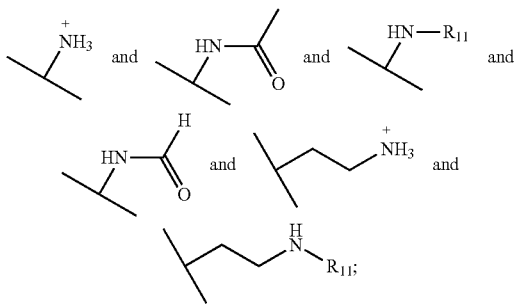

wherein $R_{11}$ is selected from OH, $CH_3$, $CH_2CH_3$, and from structures 59-61 as follows:

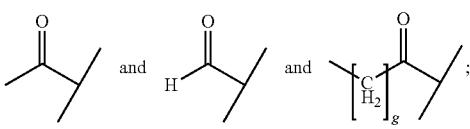

wherein each $R_{14}$ represents one, two, three, four, or five sidechains up to the maximum number with each $R_{14}$ being independently selected from SH, $CH_3$, $CH_2CH_3$, COOMe, COOEt, $CH_2Cl$, $CH_2Br$, $CH_2I$, $CHCl_2$, $CHBr_2$, and $CHI_2$; and wherein each d, e, f, g, h, j, t is independently selected from 1-10, and the p adjacent to $R_5$ is 0 and the p adjacent to $R_3$ is 1.

2. The composition of claim 1, wherein $R_1$ is selected from structures 40 and 41 as follows:

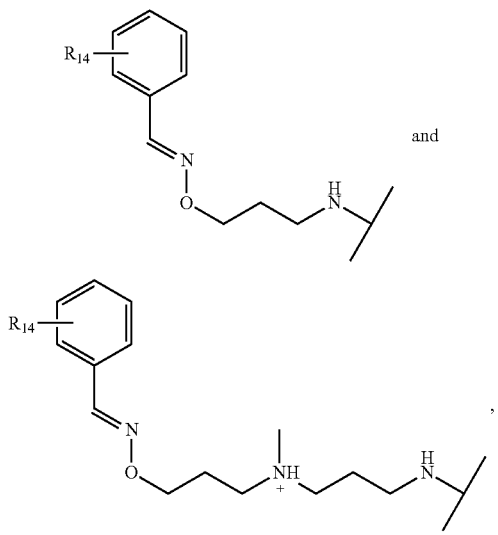

and from structures 49-54 as follows:

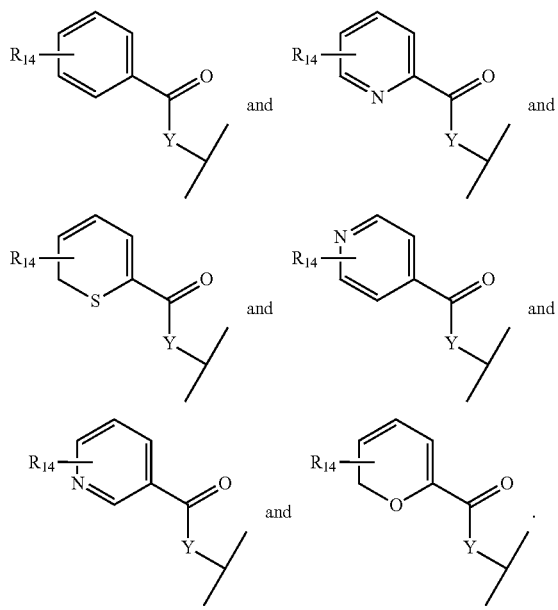

3. The composition of claim 1, wherein each tetramer of the polyamide of structure 1 is independently selected from imidazole-imidazole-imidazole-pyrrole, imidazole-imidazole-pyrrole-pyrrole, imidazole-pyrrole-pyrrole-pyrrole, and imidazole-pyrrole-imidazole-pyrrole.

4. The composition of claim 1, wherein one of $R_7$ and $R_8$ is structure 7 as follows:

and the other one of $R_7$ and $R_8$ is selected from structures 8-13 as follows:

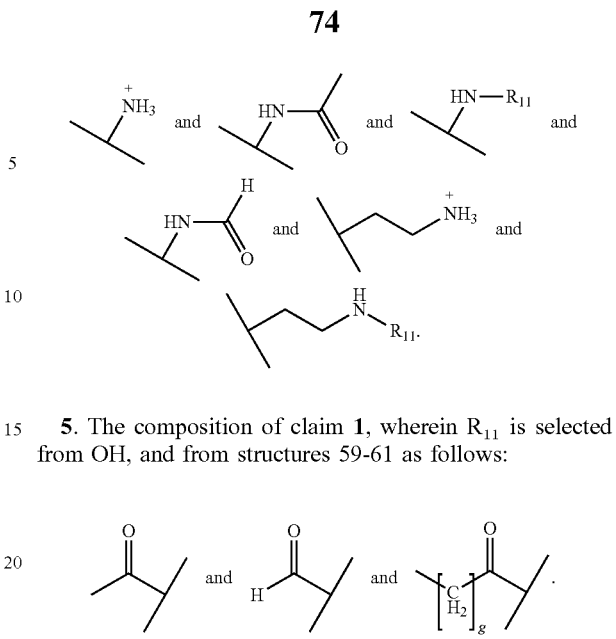

5. The composition of claim 1, wherein $R_{11}$ is selected from OH, and from structures 59-61 as follows:

6. The composition of claim 1, wherein one of $R_7$ and $R_8$ is structure 7 as follows:

and the other one of $R_7$ and $R_8$ is selected from structures 8-13 as follows:

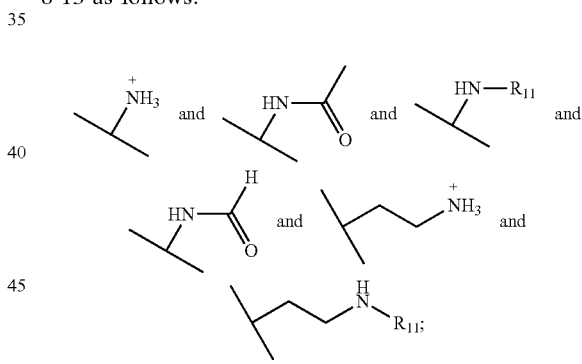

wherein $R_{11}$ is selected from OH, and from structures 59-61 as follows:

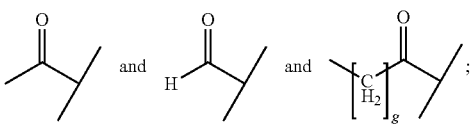

and wherein each $R_{14}$ represents one, two, three, four, or five sidechains up to the maximum number with each $R_{14}$ being independently selected from SH, $CH_3$, $CH_2CH_3$, COOMe, COOEt, $CH_2Cl$, $CH_2Br$, $CH_2I$, $CHCl_2$, $CHBr_2$, and $CHI_2$.

7. The composition of claim 1, wherein said composition further comprises a pharmaceutically acceptable carrier.

8. The composition of claim 2, wherein said composition further comprises a pharmaceutically acceptable carrier.

9. The composition of claim 6, wherein said composition further comprises a pharmaceutically acceptable carrier.
10. The composition of claim 1, wherein $R_1$ is selected from structures 49-54 as follows:
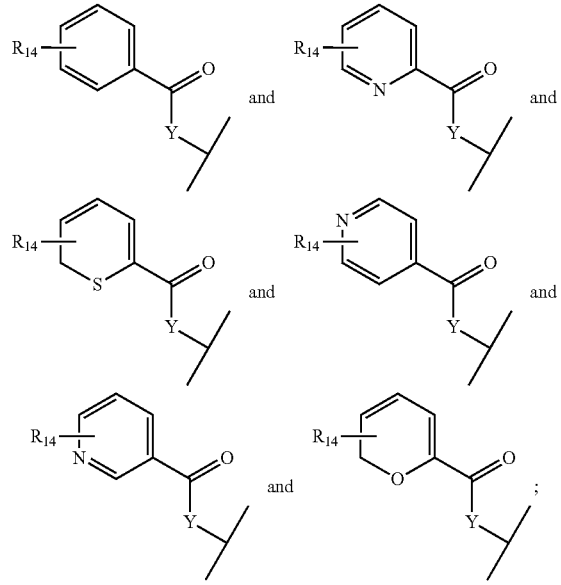
and wherein y is structure 57 as follows:
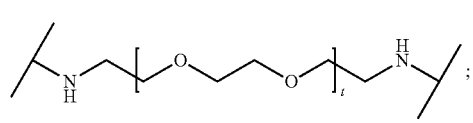
and wherein t is 1.
11. The composition of claim 1, wherein $R_1$ is selected from structures 49-54 as follows:
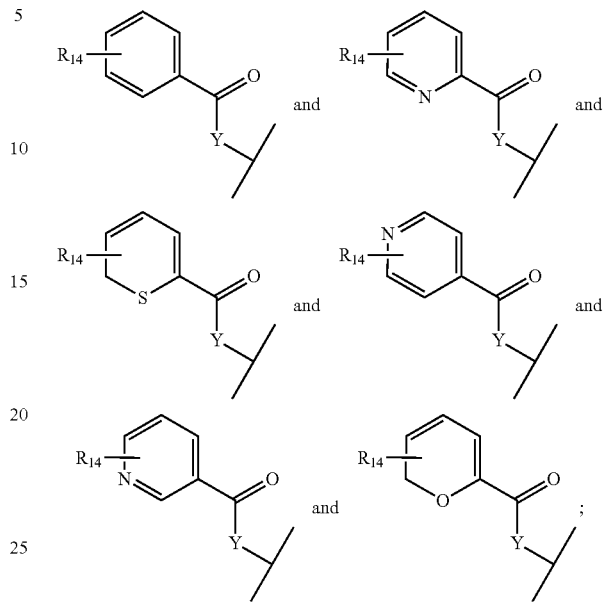
and wherein y is structure 55 as follows:
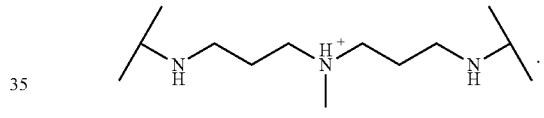
* * * * *

UNITED STATES PATENT AND TRADEMARK OFFICE
CERTIFICATE OF CORRECTION

PATENT NO.        : 9,630,950 B2                            Page 1 of 1
APPLICATION NO.   : 14/027073
DATED             : April 25, 2017
INVENTOR(S)       : Peter B. Dervan et al.

It is certified that error appears in the above-identified patent and that said Letters Patent is hereby corrected as shown below:

On the Title Page

Left Column, item number (60), Line 3:
"filed on Sep. 13, 2013" should read --filed on Sep. 13, 2012--;

In the Claims

Claim 1, Column 72, Line 22:
"wherein one of $R_7$ and $R_5$" should read --wherein one of $R_7$ and $R_8$--;

Claim 1, Column 72, Line 29:
"and the other one of $R_7$ and $R_5$" should read --and the other one of $R_7$ and $R_8$--;

Claim 1, Column 72, Line 32:
"and $Cl_3$" should read --and $Cl_3$--.

Signed and Sealed this
Thirtieth Day of May, 2017

Michelle K. Lee
*Director of the United States Patent and Trademark Office*